US006812025B2

(12) United States Patent
Goff et al.

(10) Patent No.: US 6,812,025 B2
(45) Date of Patent: Nov. 2, 2004

(54) TWO HYBRID ASSAY THAT DETECTS HIV-1 REVERSE TRANSCRIPTASE DIMERIZATION

(75) Inventors: Stephen P. Goff, Tenafly, NJ (US); Gilda Tachedjian, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/009,433

(22) PCT Filed: Jun. 6, 2001

(86) PCT No.: PCT/US01/18339
§ 371 (c)(1),
(2), (4) Date: Jun. 12, 2002

(87) PCT Pub. No.: WO01/94645
PCT Pub. Date: Dec. 13, 2001

(65) Prior Publication Data
US 2002/0197598 A1 Dec. 26, 2002

Related U.S. Application Data

(63) Continuation-in-part of application No. 09/588,939, filed on Jun. 6, 2000, now abandoned.

(51) Int. Cl.[7] .............................. C12N 5/16; C12Q 1/70; C12P 21/06
(52) U.S. Cl. ............................ 435/339.1; 435/5; 435/6; 435/69.7
(58) Field of Search ............................... 435/5, 6, 69.7, 435/339.1

(56) References Cited
U.S. PATENT DOCUMENTS
5,922,856 A   7/1999   Fritz et al.

OTHER PUBLICATIONS

U.S. patent application No. 10/006,626, filed Dec. 6, 2001.
U.S. patent application No. 10/670,652, filed Sep. 25, 2003.
Tachedjian, G. et al., (2000) "Analysis of Mutations and Suppressors Affecting Interactions Between the Subunits of the HIV Type–1 Reverse Transcriptase" *PNAS* 97(12):6334–6339.

Boyer, P. et al. (1993) "Subunit Specificity of Mutations that Confer Resistance to Nonnucleoside Inhibitors in Human Immunodeficiency Virus Type–1 Reverse Transcriptase" *Antimicrobial Agents and Chemotherapy*, 38(9):1909–1914.

Baillon, J.G. et al. (1991) "A Leucine Zipper–like Motif may Mediate HIV Reverse Transcriptase Subunit Binding", *New Biol*, 3:1015–019.

Becerra, S., et al. (1991) "Protein–Protein Interactions of HIV–1 Reverse Transcriptase: Implication of Central and C–terminal Regions in Subunit Binding" *Biochemistry*, 30:11707–11719.

Debyser, Z. and De Clercq, E., (1996) "Chemical Crosslinking of the Subunits of HIV–1Reverse Transcriptase", *Protein Science* 5:278–286.

Ding, J. et al. (1995) "Structure of HIV–1 Reverser Transcriptase in a Complex with the Non–Nucleoside Inhibitor Alpha–APA r 95845 at 2.8 A Resolution" *Structure* 3:365–379.

(List continued on next page.)

*Primary Examiner*—Hankyel T. Park
(74) *Attorney, Agent, or Firm*—John P. White; Cooper & Dunham LLP

(57) ABSTRACT

This invention provides methods of determining whether a compound inhibits HIV-1 reverse transcriptase. This invention provides methods of determining whether a compound inhibits formation of a complex between a p66 and p51 subunit polypeptides of HIV-1 reverse transcriptase. This invention provides a method of determining whether a compound enhances formation of a complex between a p66 and p51 subunit polypeptides of HIV-1 reverse transcriptase. This invention provides methods of determining whether a compound inhibits formation of a complex between two p66 subunit polypeptides of HIV-1 reverse transcriptase. This invention provides methods of determining whether a compound enhances formation of a complex between two p66 subunit polypeptides of HIV-1 reverse transcriptase.

48 Claims, 15 Drawing Sheets-

OTHER PUBLICATIONS

Divita, G., Restle, T., and Goody, R.S. (1993) "Characterization of the Dimerization process of HIV–1 Reverse Transcriptase Heterodimer Using Intrinsic Protein Fluorescence" *FEBS Lett.* 324:153–158.

Divita, G., et al., (1994) "Inhibition of Human Immunodeficiency Virus Type I Reverse Transcriptase Dimerization Using Synthetic Peptides Derived from the Connection Domain" *J. Biol.Chem.*, 269:13080–13083.

Esnouf, R., et al. (1995) "Mechanism of Inhibition of HIV–1 Reverse Transcriptase by Non–Nucleoside Inhibitors", *Nat Struct. Biol.*, 2:203–308.

Fields, S., and Song, O. (1989) "A Novel Genetic System to Detect Protein–Protein Interactions", *Nature,* 340:245–246.

Ghosh, M., et al, (1996) "Alterarions to the Primer Group of p66 HV–1 Reverse Transcriptase and Their Consequences for Template–primer Utilization", *Biochemstry* 35:8553–8562.

Goel, R., et al, (1993) "Structure/Function Studies of HIV–1 (1) Reverse Transcriptase:Dimerization–Defective Mutant L289K", *Biochemistry* 32:13012–13018.

Goody, R.S., (1995) "Rational Drug Design and HIV: Hopes and Limitations", *Nat'l Med.* 1:519–520.

Harris, D., et al., (1998): The p51 Subunit of Human Immunodeficiency Virus Type 1 Reverse Transcriptase is Essential in Loading the p66 Subunit on the Template Primer, *Biochemistry,* 37:5903–5908.

Hanes, S.D. and Brent R. (1989), "DNA Specificity of the Bicoid Activator Protein is Determined by Homeodomain Recognition Helix Residue 9", *Cell* 57:1275–1283.

Huang, H., et al. (1998) "Structure of a Covalently Trapped Catalytic Complex of HIV–1 Reverse Transcriptase Implications for Drug Resistance", *Science,* 282:1669–1675.

Jacobo–Molina, A. et al., (1993) "Crystal Structure of Human Immunodeficiency Virus Type 1 Reverse Transcriptase Complexed with Doble Stranded DNA st 3.0 a Resolution Shows Bent DNA", *Proc. Natl. Acad Sci USA,* 90:6302–6324.

Jacques, P.S., et al., (1994) "Modulation of HIV–1 Reverse Transcriptase Function in "Selectivity Deteted" p66/p51 Heterodimers", *J.Biol.Chem.* 269:1388–1393.

Kaplana, G.V., et al., (1994) "Binding and Stimulation of HIV–1 Integrase by a Human Homolog of Yeast Transcription Factor SNF5", Science, 266:2002–2006.

Kaplana, G.V., and Goff, S.P. (1993) "Genetic Analysis of Homomeric Interactions of Human Immunodeficiency Virus Type 1 Integrase Using the Yeast Two–Hybrid System" Proc. Natl. Sci. USA., 90:10593–10597.

Kohlstaedt, L.A., et al., (1992) Crstal Structure f 3.5A Resolution of HIV–1 Reverse Transcriptase Complexed with an Inhibitor, Science, 256:1783–1790.

Legrain, P., Dokhelar, M.C. and Transy, C., (1994) "Detection of protein–protein Interactions Using Differnt Vectors in the Two–Hybrid System", Nucleic Acisd Res, 22:3241–3242.

Li, X., Yuan, B. and Gof, S.P., (1997) "Gentic Analysis of Interactions Between Gag Proteins of Rous Sarcoma Virus", J. Virol., 71:5614–5630.

Li, X. et al., (1996) "Homoeric Interactions Between Transmembrane Proteins of Moloney Murine Leukemia Virus", J. Virol., 70:1266–1270.

Luban, J. et al., (1992) "Genetic Assay for Multimerization of Retrovial gag Polyproteins", J. Virol., 73:1067–1078.

Misra, H.S., Pandey, P.K. and Pandey, V.N., (1998), "An Enzymatically Active Chimeric HIV–1 Reverse Transcriptase (RT) With the Rnase–H Domain of Murine Leukemia Virus RT Exists as a Monomer", J.Bio.Chem., 273:9782–9789.

Morris, M.C., et al. (1999) "A New Potent HIV–1 Reverse Transcriptase Inhibitor, A Synthetic Peptide Derived from the Interface Subunit Domains", J. Biol Chem, 274:24941–24946.

Morris, M.C., et al., (1999) "Tje thumb Domain of the p51–Subunit is Essential for Activation of HIV Reverse Transcriptase", Biochemistry, 38:15097–15103.

Ren, J., et al., (1995) "High Resolution Structures of HIV–1 RT from Four RT–Inhibitor Complexes", Nat Struct Biol 2:293–302.

Ren, J. et al. (1995) "The Structure of HIV–1 Reverse Transcriptase Complexed with 0–chloro–TIBO: lessons for Inhibitor Design", Structure, 3:915–926.

Restle, T., Muller, B. and Goody, R.S., (1990) "Dimerizarion of Human Immunodeficiency Virus Type 1 Reverse Transcriptase. A Target for Chemotherapeutic Virus Type 1" J. Biol. Chem, 265:8986–8988.

Rodgers, D.W., et al. (1995) "The Structure of Unliganded Reverse Transcriptase from the Human Immunodeficiency Virus Type 1" Proc. Natl. Acad. Sci. USA, 92:1222–1226.

Ruden, D.M., et al., (1991) "Generating Yeast Transcriptional Activators Containing no Yeast Protein Sequences", Nature, 350:250–252.

Sluis, Cremer, N. et al., (2000) Human Immunodeficiency Virus Type 1 Reverse Transcriptase Dimer Destabilization by 1–{Sprio[4"–amino–2", 2"–dioxo–1", 2"–oxathole–5", 3'–2', 5'–bis–o–(tert–butyldimethylsiyl)–§–D–ribofuranosyl]]}–3–ethylthymine, Biochemstry, 39:1427–1433.

Wohrl, B.M., (1997) "Kinetic Analysis of Four HIV–1 Reverse Transcriptase Enzymes Muatted in the Primer Grip Region of p66. Implications for DNA Synthesis and Dimerization" J.Biol.Chem., 272:17581–17587.

FIGURE 4

| Fusion Proteins | beta-gal activity (Miller Units) |
|---|---|
| p66wt : p51wt | 3.2 |
| p66wt : pAD | 0.01 |
| p66mut : p51mut | 0.06 |
| p66wt : p51mut | 1.9 |
| p66mut : p51wt | 0.1 |

FIGURE 11
A
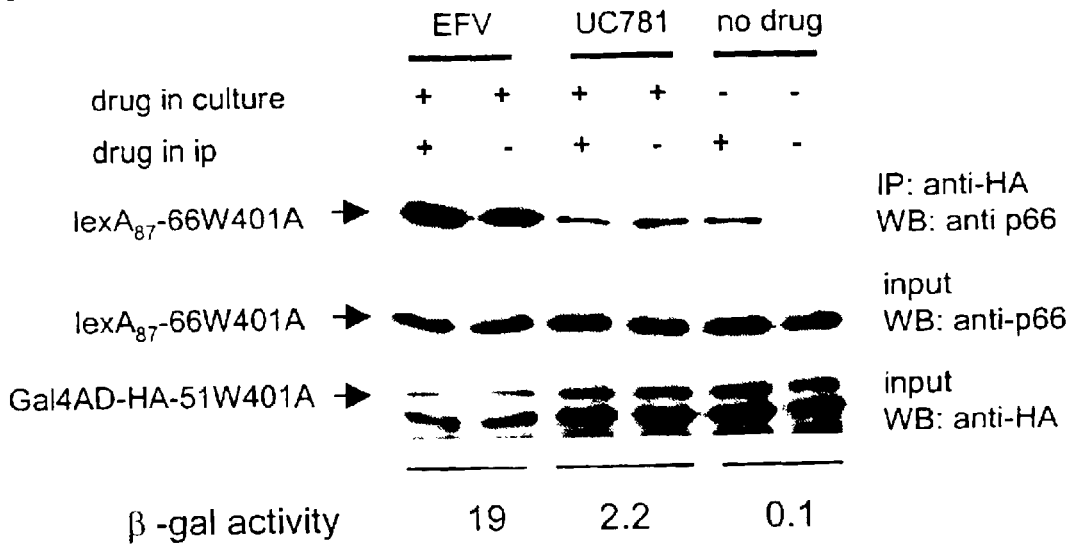
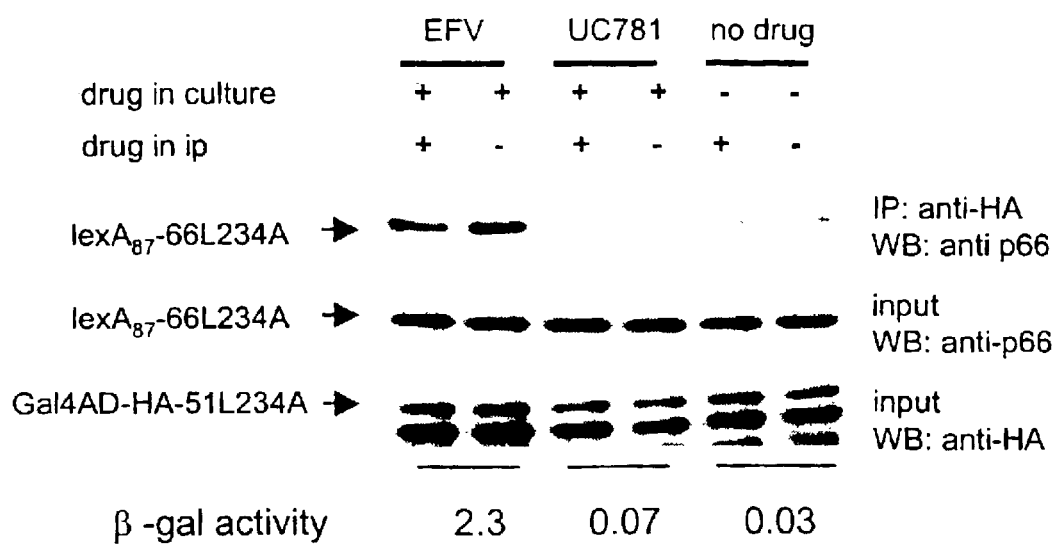

TWO HYBRID ASSAY THAT DETECTS HIV-1 REVERSE TRANSCRIPTASE DIMERIZATION

This invention is a continuation-in-part and claims the benefit of U.S. Ser. No. 09/588,939, filed Jun. 6, 2000, now abandoned the contents of which are hereby incorporated by reference into this application.

The invention disclosed herein was made in part with Government support under NIH Grant No. AI 27690. Accordingly, the government has certain rights in this invention.

Throughout this application, various publications are referenced within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

HIV-1 reverse transcriptase (RT) catalyzes the conversion of genomic RNA into cDNA. The enzyme is a heterodimer of p66 and p51 subunits, and the dimerization of these subunits is required for optimal enzyme activity. To analyze this process at the genetic level we developed constructs that permit the detection of the interaction between these subunits in the yeast two-hybrid system. Genetic analysis of RT subdomains required for heterodimerization revealed that the fingers and palm of p66 were dispensable for p51 interaction. However, as little as a 26-amino acid deletion at the C terminus of p51 prevented dimerization with p66. A primer grip mutation, L234A, previously shown to inhibit RT dimerization by biochemical assays, also prevented RT dimerization in the yeast two-hybrid system. Second-site mutations that restored RT dimerization in yeast to the L234A parent were recovered in the tryptophan repeat region at the dimer interface and at the polymerase active site, suggesting the involvement of these sites in RT dimerization. In vitro binding experiments confirmed the effects of the L234A mutation and the suppressor mutations on the interaction of the two subunits. The RT two-hybrid assay should facilitate the extensive genetic analysis of RT dimerization and should make possible the rapid screening of potential inhibitors of this essential process.

The HIV type 1 (HIV-1) reverse transcriptase (RT) is required for the conversion of genomic RNA into double-stranded proviral DNA, catalyzed by the RNA- and DNA-dependent polymerase and ribonuclease H activities of the enzyme. HIV-1 RT is an asymmetric dimer formed by the association of p66 and p51 polypeptides, which are cleaved from a large $Pr160^{GagPol}$ precursor by the viral protease during virion assembly p51 contains identical N-terminal sequences as p66, but lacks the C-terminal ribonuclease H (RNase H) domain (1). The structure of HIV-1 RT has been elucidated by x-ray crystallography in a variety of configurations, including unliganded (2), complexed to nonnucleoside RT inhibitors (3), or complexed with double-stranded DNA either with (4) or without deoxynucleotide triphosphate (5, 6). Such analyses have shown that p66 can be divided structurally into the polymerase and RNase H domains, with the polymerase domain further divided into the fingers, palm, thumb and connections subdomains (6). Although p51 has the same polymerase domains as p66, the relative orientations of these individual domains differ markedly, resulting in p51 assuming a closed structure.

The RT heterodimer represents the biologically relevant form of the enzyme; the monomeric subunits have only low catalytic activity (7). Structural analysis reveals three major contacts between p66 and p51, with most of the interaction surfaces being largely hydrophobic (8, 9). The three contacts comprise an extensive dimer interface that includes the fingers subdomain of p51 with the palm of p66, the connection subdomains of both subunits, and the thumb subdomain of p51 with the RNase H domain of p66 (9). Several single amino acid substitutions in HIV-1 RT have been shown to inhibit heterodimer association (10–12). These include the mutations L234A (10, 11), G231A (11) and W229A (11), all located in the primer grip region of the p66 subunit, and L289K (12) in the thumb subdomain. Remarkably, these mutations are not located at the dimer interface and probably mediate their effects indirectly through conformational changes in the p66 subunit.

Several biochemical assays have been used previously to specifically measure RT dimerization. Some are based on the physical separation of monomers and dimers as determined by analytical ultracentrifugation (8) and gel filtration (7). Other assays include intrinsic tryptophan fluorescence (13) chemical crosslinking (14), the use of affinity tags (15) and polymerase activity itself (7). Although these methods detect dimerization, they either lack specificity or are not easy to perform. Moreover, these assays do not facilitate the rapid genetic analysis of protein-protein interactions under physiological conditions nor are they suitable for high throughput screening for RT dimerization inhibitors.

The yeast two-hybrid (Y2H) system (16) has been exploited to study the homomeric interactions of several retroviral proteins (see, e.g., ref. 17), and heteromeric interactions between viral proteins and various cellular partners (see, e.g., ref. 18). We have used this system to perform a genetic analysis of the determinants of RT dimerization. In addition, we have identified second-site mutations that restore heterodimerization to a noninteracting mutant p66.

SUMMARY OF THE INVENTION

This invention provides a method of determining whether a compound inhibits HIV-1 reverse transcriptase which comprises:

a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the p51 subunit polypeptide of HIV-1 reverse transcriptase and the p66 subunit polypeptide of HIV-1 reverse transcriptase, thereby indicating that the compound inhibits HIV-1 reverse transcriptase.

This invention provides a method of determining whether a compound inhibits formation of a complex between a p66 subunit polypeptide of HIV-1 reverse transcriptase and a p51 subunit polypeptide of HIV-1 reverse transcriptase which comprises:

a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the p51 subunit polypeptide of HIV-1 reverse transcriptase and the p66 subunit polypeptide of HIV-1 reverse transcriptase.

This invention provides a method of determining whether a compound inhibits HIV-1 reverse transcriptase which comprises:

a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein an increased level of activity of the reporter gene determined in step (a) indicates that the compound is an activator of the formation of the complex between the p51 subunit polypeptide of HIV-1 reverse transcriptase and the p66 subunit polypeptide of HIV-1 reverse transcriptase, thereby indicating that the compound inhibits HIV-1 reverse transcriptase.

This invention provides a method of determining whether a compound enhances formation of a complex between a p66 subunit polypeptide of HIV-1 reverse transcriptase and a p51 subunit polypeptide of HIV-1 reverse transcriptase which comprises:

a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein an increased level of activity of the reporter gene determined in step (a) indicates that the compound is an activator of the formation of the complex between the p51 subunit polypeptide of HIV-1 reverse transcriptase and the p66 subunit polypeptide of HIV-1 reverse transcriptase.

This invention provides a method of determining whether a compound inhibits HIV-1 reverse transcriptase which comprises:

a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the first p66 subunit polypeptide of HIV-1 reverse transcriptase and the second p66 subunit polypeptide of HIV-1 reverse transcriptase, thereby indicating that the compound inhibits HIV-1 reverse transcriptase.

This invention provides a method of determining whether a compound inhibits formation of a complex between a first p66 subunit polypeptide of HIV-1 reverse transcriptase and a second p66 subunit polypeptide of HIV-1 reverse transcriptase which comprises:

a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the first p66 subunit polypeptide of HIV-1 reverse transcriptase and the second p66 subunit polypeptide of HIV-1 reverse transcriptase.

This invention provides a method of determining whether a compound inhibits HIV-1 reverse transcriptase which comprises:

a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein an increased level of activity of the reporter gene in step (a) indicates that the compound is an activator of the formation of the complex between the first p66 subunit polypeptide of HIV-1 reverse transcriptase and the second p66 subunit polypeptide of HIV-1 reverse transcriptase, thereby indicating that the compound inhibits HIV-1 reverse transcriptase.

This invention provides a method of determining whether a compound enhances formation of a complex between a first p66 subunit polypeptide of HIV-1 reverse transcriptase and a second p66 subunit polypeptide of HIV-1 reverse transcriptase which comprises:

a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein an increased level of activity of the reporter gene in step (a) indicates that the compound is an activator of the formation of the complex between the first p66 subunit polypeptide of HIV-1 reverse transcriptase and the second p66 subunit polypeptide of HIV-1 reverse transcriptase, thereby indicating that the compound inhibits HIV-1 reverse transcriptase.

This invention provides a method of making a pharmaceutical composition which comprises:

a) determining whether a compound inhibits HIV-1 reverse transcriptase by one of the methods described herein;

b) recovering the compound if it is determined to inhibit HIV-1 reverse transcriptase; and c) admixing the compound with a pharmaceutically acceptable carrier.

This invention provides a method of inhibiting formation of a complex between the p51 subunit polypeptide of HIV-1 reverse transcriptase and a p66 subunit polypeptide of HIV-1 reverse transcriptase, which comprises contacting either (1) the p51 subunit polypeptide, (2) the p66 subunit polypeptide, or (3) both the p51 subunit polypeptide and the p66 subunit polypeptide, with an effective amount of a compound determined to do so by the method of claim 2, so to thereby inhibit formation of a complex between the p51 subunit polypeptide of HIV-1 reverse transcriptase and a p66 subunit polypeptide of HIV-1 reverse transcriptase.

This invention provides a method of enhancing formation of a complex between the p51 subunit polypeptide of HIV-1 reverse transcriptase and a p66 subunit polypeptide of HIV-1 reverse transcriptase, which comprises contacting either (1) the p51 subunit polypeptide, (2) the p66 subunit polypeptide, or (3) both the p51 subunit polypeptide and the p66 subunit polypeptide, with an effective amount of a compound determined to do so by the method of claim 4, so to thereby enhance formation of a complex between the p51 subunit polypeptide of HIV-1 reverse transcriptase and a p66 subunit polypeptide of HIV-1 reverse transcriptase.

This invention provides a method of inhibiting formation of a complex between a first p66 subunit polypeptide of HIV-1 reverse transcriptase and a second p66 subunit polypeptide of HIV-1 reverse transcriptase, which comprises contacting either (1) the first p66 subunit polypeptide, (2) the second p66 subunit polypeptide, or (3) both the first p66 subunit polypeptide and the second p66 subunit polypeptide, with an effective amount of a compound determined to do so by the method of claim 6, so to thereby inhibit formation of a complex between the first p66 subunit polypeptide of HIV-1 reverse transcriptase and the second p66 subunit polypeptide of HIV-1 reverse transcriptase.

This invention provides a method of enhancing formation of a complex between a first p66 subunit polypeptide of HIV-1 reverse transcriptase and a second p66 subunit polypeptide of HIV-1 reverse transcriptase, which comprises contacting either (1) the first p66 subunit polypeptide, (2) the second p66 subunit polypeptide, or (3) both the first p66 subunit polypeptide and the second p66 subunit polypeptide, with an effective amount of a compound determined to do so by the method of claim 8, so to thereby enhance formation of a complex between the first p66 subunit polypeptide of HIV-1 reverse transcriptase and the second p66 subunit polypeptide of HIV-1 reverse transcriptase.

This invention provides a compound determined to be capable of inhibiting formation of a complex between a p51 subunit polypeptide of HIV-1 reverse transcriptase and a p66 subunit polypeptide of HIV-1 reverse transcriptase.

This invention provides a compound determined to be capable of enhancing formation of a complex between a p51 subunit polypeptide of HIV-1 reverse transcriptase and a p66 subunit polypeptide of HIV-1 reverse transcriptase.

This invention provides a compound determined to be capable of inhibiting formation of a complex between a first p66 subunit polypeptide of HIV-1 reverse transcriptase and a second p66 subunit polypeptide of HIV-1 reverse transcriptase.

This invention provides a compound determined to be capable of enhancing formation of a complex between a first p66 subunit polypeptide of HIV-1 reverse transcriptase and a second p66 subunit polypeptide of HIV-1 reverse transcriptase.

Figure 1:
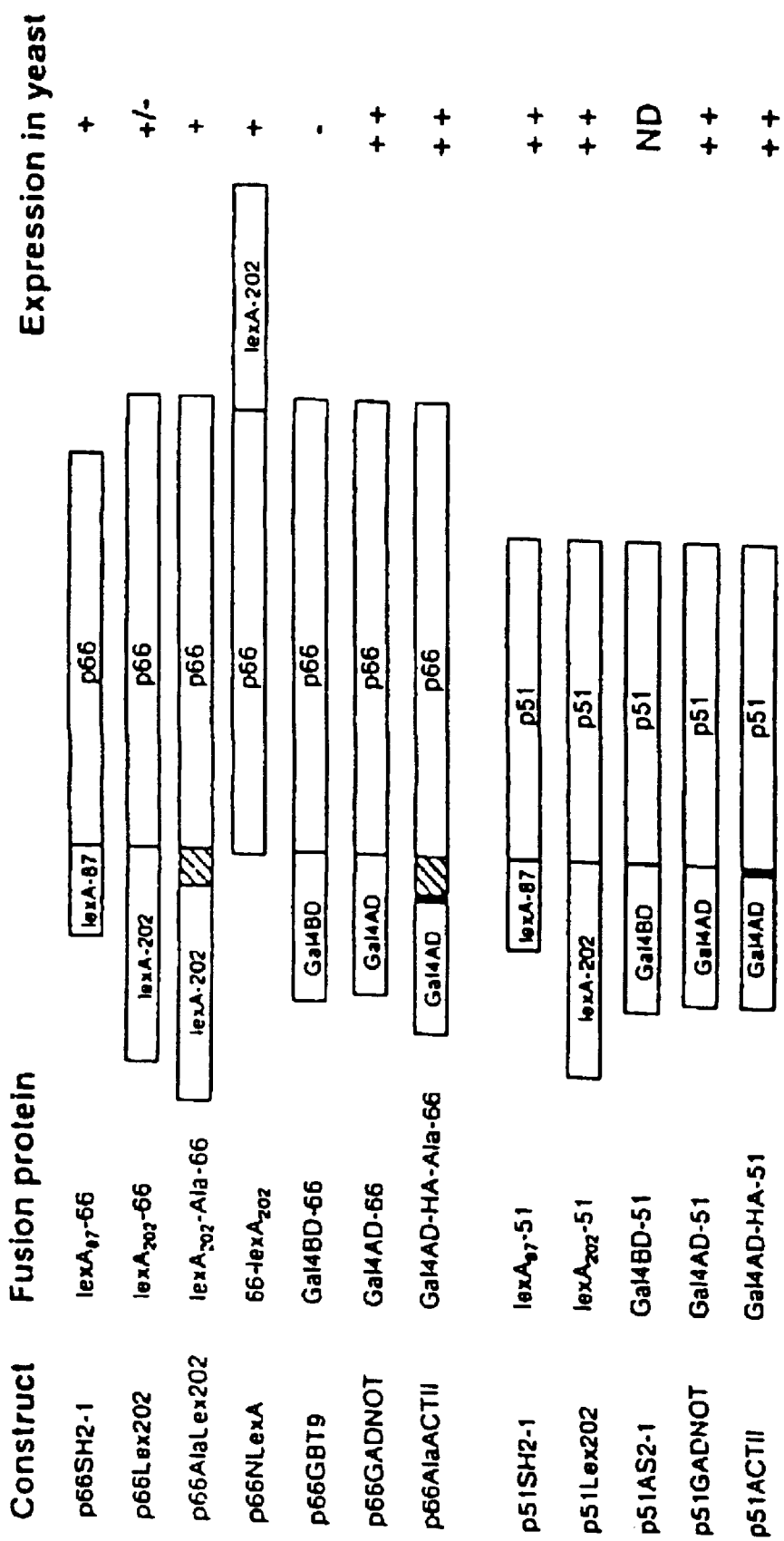
FIG. 1

RT fusion constructs, encoded fusion proteins and expression of fusions in yeast reporter strains. The six-alanine linker is denoted by the hatched box, and the HA epitope by black shaded regions, p66 and p51 indicate the 66 kDa and 51 kDa subunits of HIV-1 RT, respectively. Expression of fusion proteins was determined by introducing the indicated plasmids into CTY10-5d, except for p66 GBT9 and p51AS2-1 which were introduced into HF7c. Fusion protein expression was detected by probing yeast protein lysates with anti-RT antibodies as described in the Materials and Methods. ++, high; +, moderate; +/−, low and −, undetectable protein expression. ND, not done.

FIG. 2

Interaction of p66 deletion mutants with Gal4AD-HA-51 fusion protein, p66 polymerase domains were fused to the C-terminus of lexA87 in pSH2-1. CTY10-5d was cotransformed with the appropriate constructs. Transformants were lifted onto nitrocellulose and subjected to β-gal colony lift assay to determine intensities of blue color produced as defined in Tables 1 and 2. β-gal activity from liquid assays is expressed in Miller Units. Expression in CTY10-5d of p66 fusion proteins was detected using anti-lexA polyclonal antibodies. Expression levels are as defined as in the legend for FIG. 1.

FIG. 3

Interaction of C-terminal deletion mutants of p51 with lexA202-Ala-66, p51 domains were fused to the C-terminus of the Gal4AD in pACTII. Deletions at the C-terminus are denoted by the number of amino acids missing from the end of p51. β-gal activity was determined as described in the legend of FIG. 2. Expression of p51 fusion proteins in CTY10-5d was detected using anti-GAL4AD antibodies, and expression levels are as denoted in the legend for FIG. 1.

FIG. 4

L234A inhibits RT dimerization in the Y2H assay. CTY10-5d was cotransformed with expression constructs, and yeast patches were subjected to both the β-gal colony lift and liquid assays. The green is hydrolyzed X-gal and reflects β-gal activity. p66 wt and p51 wt denote wild-type lex202-Ala-HX66 and Gal4AD-HX51 fusion proteins, respectively. pAD denotes pGADNOT. p66mut and p51mut denote RT fusion proteins lex202-Ala-66-L234A and Gal4AD-51-L234A, respectively.

FIG. 5

Ribbon diagram of unliganded HIV-1 RT showing position of L234A primer grip mutation and locations of suppressors (shaded black). The figure was generated by MOL-SCRIPT (38) and RASTER3D (39) with coordinates (2) retrieved from the Research Collaboratory for Structural Bioinformatics (RCSB) Protein Data Bank (PDB) (http://www.rcsb.org/pdb, PDB ID: lHMV.pdb). Domains are defined as in (3) with fingers, blue; palm, green; thumb, yellow; connection, red; and RNase H in purple. Domains in p66 are in fully saturated colors, whereas in p51 they have decreased saturation. Secondary structure was assigned using DSSP (40). Spirals represent alpha-helices, arrows denote beta-strands.

FIG. 6

In vitro assay for binding of GST-p51 and p66 to form active RT heterodimers. Panel A: Bacterial lysates containing GST-p51 and various p66 proteins as indicated were incubated overnight and captured on glutathione beads. The complexes were eluted, resolved by SDS-PAGE, blotted to membrane and detected by monoclonal anti-RT antibodies. Mock, GST-p51 alone. Panel B: An aliquot of each incubation mix, reflecting input protein, was directly analyzed by SDS-PAGE and Western blot as in Panel A. Panel C: Bound proteins were eluted with glutathione and assayed for RT activity with homopolymeric template-primer. Values are normalized to the wild-type control.

FIG. 7

Dose-response curve showing the enhancement by NNR-TIs of b-gal activity in yeast cotransformed with lexA$_{87}$-66 and Gal4AD-51. The fold increase in b-gal activity was calculated by dividing b-gal activity (in Miller Units) for each drug concentration with the b-gal activity from cells grown in the absence of inhibitor. The data represents the average results from two independent experiments. The concentration of drug that mediates a 5-fold increase in b-gal activity is shown in parenthesis. A: b-gal enhancement activity of the NNRTIs, efavirenz, HBY 097, a-APA, nevirapine, 8-Cl-TIBO and delavirdine. B: b-gal enhancement activity of the carboxanilide class of NNRTIs.

FIG. 8

Effect of the Y181C mutation on enhancement of b-gal activity in yeast by nevirapine. Yeast expressing wild-type lexA$_{87}$-66 and Gal4AD-51 or mutant lexA$_{87}$-66Y181C and wild type Gal4AD-51 were grown in the presence of nevirapine and assayed for b-gal activity. Results are expressed as fold increase in b-gal activity compared to untreated cells. Values on top of each bar indicates b-gal activity (in Miller Units) +/−standard deviation.

FIG. 9

Effect of efavirenz on b-gal activity in yeast expressing the dimerization defective mutants L234A and W401A. Yeast expressing wild-type p66 bait and p51 prey fusions, mutant p66 bait and wild-type p51 prey and mutant p66 bait and mutant p51 prey fusions were assayed for b-gal activity. Results are expressed as the fold increase in b-gal activity compared to untreated controls. Values on top of each bar indicates b-gal activity in Miller Units. Effect of efavirenz on yeast expressing bait and prey fusions with the W401A change (A) or L234A change (B).

FIG. 10

Coimmunoprecipitaton assay detecting heterodimer formation in yeast propagated in the presence of NNRTIs. (A): Yeast expressing p66 bait and p51 prey fusions containing the W401A mutation were grown in the presence of efavirenz (EFV), UC781 or no drug. After growth, yeast were processed in the absence or presence of added drug (drug in ip). Heterodimers present in lysates were detected by immunoprecipation of Gal4AD-HA-51W401A with anti-HA antibodies followed by immunodetection of coimmunoprecipitated p66. The b-gal activity for each treatment was determined and expressed in Miller Units. (B). Yeast expressing p66 bait and p51 prey fusions containing the L234A mutation.

FIG. 11

Western blot analysis of HIV-1 RT heterodimers formed in the presence of efavirenz (EFV) in vitro. Bacteria expressing either wild-type p66-His and GST-p51, or dimerization defective mutants were induced and lysates were prepared. Lysates were mixed and incubated overnight at 4° C. with or without drug and dimers were captured by binding to Glutathione Sepharose 4B beads. Heterodimer bound to beads were resolved by SDS-PAGE and proteins detected by probing with anti-RT monoclonal antibodies.

FIG. 12

Western blot analysis of HIV-1 RT heterodimers formed in the presence of NNRTIs in vitro. Bacterially expressed proteins p66-His and GST-p51 were combined in the presence of 1–1000 fold molar excess of drug and incubated overnight. Heterodimers were captured and detected as described in the legend of FIG. 11.

FIG. 13

Western blot analysis of heterodimer formation after pretreatment of one of the subunits with efavirenz. p66-His, GST-p51 and M15 bacterial lysate were preincubated in the absence or presence of 10–1000 fold molar excess of efavirenz. Lysates were washed and the presence of residual efavirenz was assayed by the addition of GST-p51, p66-His or both subunits, respectively. Heterodimers were captured and detected as described in the legend of FIG. 11.

FIG. 14

Molecular surface representation of the p66 and p51 subunits of HIV-1 RT. Residues colored yellow (p66) or magenta (p51) are amino acids that are not accessible to solvent in the presence of the other subunit in the heterodimeric form. The NNRTI binding pocket is shown in red. The sum of the surface areas colored in yellow and magenta is the total buried surface area at the interface of the two subunits.

FIG. 15

Binding of delavirdine (BHAP) (A) and UC781 (B) at the interface of the p66 (magenta) and p51 (yellow) subunits of the HIV-1 RT. Delavirdine, a large inhibitor, is bound further away from the p66/p51 interface. The relative orientation of the inhibitors in the NNRTI binding pocket is shown in (C). Some residues that comprise the NNRTI binding site have been omitted for clarity.

DETAILED DESCRIPTION OF THE INVENTION

This invention provides a method of determining whether a compound inhibits HIV-1 reverse transcriptase which comprises:
a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and
b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the p51 subunit polypeptide of HIV-1 reverse transcriptase and the p66 subunit polypeptide of HIV-1 reverse transcriptase, thereby indicating that the compound inhibits HIV-1 reverse transcriptase.

This invention provides a method of determining whether a compound inhibits formation of a complex between a p66 subunit polypeptide of HIV-1 reverse transcriptase and a p51 subunit polypeptide of HIV-1 reverse transcriptase which comprises:
a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and
b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the p51 subunit polypeptide of HIV-1 reverse transcriptase and the p66 subunit polypeptide of HIV-1 reverse transcriptase.

This invention provides a method of determining whether a compound inhibits HIV-1 reverse transcriptase which comprises:
a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and
b) comparing the level of activity of the reporter gene determined in step (a) with a level of activity of the reporter gene determined in the absence of the compound, wherein an increased level of activity of the reporter gene determined in step (a) indicates that the compound is an activator of the formation of the complex between the p51 subunit polypeptide of HIV-1 reverse transcriptase and the p66 subunit polypeptide of HIV-1 reverse transcriptase, thereby indicating that the compound inhibits HIV-1 reverse transcriptase.

This invention provides a method of determining whether a compound enhances formation of a complex between a p66 subunit polypeptide of HIV-1 reverse transcriptase and a p51 subunit polypeptide of HIV-1 reverse transcriptase which comprises:
a) contacting a yeast cell with the compound, which cell comprises (i) a first plasmid which expresses a fusion protein comprising a p66 subunit polypeptide of HIV-1 reverse transcriptase, (ii) a second plasmid which expresses a fusion protein comprising a p51 subunit polypeptide of HIV-1 reverse transcriptase, and (iii) a reporter gene which is activated in the presence of a complex between the p66 subunit polypeptide and the p51 subunit polypeptide, and determining the level of activity of the reporter gene in the cell in the presence of the compound; and
b) comparing the level of activity of the reporter gene determined in step (a) with a level of activity of the reporter gene determined in the absence of the compound, wherein an increased level of activity of the reporter gene determined in step (a) indicates that the compound is an activator of the formation of the complex between the p51 subunit polypeptide of HIV-1 reverse transcriptase and the p66 subunit polypeptide of HIV-1 reverse transcriptase.

This invention provides a method of determining whether a compound inhibits HIV-1 reverse transcriptase which comprises:
a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and
b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the first p66 subunit polypeptide of HIV-1 reverse transcriptase and the second p66 subunit polypeptide of HIV-1 reverse transcriptase, thereby indicating that the compound inhibits HIV-1 reverse transcriptase.

This invention provides a method of determining whether a compound inhibits formation of a complex between a first p66 subunit polypeptide of HIV-1 reverse transcriptase and a second p66 subunit polypeptide of HIV-1 reverse transcriptase which comprises:
a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein a decreased level of activity of the reporter gene in step (a) indicates that the compound inhibits formation of a complex between the first p66 subunit polypeptide of HIV-1 reverse transcriptase and the second p66 subunit polypeptide of HIV-1 reverse transcriptase.

This invention provides a method of determining whether a compound inhibits HIV-1 reverse transcriptase which comprises:

a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein an increased level of activity of the reporter gene in step (a) indicates that the compound is an activator of the formation of the complex between the first p66 subunit polypeptide of HIV-1 reverse transcriptase and the second p66 subunit polypeptide of HIV-1 reverse transcriptase, thereby indicating that the compound inhibits HIV-1 reverse transcriptase.

This invention provides a method of determining whether a compound enhances formation of a complex between a first p66 subunit polypeptide of HIV-1 reverse transcriptase and a second p66 subunit polypeptide of HIV-1 reverse transcriptase which comprises:

a) contacting a yeast cell with the compound, which cell comprises (i) a first plasmid which expresses a fusion protein comprising a first p66 subunit polypeptide of HIV-1 reverse transcriptase, (ii) a second plasmid which expresses a fusion protein comprising a second p66 subunit polypeptide of HIV-1 reverse transcriptase, and (iii) a reporter gene which is activated in the presence of a complex between the first p66 subunit polypeptide and the second p66 subunit polypeptide, and determining the level of activity of the reporter gene in the cell in the presence of the compound; and b) comparing the level of activity of the reporter gene determined in step (a) with a level of activity of the reporter gene determined in the absence of the compound, wherein an increased level of activity of the reporter gene in step (a) indicates that the compound is an activator of the formation of the complex between the first p66 subunit polypeptide of HIV-1 reverse transcriptase and the second p66 subunit polypeptide of HIV-1 reverse transcriptase, thereby indicating that the compound inhibits HIV-1 reverse transcriptase.

The methods described herein may also be adapted to other types of cells in addition to a yeast cell. Other cell types include but are not limited to eucaryotic, procaryotic, bacteria, *E. coli*, mammalian and human cells.

In one embodiment of the methods described herein, (a) the fusion protein expressed by the first plasmid comprises a peptide having a DNA binding domain, and (b) the fusion protein expressed by the second plasmid comprises a peptide having a transcription activation domain.

In one embodiment of the methods described herein, (a) the fusion protein expressed by the first plasmid comprises a peptide having a transcription activation domain, and (b) the fusion protein expressed by the second plasmid comprises a peptide having a DNA binding domain.

In one embodiment of the fusion proteins described herein, the peptide having a DNA binding domain is N-terminal relative to the p66 or p51 subunit polypeptide. In another embodiment, the peptide having a DNA binding domain is C-terminal relative to the 51 or p66 subunit polypeptide. The peptide having a DNA binding domain may be bound in the fusion protein to the p51 or p66 subunit polypeptides. In one embodiment, they are bound by peptide bonds. Alternatively, the fusion protein may also comprise one or more additional components, such as a peptide linker and/or an epitope tag. These additional components may separate the peptides from the p51 or p66 subunit polypeptide. The various components may be bound to each other by peptide bonds.

In one embodiment of the fusion proteins described herein, the peptide having a transcription activation domain is N-terminal relative to the p66 or p51 subunit polypeptide. In another embodiment, the peptide having a transcription activation domain is C-terminal relative to the 51 or p66 subunit polypeptide. The peptide having a transcription activation domain may be bound in the fusion protein to the p51 or p66 subunit polypeptides. In one embodiment, they are bound by peptide bonds. Alternatively, the fusion protein may also comprise one or more additional components, such as a peptide linker and/or an epitope tag. These additional components may separate the peptides from the p51 or p66 subunit polypeptide. The various components may be bound to each other by peptide bonds.

The invention described herein may employ p51 and p66 subunits from among various HIV-1 strains. One may use the reverse transcriptase coding regions for p66 and p51 from any HIV-1 strain. For example, in the HIV-1 NL4-3 strain, the amino acid and nucleic acid sequences of which may be found in a pNL4-3 clone deposited at Genbank Accession No. M19921. The p51 and p66 subunits share the same N-terminal sequence, whereas p51 does not have the C-terminal ribonuclease H region. Accordingly, p66 corresponds to codons 1–560 and p51 corresponds to codons 1–440 in the RT gene.

The invention may employ other HIV-1 strains such as the following: $HIVE_{HXB2G}$ (Genbank Accession No. K03455), $HIV_{BRUCG}$ (Genbank Accession No. K02013), $HIV_{MNCG}$ (Genbank Accession No. M17449), $HIV_{NY5CG}$ (Genbank Accession No. M38431); $HIV_{JRCSF}$ (Genbank Accession No.M38429), and $HIV_{SF2CG}$ (Genbank Accession No. K02007).

In one embodiment of the fusion proteins described herein, the DNA binding domain is a LexA DNA binding domain. The amino acid and nucleic acid sequences for LexA may be found at Genbank Accession No. J01643. In one embodiment of the methods described herein, the peptide having a DNA binding domain comprises LexA amino acid residues 1–87. The portion of LexA which corresponds to amino acid residues 1–87 may comprise a LexA DNA binding domain. In one embodiment of the methods described herein, the peptide having a DNA binding domain comprises LexA amino acid residues 1–202. The portion of LexA which corresponds to amino acid residues 1–202 may comprise a LexA DNA binding domain.

In one embodiment of the fusion proteins described herein, the DNA binding domain is a GAL4 DNA binding domain. The amino acid and nucleic acid sequences for Gal4 may be found at Genbank Accession No. K01486.

In one embodiment of the fusion proteins described herein, the transcription activation domain is a GAL4 transcription activation domain. In one embodiment, the peptide having a transcription activation domain comprises GAL4 amino acid residues 768–881. The portion of Gal4 which corresponds to amino acid residues 768–881 may comprise a Gal4 activation domain.

In one embodiment of the fusion proteins described herein, the transcription activation domain is a VP16 transcription activation domain. The amino acid and nucleic acid sequences for VP16 may be found at Genbank Accession No. U89963.

In one embodiment of the fusion proteins described herein, the fusion protein expressed by the first plasmid, the second plasmid or both plasmids comprises a peptide comprising consecutive alanine residues. The above described peptide comprising consecutive alanine residues may be referred to as an alanine linker. Such linker sequence may be a series of consecutive amino acid residues other than alanine. Such linker sequence may be of various lengths. For example, the linker may comprise 2 amino acids, 3 amino acids, 4 amino acids, 5 amino acids, 6 amino acids, 7 amino acids, 8 amino acids, 9 amino acids or 10 amino acids. The peptide linker may also be of longer lengths, for example, from about 10 amino acids to about 20 amino acids. In one embodiment, the peptide comprising consecutive alanine residues comprises at least 6 alanine residues.

As used herein, the following standard abbreviations are used throughout the specification to indicate specific amino acids: A=ala=alanine; R=arg=arginine; N=asn=asparagine; D=asp=aspartic acid; C=cys=cysteine; Q=gln=glutamine; E=glu=glutamic acid; G=gly=glycine; H=his=histidine; I=ile=isoleucine; L=leu=leucine; K=lys=lysine; M=met= methionine; F=phe=phenylalanine; P=pro=proline; S=ser= serine; T=thr=threonine; W=trp=tryptophan; Y=tyr= tyrosine; V=val=valine; B=asx=asparagine or aspartic acid; Z=glx=glutamine or glutamic acid.

As used herein, the following standard abbreviations are used throughout the specification to indicate specific nucleotides: C=cytosine; A=adenosine; T=thymidine; G=guanosine; and U=uracil.

In one embodiment of the fusion proteins described herein, the fusion protein comprises an influenza hemagglutinin (HA) epitope tag. The sequence for influenza hemagglutinin (HA) epitope may be found in Genbank Accession No. U29899 at nucleotide bases 5042–5068 within the plasmid pACT2. The invention may also comprise other types of epitope tags known to one skilled in the art.

In one embodiment of the fusion proteins described herein, the reporter gene is a LacZ reporter gene. The amino acid and nucleic acid sequences for LacZ may be found at Genbank Accession no. U89671.

In one embodiment of the methods described herein, (a) the fusion protein expressed by the first plasmid comprises a peptide comprising a LexA protein DNA binding domain, wherein the p66 subunit polypeptide is bound at its C-terminal amino acid to the N-terminal amino acid of the peptide comprising a LexA protein DNA binding domain; and (b) the fusion protein expressed by the second plasmid comprises a Gal4 peptide corresponding to amino acids 768–881 of Gal4, and an influenza hemagglutinin (HA) epitope tag, which Gal4 peptide is bound at its C-terminal amino acid to the N-terminal amino acid of the influenza hemagglutinin (HA) epitope tag, which influenza hemagglutinin (HA) epitope tag is bound at its C-terminal amino acid to the N-terminal amino acid of the p51 subunit polypeptide.

In the fusion proteins described herein, the location of the various components relative to each other may be varied. For example, in the embodiment described above, the peptide comprising a LexA protein DNA binding domain may alternatively be bound at its C-terminal amino acid to the N-terminal amino acid of the p66 subunit polypeptide. The p51 subunit polypeptide may be N-terminal to the Gal4 peptide. One skilled in art would know how to make and use the various vectors and plasmids described herein.

In one embodiment of the methods described herein, (a) the fusion protein expressed by the first plasmid comprises a peptide comprising a LexA protein DNA binding domain, wherein the p66 subunit polypeptide is bound at it's C-terminal amino acid to the N-terminal amino acid of the peptide comprising a LexA protein DNA binding domain; and (b) the fusion protein expressed by the second plasmid comprises a Gal4 peptide corresponding to amino acids 768–881 of Gal4, which Gal4 peptide is bound at its C-terminal amino acid to the N-terminal amino acid of the p51 subunit polypeptide.

In one embodiment of the methods described herein, (a) the fusion protein expressed by the first plasmid comprises a LexA peptide corresponding to amino acid residues 1–87, wherein the LexA peptide is bound at its C-terminal amino acid to the N-terminal amino acid of the of the p66 subunit polypeptide; and (b) the fusion protein expressed by the second plasmid comprises a Gal4 peptide corresponding to amino acids 768–881 of Gal4, and an influenza hemagglutinin (HA) epitope tag, which Gal4 peptide is bound at its C-terminal amino acid to the N-terminal amino acid of the influenza hemagglutinin (HA) epitope tag, which influenza hemagglutinin (HA) epitope tag is bound at its C-terminal amino acid to the N-terminal amino acid of the p51 subunit polypeptide.

In one embodiment of the methods described herein, (a) the fusion protein expressed by the first plasmid comprises a LexA peptide corresponding to amino acid residues 1–87, wherein the LexA peptide is bound at its C-terminal amino acid to the N-terminal amino acid of the of the p66 subunit polypeptide; and (b) the fusion protein expressed by the second plasmid comprises a Gal4 peptide corresponding to amino acids 768–881 of Gal4, which Gal4 peptide is bound at its C-terminal amino acid to the N-terminal amino acid of the p51 subunit polypeptide.

In one embodiment of the methods described herein, (a) the fusion protein expressed by the first plasmid comprises a LexA peptide corresponding to amino acid residues 1–202, and a peptide comprising six consecutive alanine residues, wherein the LexA peptide is bound at its C-terminal amino acid to the N-terminal amino acid of the peptide comprising six consecutive alanine residues, wherein the peptide comprising six consecutive alanine residues is bound at its C-terminal amino acid to the N-terminal amino acid of the p66 subunit polypeptide; and (b) the fusion protein expressed by the second plasmid comprises a Gal4 peptide corresponding to amino acids 768–881 of Gal4, which Gal4 peptide is bound at its C-terminal amino acid to the N-terminal amino acid of the p51 subunit polypeptide.

In one embodiment of the methods described herein, (a) the fusion protein expressed by the first plasmid comprises a LexA peptide corresponding to amino acid residues 1–202, and a peptide comprising six consecutive alanine residues, wherein the LexA peptide is bound at its C-terminal amino acid to the N-terminal amino acid of the peptide comprising six consecutive alanine residues, wherein the peptide comprising six consecutive alanine residues is bound at its C-terminal amino acid to the N-terminal amino acid of the p66 subunit polypeptide; and (b) the fusion protein expressed by the second plasmid comprises a Gal4 peptide corresponding to amino acids 768–881 of Gal4, and an influenza hemagglutinin (HA) epitope tag, which Gal4 peptide is bound at its C-terminal amino acid to the N-terminal amino acid of the influenza hemagglutinin (HA) epitope tag, which influenza hemagglutinin (HA) epitope tag is bound at its C-terminal amino acid to the N-terminal amino acid of the p51 subunit polypeptide.

In one embodiment of the methods described herein, (a) the fusion protein expressed by the first plasmid comprises a Gal4 peptide corresponding to amino acids 768–881 of Gal4, an influenza hemagglutinin (HA) epitope tag, and a peptide comprising six consecutive alanine residues, wherein the Gal4 peptide is bound at its C-terminal amino acid to the N-terminal amino acid of the influenza hemagglutinin (HA) epitope tag, wherein the influenza hemagglutinin (HA) epitope tag is bound at its C-terminal amino acid to the N-terminal amino acid of the peptide comprising six consecutive alanine residues, wherein the peptide comprising six consecutive alanine residues is bound at its C-terminal amino acid to the N-terminal amino acid of the p66 subunit polypeptide; and (b) the fusion protein expressed by second plasmid comprises a peptide comprising a LexA protein DNA binding domain, wherein the p51 subunit polypeptide is bound at its C-terminal amino acid to the N-terminal amino acid of the peptide comprising a LexA protein DNA binding domain.

In one embodiment of the methods described herein, (a) the fusion protein expressed by the first plasmid comprises a Gal4 peptide corresponding to amino acids 768–881 of Gal4, an influenza hemagglutinin (HA) epitope tag, and a peptide comprising six consecutive alanine residues, wherein the Gal4 peptide is bound at its C-terminal amino acid to the N-terminal amino acid of the influenza hemagglutinin (HA) epitope tag, wherein the influenza hemagglutinin (HA) epitope tag is bound at its C-terminal amino acid to the N-terminal amino acid of the peptide comprising six consecutive alanine residues, wherein the peptide comprising six consecutive alanine residues is bound at its C-terminal amino acid to the N-terminal amino acid of the p66 subunit polypeptide; and (b) the fusion protein expressed by second plasmid comprises a peptide comprising a LexA protein DNA binding domain, wherein peptide comprising a LexA protein DNA binding domain is bound at its C-terminal amino acid to the N-terminal amino acid of the p51 subunit polypeptide.

In one embodiment of the methods described herein, (a) the fusion protein expressed by the first plasmid comprises a Gal4 peptide corresponding to amino acids 768–881 of Gal4, an influenza hemagglutinin (HA) epitope tag, and a peptide comprising six consecutive alanine residues, wherein the Gal4 peptide is bound at its C-terminal amino acid to the N-terminal amino acid of the influenza hemagglutinin (HA) epitope tag, wherein the influenza hemagglutinin (HA) epitope tag is bound at its C-terminal amino acid to the N-terminal amino acid of the peptide comprising six consecutive alanine residues, wherein the peptide comprising six consecutive alanine residues is bound at its C-terminal amino acid to the N-terminal amino acid of the p66 subunit polypeptide; and (b) the fusion protein expressed by second plasmid comprises a peptide comprising a Gal4 protein DNA binding domain, which peptide comprising a Gal4 protein DNA binding domain is bound at its C-terminal amino acid to the N-terminal amino acid of the p51 subunit polypeptide.

In one embodiment of the methods described herein, (a) the fusion protein expressed by the first plasmid comprises a Gal4 peptide corresponding to amino acids 768–881 of Gal4, wherein the Gal4 peptide is bound at its C-terminal amino acid to the N-terminal amino acid of the p66 subunit polypeptide; and (b) the fusion protein expressed by second plasmid comprises a peptide comprising a LexA protein DNA binding domain, wherein the p51 subunit polypeptide is bound at its C-terminal amino acid to the N-terminal amino acid of the peptide comprising a LexA protein DNA binding domain.

In one embodiment of the methods described herein, (a) the fusion protein expressed by the first plasmid comprises a Gal4 peptide corresponding to amino acids 768–881 of Gal4, wherein the Gal4 peptide is bound at its C-terminal amino acid to the N-terminal amino acid of the p66 subunit polypeptide; and (b) the fusion protein expressed by second plasmid comprises a peptide comprising a LexA protein DNA binding domain, which peptide comprising a LexA protein DNA binding domain is bound at its C-terminal amino acid to the N-terminal amino acid of the p51 subunit polypeptide.

In one embodiment of the methods described herein, (a) the fusion protein expressed by the first plasmid comprises a Gal4 peptide corresponding to amino acids 768–881 of Gal4, wherein the Gal4 peptide is bound at its C-terminal amino acid to the N-terminal amino acid of the p66 subunit polypeptide; and (b) the fusion protein expressed by second plasmid comprises a peptide comprising a Gal4 protein DNA binding domain, which peptide comprising a Gal4 protein DNA binding domain is bound at its C-terminal amino acid to the N-terminal amino acid of the p51 subunit polypeptide.

In one embodiment of the methods described herein, (a) the fusion protein expressed by the first plasmid comprises a peptide comprising a LexA protein DNA binding domain, wherein the p66 subunit polypeptide is bound at it's C-terminal amino acid to the N-terminal amino acid of the peptide comprising a LexA protein DNA binding domain; and (b) the fusion protein expressed by the second plasmid comprises a Gal4 peptide corresponding to amino acids 768–881 of Gal4, an influenza hemagglutinin (HA) epitope tag, and a peptide comprising six consecutive alanine residues, wherein the Gal4 peptide is bound at its C-terminal amino acid to the N-terminal amino acid of the influenza hemagglutinin (HA) epitope tag, wherein the influenza hemagglutinin (HA) epitope tag is bound at its C-terminal amino acid to the N-terminal amino acid of the peptide comprising six consecutive alanine residues, wherein the peptide comprising six consecutive alanine residues is bound at its C-terminal amino acid to the N-terminal amino acid of the p66 subunit polypeptide.

This invention provides a method of making a pharmaceutical composition which comprises:
a) determining whether a compound inhibits HIV-1 reverse transcriptase by one of the methods described herein;
b) recovering the compound if it is determined to inhibit HIV-1 reverse transcriptase; and
c) admixing the compound with a pharmaceutically acceptable carrier.

As used herein, "inhibits" means that the amount is reduced as compared with the amount that would occur in a control sample without the compound. As used herein "enhanced" means that the amount is increased compared with the amount that would occur in a control sample without the compound.

As used herein, the term "compound" includes both protein and non-protein moieties. In one embodiment, the compound is a small molecule. In another embodiment, the compound is a protein. The protein may be, by way of example, an antibody directed against a portion of a p51 or p66 subunit. The agent may be derived from a library of low molecular weight compounds or a library of extracts from plants or other organisms. In an embodiment, the agent is known. In a separate embodiment, the agent is not previously known. The agents of the subject invention include but are not limited to compounds or molecular entities such as peptides, polypeptides, and other organic or inorganic molecules and combinations thereof In one embodiment of the methods described herein, the compound is an antibody or a portion of an antibody. In one embodiment of the antibody, the antibody is a monoclonal antibody. In one embodiment of the antibody, the antibody is a polyclonal antibody. In one embodiment of the antibody, the antibody is a humanized antibody. In one embodiment of the antibody, the antibody is a chimeric antibody. The portion of the antibody may comprise a light chain of the antibody. The portion of the antibody may comprise a heavy chain of the antibody. The portion of the antibody may comprise a Fab portion of the antibody. The portion of the antibody may comprise a F(ab')$_2$ portion of the antibody. The portion of the antibody may comprise a Fd portion of the antibody. The portion of the antibody may comprise a Fv portion of the antibody. The portion of the antibody may comprise a variable domain of the antibody. The portion of the antibody may comprise one or more CDR domains of the antibody.

In one embodiment of the methods described herein, the compound is a polypeptide. In one embodiment of the methods described herein, the compound is a oligopeptide. In one embodiment of the methods described herein, the compound is a nonpeptidyl agent. In one embodiment, the nonpeptidyl agent is a compound having a molecular weight less than 500 daltons.

In one embodiment of the methods described herein, the reverse HIV-1 transcriptase enzyme or its p51 and p66 subunits is present in a subject and the contacting is effected by administering the compound to the subject. Accordingly, the subject invention has various applications which includes HIV treatment such as treating a subject who has become afflicted with HIV. As used herein, "afflicted with HIV" means that the subject has at least one cell which has been infected by HIV. As used herein, "treating" means either slowing, stopping or reversing the progression of an HIV disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV. Another application of the subject invention is to prevent a subject from contracting HIV. As used herein, "contracting HIV" means becoming infected with HIV, whose genetic information replicates in and/or incorporates into the host cells. Another application of the subject invention is to treat a subject who has become infected with HIV. As used herein, "HIV infection" means the introduction of HIV genetic information into a target cell, such as by fusion of the target cell membrane with HIV or an HIV envelope glycoprotein$^+$ cell. The target cell may be a bodily cell of a subject. In the preferred embodiment, the target cell is a bodily cell from a human subject. Another application of the subject invention is to inhibit HIV infection. As used herein, "inhibiting HIV infection" means reducing the amount of HIV genetic information introduced into a target cell population as compared to the amount that would be introduced without said composition.

This invention provides a method of treating a subject afflicted with HIV which comprises administering to the subject an effective dose of an agent of composition described herein. In one embodiment, the agent or composition may be enough to decrease the subject's viral load. As used herein, "treating" means either slowing, stopping or reversing the progression of an HIV disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV. As used herein, "afflicted with HIV" means that the subject has at least one cell which has been infected by HIV.

This invention provides a method of preventing a subject from contracting HIV which comprises administering to the subject an effective dose of an agent or composition described herein.

The dose of the agent or composition of the invention will vary depending on the subject and upon the particular route of administration used. Dosages can range from 0.1 to 100,000 µg/kg. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

As used herein, "effective dose" means an amount in sufficient quantities to either treat the subject or prevent the subject from becoming HIV infected. A person of ordinary skill in the art can perform simple titration experiments to determine what amount is required to treat the subject. As used herein, "contracting HIV" means becoming infected with HIV, whose genetic information replicates in and/or incorporates into the host cells. In one embodiment, the effective amount of the agent or composition comprises from about 0.000001 mg/kg body weight to about 100 mg/kg body weight of the subject.

As used herein, "subject" means any animal or artificially modified animal capable of becoming HIV-infected. The subjects include but are mot limited to a human being, a primate, an equine, an opine, an avian, a bovine, a porcine, a canine, a feline or a mouse. Artificially modified animals include, but are not limited to, SCID mice with human immune systems. The animals include but are not limited to mice, rats, dogs, guinea pigs, ferrets, rabbits, and primates. In the preferred embodiment, the subject is a human being. The subject may be an "HIV-infected subject" which is a subject having at least one of his or her own cells invaded by HIV. In the preferred embodiment, the HIV infected subject is a human being. The subject may be a "non-HIV-infected subject" which is a subject not having any of his own cells invaded by HIV. In the preferred embodiment, the non-HIV infected subject is a human being.

As used herein, "administering" may be effected or performed using any of the methods known to one skilled in the art, which includes intralesional, intraperitoneal, intramuscular, subcutaneous, intravenous, liposome mediated delivery, transmucosal, intestinal, topical, nasal, oral, anal, ocular or otic delivery.

In one embodiment, amount of the compound administered is between about 1 mg and about 50 mg per kg body weight of the subject. In one embodiment, amount of the compound administered is between about 2 mg and about 40 mg per kg body weight of the subject. In one embodiment, amount of the compound administered is between about 3 mg and about 30 mg per kg body weight of the subject. In one embodiment, the amount of the compound administered is between about 4 mg and about 20 mg per kg body weight of the subject. In one embodiment, amount of the compound administered is between about 5 mg and about 10 mg per kg body weight of the subject.

In one embodiment of the methods described herein, the compound is administered at least once per day. In one embodiment of the methods described herein, the agent is administered daily. In one embodiment of the methods described herein, the agent is administered every other day. In one embodiment of the methods described herein, the agent is administered every 6 to 8 days. In one embodiment of the methods described herein, the agent is administered weekly.

This invention provides a method of inhibiting formation of a complex between the p51 subunit polypeptide of HIV-1 reverse transcriptase and a p66 subunit polypeptide of HIV-1 reverse transcriptase, which comprises contacting either (1) the p51 subunit polypeptide, (2) the p66 subunit polypeptide, or (3) both the p51 subunit polypeptide and the p66 subunit polypeptide, with an effective amount of a compound determined to do so by the method of claim 2, so to thereby inhibit formation of a complex between the p51 subunit polypeptide of HIV-1 reverse transcriptase and a p66 subunit polypeptide of HIV-1 reverse transcriptase.

This invention provides a method of enhancing formation of a complex between the p51 subunit polypeptide of HIV-1 reverse transcriptase and a p66 subunit polypeptide of HIV-1 reverse transcriptase, which comprises contacting either (1) the p51 subunit polypeptide, (2) the p66 subunit polypeptide, or (3) both the p51 subunit polypeptide and the p66 subunit polypeptide, with an effective amount of a compound determined to do so by the method of claim 4, so to thereby enhance formation of a complex between the p51 subunit polypeptide of HIV-1 reverse transcriptase and a p66 subunit polypeptide of HIV-1 reverse transcriptase.

This invention provides a method of inhibiting formation of a complex between a first p66 subunit polypeptide of HIV-1 reverse transcriptase and a second p66 subunit polypeptide of HIV-1 reverse transcriptase, which comprises contacting either (1) the first p66 subunit polypeptide, (2) the second p66 subunit polypeptide, or (3) both the first p66 subunit polypeptide and the second p66 subunit polypeptide, with an effective amount of a compound determined to do so by the method of claim 6, so to thereby inhibit formation of a complex between the first p66 subunit polypeptide of HIV-1 reverse transcriptase and the second p66 subunit polypeptide of HIV-1 reverse transcriptase.

This invention provides a method of enhancing formation of a complex between a first p66 subunit polypeptide of HIV-1 reverse transcriptase and a second p66 subunit polypeptide of HIV-1 reverse transcriptase, which comprises contacting either (1) the first p66 subunit polypeptide, (2) the second p66 subunit polypeptide, or (3) both the first p66 subunit polypeptide and the second p66 subunit polypeptide, with an effective amount of a compound determined to do so by the method of claim 8, so to thereby enhance formation of a complex between the first p66 subunit polypeptide of HIV-1 reverse transcriptase and the second p66 subunit polypeptide of HIV-1 reverse transcriptase.

In one embodiment of the above methods, the HIV-1 reverse transcriptase is present in a subject and the contacting is effected by administering the compound to the subject. The compound may be administered by various routes known to one skilled in the art including but not limited to those wherein the compound is administered orally, intravenously, subcutaneously, intramuscularly, topically or by liposome-mediated delivery. The subject may be any subject including but not limited to a human being, a primate, an equine, an opine, an avian, a bovine, a porcine, a canine, a feline or a mouse. In one embodiment, the compound is administered at least once per day. In one embodiment, the compound is administered daily. In one embodiment, the compound is administered every other day. In one embodiment, compound is administered every 6 to 8 days. In one embodiment, the compound is administered weekly.

This invention provides a compound determined to be capable of inhibiting formation of a complex between a p51 subunit polypeptide of HIV-1 reverse transcriptase and a p66 subunit polypeptide of HIV-1 reverse transcriptase.

This invention provides a compound determined to be capable of enhancing formation of a complex between a p51 subunit polypeptide of HIV-1 reverse transcriptase and a p66 subunit polypeptide of HIV-1 reverse transcriptase.

This invention provides a compound determined to be capable of inhibiting formation of a complex between a first p66 subunit polypeptide of HIV-1 reverse transcriptase and a second p66 subunit polypeptide of HIV-1 reverse transcriptase.

This invention provides a compound determined to be capable of enhancing formation of a complex between a first p66 subunit polypeptide of HIV-1 reverse transcriptase and a second p66 subunit polypeptide of HIV-1 reverse transcriptase.

This invention provides a composition which comprises one of the compounds described herein and a carrier. As used herein, "composition" means a mixture. The compositions include but are not limited to those suitable for oral, rectal, intravaginal, topical, nasal, opthalmic, or parenteral, intravenous, subcutaneous, intramuscular, and intraperitoneal administration to a subject. As used herein, "parenteral" includes but is not limited to subcutaneous, intravenous, intramuscular, or intrasternal injections or infusion techniques.

This invention provides an agent or composition described herein and a carrier. Such carrier may be one that is a pharmaceutically acceptable carrier. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

In one embodiment of the agents described herein, the compound is an antibody or portion of an antibody. As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. optionally, an antibody can be labeled with a detectable marker. Detectable markers include, for example, radioactive or fluorescent markers. The antibody may be a human or nonhuman antibody. The nonhuman antibody may be humanized by recombinant methods to reduce its immunogenicity in man. Methods for humanizing antibodies are known to those skilled in the art. As used herein, "monoclonal antibody," also designated as mAb, is used to describe antibody molecules whose primary sequences are essentially identical and which exhibit the same antigenic specificity. Monoclonal antibodies may be produced by hybridoma, recombinant, transgenic or other techniques known to one skilled in the art. The term "antibody" includes, but is not limited to, both naturally occurring and non-naturally occurring antibodies. Specifically, the term "antibody" includes polyclonal and monoclonal antibodies, and antigen-binding fragments thereof. Furthermore, the term "antibody" includes chimeric antibodies, wholly synthetic antibodies, and antigen-binding fragments thereof. Accordingly, in one embodiment, the antibody is a monoclonal antibody. In one embodiment, the antibody is a polyclonal antibody. In one embodiment, the antibody is a humanized antibody. In one embodiment, the antibody is a chimeric antibody. Such chimeric antibodies may comprise a portion of an antibody from one source and a portion of an antibody from another source.

In one embodiment, the portion of the antibody comprises a light chain of the antibody. As used herein, "light chain" means the smaller polypeptide of an antibody molecule composed of one variable domain (VL) and one constant domain (CL), or fragments thereof. In one embodiment, the portion of the antibody comprises a heavy chain of the antibody. As used herein, "heavy chain" means the larger polypeptide of an antibody molecule composed of one variable domain (VH) and three or four constant domains (CH1, CH2, CH3, and CH4), or fragments thereof. In one embodiment, the portion of the antibody comprises a Fab portion of the antibody. As used herein, "Fab" means a monovalent antigen binding fragment of an immunoglobulin that consists of one light chain and part of a heavy chain. It can be obtained by brief papain digestion or by recombinant methods. In one embodiment, the portion of the antibody comprises a F(ab')$_2$ portion of the antibody. As used herein, "F(ab')2 fragment" means a bivalent antigen binding fragment of an immunoglobulin that consists of both light chains and part of both heavy chains. It can be obtained by brief pepsin digestion or recombinant methods. In one embodiment, the portion of the antibody comprises a Fd portion of the antibody. In one embodiment, the portion of the antibody comprises a Fv portion of the antibody. In one embodiment, the portion of the antibody comprises a variable domain of the antibody. In one embodiment, the portion of the antibody comprises a constant domain of the antibody. In one embodiment, the portion of the antibody comprises one or more CDR domains of the antibody. As used herein, "CDR" or "complementarity determining region" means a highly variable sequence of amino acids in the variable domain of an antibody.

This invention provides humanized forms of the antibodies described herein. As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody.

U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 and 5,693,761 and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above patents U.S. Pat. Nos. 5,585,089 and 5,693, 761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3Å of the CDRs in a three dimensional model of the antibody and is predicted to be capable of interacting with the CDRs. The above methods are merely illustrative of some of the methods that one skilled in the art could employ to make humanized antibodies.

This invention provides isolated nucleic acids encoding the antibodies described herein or their humanized versions. The nucleic acid can be RNA, DNA or cDNA. In one embodiment, the nucleic acid encodes the light chain. In one embodiment, the nucleic acid encodes the heavy chain. In one embodiment, the nucleic acid encodes both the heavy and light chains. In one embodiment, one or more nucleic acids encode the Fab portion.

In one embodiment, one or more nucleic acids encode CDR portions. In one embodiment, the nucleic acid encodes the variable domain. In one embodiment of the agents described herein, the agent is a polypeptide. In one embodiment of the agents described herein, the agent is a oligopeptide. As used herein, "polypeptide" means two or more amino acids linked by a peptide bond.

The nucleic acids, polyepeptides and antibodies described herein may be isolated and/or purified. One skilled in the art would know how to isolate and/or purify them. Methods are provided in any laboratory manual such as "Molecular Cloning" by Samrook, Fritsch and Maniatis.

In one embodiment of the agents described herein, the compound is a nonpeptidyl agent. As used herein, "nonpeptidyl agent" means an agent that does not consist in its entirety of a linear sequence of amino acids linked by peptide bonds. A nonpeptidyl molecule may, however, contain one or more peptide bonds. In one embodiment, the nonpeptidyl agent is a compound having a molecular weight less than 500 daltons. As used herein, a "small molecule" is one having a molecular weight less than 500 daltons.

The polypeptides described herein may be made by any means known to one skilled in the art. For example, the protein may be made by recombinant expression from a nucleic acid, such as a plasmid or vector comprising the encoding nucleic acid, wherein the plasmid or vector is in a suitable host cell, i.e. a host-vector system for the production of the polypeptide of interest. A suitable vector may be made which comprises suitable regulatory sequences, such as enhancers and promoters. The host cell may be of any type, including but not limited to mammalian, bacteria and yeast cells. Suitable bacterial cells include *E. coli* cells. Suitable mammalian cells include but are not limited to human embryonic kidney (HEK) 293T cells, HeLa cells, NIH 3T3 cells Chinese hamster ovary (CHO) cells and Cos cells.

This invention provides a method of testing a compound to determine whether it is an inhibitor of formation of a complex between a p66 subunit polypeptide of HIV-1 reverse transcriptase and a p51 subunit polypeptide of HIV-1 reverse transcriptase which comprises: a) contacting a yeast cell cotransformed with a first plasmid which expresses in the cell a fusion protein comprising the p66 subunit polypeptide of HIV-1 reverse transcriptase and a second plasmid which expresses in the cell a fusion protein comprising the p51 subunit polypeptide of HIV-1 reverse transcriptase with the compound wherein the cell further comprises a reporter gene which is activated in the presence of a complex between the p66 subunit polypeptide and the p51 subunit polypeptide; b) determining the level of activity of the reporter gene in the cell in the presence of the compound; and c) comparing the level of activity of the reporter gene determined in step (b) with the level of activity of the reporter gene in the absence of the compound, wherein a decreased level of activity of the reporter gene indicates that the compound is an inhibitor of the formation of the complex between the p51 subunit polypeptide of HIV-1 reverse transcriptase and the p66 subunit polypeptide of HIV-1 reverse transcriptase.

In an embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA fused to the p66 subunit polypeptide of HIV-1 reverse transcriptase at amino acid position 1 of the N-terminal amino acid sequence of the full length bacterial protein LexA and the fusion protein expressed by the second plasmid further comprises amino acids at positions 768–881 of the C-terminal amino acid sequence of Gal4AD, wherein the C-terminal amino acid sequence of Gal4AD is fused at amino acid position 881 to one end of an influenza hemagglutinin (HA) epitope tag, wherein the p51 subunit polypeptide is fused to the second end of the influenza HA epitope tag.

In another embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA fused to the p66 subunit polypeptide of HIV-1 reverse transcriptase at amino acid position 1 of the N-terminal amino acid sequence of the full length bacterial protein LexA and the fusion protein expressed by the second plasmid further comprises amino acids at positions 768–881 of the C-terminal amino acid sequence of Gal4AD fused at position 881 to the p51 subunit polypeptide of HIV-1 reverse transcriptase.

In still another embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids 1–87 of the LexA DNA binding domain fused to the p66 subunit polypeptide of HIV-1 reverse transcriptase at amino acid position 87 and the fusion protein expressed by the second plasmid further comprises amino acids at positions 768–881 of the C-terminal amino acid sequence of Gal4AD, wherein the C-terminal amino acid sequence of Gal4AD is fused at amino acid position 881 to one end of an influenza hemagglutinin (HA) epitope tag, wherein the p51 subunit polypeptide is fused to the second end of the influenza HA epitope tag.

In a further embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids 1–87 of the LexA DNA binding domain fused to the p66 subunit polypeptide of HIV-1 reverse transcriptase at amino acid position 87 and the fusion protein expressed by the second plasmid further comprises amino acids at positions 768–881 of the C-terminal amino acid sequence of Gal4AD fused at position 881 to the p51 subunit polypeptide of HIV-1 reverse transcriptase.

In a still further embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA protein fused at amino acid position 202 to a first end of a six alanine linker, wherein the p66 subunit polypeptide is fused at amino acid 1 to the second end of the six alanine linker and the fusion protein expressed by the second plasmid expresses further comprises amino acids at positions 768–881 of the C-terminal amino acid sequence of Gal4AD fused at position 881 to the p51 subunit polypeptide of HIV-1 reverse transcriptase.

In yet another embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA protein fused at amino acid position 202 to one end of a six alanine linker and the p66 subunit polypeptide fused at amino acid 1 to the other end of the six alanine linker and the fusion protein expressed by the second plasmid further comprises amino acids at positions 768–881 of the C-terminal amino acid sequence of Gal4AD wherein said C-terminal sequence is fused at amino acid position 881 to one end of an influenza hemagglutinin (HA) epitope tag and the p51 subunit polypeptide is fused at the other end of the HA epitope tag.

In another embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused to a first end of an influenza hemagglutinin (HA) epitope and a six alanine linker fused at a first end to the second end of the influenza hemagglutinin (HA) epitope, wherein the p66 subunit polypeptide of HIV-1 reverse transcriptase is fused at amino acid 1 to the second end of the six alanine linker and the fusion protein expressed by second plasmid further comprises full length LexA bacterial protein LexA fused at amino acid 1 to the p51 subunit polypeptide of HIV-1 reverse transcriptase.

In a further embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused to a first end of an influenza hemagglutinin (HA) epitope and a six alanine linker fused at a first end to the second end of the influenza hemagglutinin (HA) epitope, wherein the p66 subunit polypeptide of HIV-1 reverse transcriptase is fused at amino acid 1 to the second end of the six alanine linker and the fusion protein expressed by the second plasmid further comprises the LexA DNA binding domain fused to amino acid position 1 of the p51 subunit polypeptide of HIV-1 reverse transcriptase.

In a further embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused to a first end of an influenza hemagglutinin (HA) epitope and a six alanine linker fused at a first end to the second end of the influenza hemagglutinin (HA) epitope, wherein the p66 subunit polypeptide of HIV-1 reverse transcriptase is fused at amino acid 1 to the second end of the six alanine linker and the fusion protein expressed by the second plasmid further comprises the GAL4 DNA binding domain fused to amino acid position 1 of the p51 subunit polypeptide of HIV-1 reverse transcriptase.

In still another embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD, wherein the C-terminal amino acid sequence of Gal4AD is fused at amino acid position 881 to the p66 subunit polypeptide of HIV-1 reverse transcriptase, and the fusion protein expressed by second plasmid further comprises full length LexA bacterial protein LexA fused at amino acid position 1 to the p51 subunit polypeptide of HIV-1 reverse transcriptase.

In another embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused at amino acid position 881 to the p66 subunit polypeptide of HIV-1 reverse transcriptase and the fusion protein expressed by the second plasmid further comprises the LexA DNA binding domain fused to amino acid position 1 of the p51 subunit polypeptide of HIV-1 reverse transcriptase.

In a further embodiment of the above-described method of testing a compound to determine whether it is an inhibitor of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused at amino acid position 881 to the p66 subunit polypeptide of HIV-1 reverse transcriptase and the fusion protein expressed by the second plasmid further comprises the GAL4 DNA binding domain fused to amino acid position 1 of the p51 subunit polypeptide of HIV-1 reverse transcriptase.

One of skill will readily be able to make or use the plasmids described herein using the known nucleic acid sequence for HIV-1 reverse transcriptase, and the p66 subunit polypeptide thereof or the p51 subunit polypeptide thereof which may be comprised in expression vectors made by one of ordinary skill in the art; and make or purchase the vectors used herein comprising the full length LexA protein or truncated portions thereof, i.e. the lexA DNA binding domain, the GAL4 DNA binding domain, and GAL4 activation domain (GAL4AD) and with an HA epitope tag between the (GAL4AD) and the polylinker.

The inhibitors determined by the above-described methods are useful for the preparation of drugs, as pharmaceutical compositions, which will block complex formation between the p66 subunit polypeptide of HIV-1 reverse transcriptase and the p51 subunit polypeptide of HIV-1 reverse transcriptase so as to kill the HIV-1 virus or render it inactive or inacabable of infecting cells of a subject, including a human subject.

This invention also provides a method of making a pharmaceutical composition comprising an inhibitor of the formation of the complex between the p66 subunit polypeptide of HIV-1 reverse transcriptase and the p51 subunit polypeptide of HIV-1 reverse transcriptase which comprises: a) determining whether a compound is an inhibitor of the formation of the complex between the p66 subunit polypeptide of HIV-1 reverse transcriptase and the p51 subunit polypeptide of HIV-1 reverse transcriptase according to a method which comprises: i) contacting a yeast cell cotransformed with a first plasmid which expresses in the cell a fusion protein comprising the p66 subunit polypeptide of HIV-1 reverse transcriptase and a second plasmid which expresses in the cell a fusion protein comprising the p51 subunit polypeptide of HIV-1 reverse transcriptase with the compound wherein the cell further comprises a reporter gene which is activated in the presence of a complex between the p66 subunit polypeptide and the p51 subunit polypeptide; ii) determining the level of activity of the reporter gene in the cell in the presence of the compound; and iii) comparing the level of activity of the reporter gene determined in step (ii) with the level of activity of the reporter gene in the absence of the compound, wherein a decreased level of activity of the reporter gene indicates that the compound is an inhibitor of the formation of the complex between the p51 subunit polypeptide of HIV-1 reverse transcriptase and the p66 subunit polypeptide of HIV-1 reverse transcriptase; and b) admixing the compound determined to be the inhibitor in step (a)(iii) with a pharmaceutically acceptable carrier. Any of the above-described methods to determine whether a compound is an inhibitor of the formation of the complex between the p66 subunit polypeptide of HIV-1 reverse transcriptase and the p51 subunit polypeptide of HIV-1 reverse transcriptase may be used in the method of making a pharmaceutical composition comprising the determined inhibitor compound, but is not limited thereto, since one of skill will readily be able to substitute well known reporter genes for the reporter genes used in the examples herein. Moreover, one of skill is not limited to using the yeast cells exemplified in any of the above-described methods herein, but may modify the methods to use other eukaryotic cells, mammalian cells or cell lines such as 298 T cells.

This invention further provides a method of testing a compound to determine whether it is an activator of formation of a complex between a p66 subunit polypeptide of HIV-1 reverse transcriptase and a p51 subunit polypeptide of HIV-1 reverse transcriptase which comprises: a) contacting a yeast cell cotransformed with a first plasmid which expresses in the cell a fusion protein comprising the p66 subunit polypeptide of HIV-1 reverse transcriptase and a second plasmid which expresses in the cell a fusion protein comprising the p51 subunit polypeptide of HIV-1 reverse transcriptase with the compound wherein the cell further comprises a reporter gene which is activated in the presence of a complex between the p66 subunit polypeptide and the p51 subunit polypeptide; b) determining the level of activity of the reporter gene in the cell in the presence of the compound; and c) comparing the level of activity of the reporter gene determined in step (b) with the level of activity of the reporter gene in the absence of the compound, wherein an increased level of activity of the reporter gene indicates that the compound is an activator of the formation of the complex between the p51 subunit polypeptide of HIV-1 reverse transcriptase and the p66 subunit polypeptide of HIV-1 reverse transcriptase.

In an embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA fused to the p66 subunit polypeptide of HIV-1 reverse transcriptase at amino acid position 1 of the N-terminal amino acid sequence of the full length bacterial protein LexA and the fusion protein expressed by the second plasmid further comprises amino acids at positions 768–881 of the C-terminal amino acid sequence of Gal4AD, wherein the C-terminal amino acid sequence of Gal4AD is fused at amino acid position 881 to one end of an influenza hemagglutinin (HA) epitope tag, wherein the p51 subunit polypeptide is fused to the second end of the influenza HA epitope tag.

In another embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA fused to the p66 subunit polypeptide of HIV-1 reverse transcriptase at amino acid position 1 of the N-terminal amino acid sequence of the full length bacterial protein LexA and the fusion protein expressed by the second plasmid further comprises amino acids at positions 768–881 of the C-terminal amino acid sequence of Gal4AD fused at position 881 to the p51 subunit polypeptide of HIV-1 reverse transcriptase.

In a further embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids 1–87 of the LexA DNA binding domain fused to the p66 subunit polypeptide of HIV-1 reverse transcriptase at amino acid position 87 and the fusion protein expressed by the second plasmid further comprises amino acids at positions 768–881 of the C-terminal amino acid sequence of Gal4AD, wherein the C-terminal amino acid sequence of Gal4AD is fused at amino acid position 881 to one end of an influenza hemagglutinin (HA) epitope tag, wherein the p51 subunit polypeptide is fused to the second end of the influenza HA epitope tag.

In another embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids 1–87 of the LexA DNA binding domain fused to the p66 subunit polypeptide of HIV-1 reverse transcriptase at amino acid position 87 and the fusion protein expressed by the second plasmid further comprises amino acids at positions 768–881 of the C-terminal amino acid sequence of Gal4AD fused at position 881 to the p51 subunit polypeptide of HIV-1 reverse transcriptase.

In a still further embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA protein fused at amino acid position 202 to a first end of a six alanine linker, wherein the p66 subunit polypeptide is fused at amino acid 1 to the second end of the six alanine linker and the fusion protein expressed by the second plasmid expresses further comprises amino acids at positions 768–881 of the C-terminal amino acid sequence of Gal4AD fused at position 881 to the p51 subunit polypeptide of HIV-1 reverse transcriptase.

In another embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises full length bacterial protein LexA protein fused at amino acid position 202 to one end of a six alanine linker and the p66 subunit polypeptide fused at amino acid 1 to the other end of the six alanine linker and the fusion protein expressed by the second plasmid further comprises amino acids at positions 768–881 of the C-terminal amino acid sequence of Gal4AD wherein said C-terminal sequence is fused at amino acid position 881 to one end of an influenza hemagglutinin (HA) epitope tag and the p51 subunit polypeptide is fused at the other end of the HA epitope tag.

In a further embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused to a first end of an influenza hemagglutinin (HA) epitope and a six alanine linker fused at a first end to the second end of the influenza hemagglutinin (HA) epitope, wherein the p66 subunit polypeptide of HIV-1 reverse transcriptase is fused at amino acid 1 to the second end of the six alanine linker and the fusion protein expressed by second plasmid further comprises full length LexA bacterial protein LexA fused at amino acid 1 to the p51 subunit polypeptide of HIV-1 reverse transcriptase.

In another embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused to a first end of an influenza hemagglutinin (HA) epitope and a six alanine linker fused at a first end to the second end of the influenza hemagglutinin (HA) epitope, wherein the p66 subunit polypeptide of HIV-1 reverse transcriptase is fused at amino acid 1 to the second end of the six alanine linker and the fusion protein expressed by the second plasmid further comprises the LexA DNA binding domain fused to amino acid position 1 of the p51 subunit polypeptide of HIV-1 reverse transcriptase.

In still another embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused to a first end of an influenza hemagglutinin (HA) epitope and a six alanine linker fused at a first end to the second end of the influenza hemagglutinin (HA) epitope, wherein the p66 subunit polypeptide of HIV-1 reverse transcriptase is fused at amino acid 1 to the second end of the six alanine linker and the fusion protein expressed by the second plasmid further comprises the GAL4 DNA binding domain fused to amino acid position 1 of the p51 subunit polypeptide of HIV-1 reverse transcriptase.

In a further embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD, wherein the C-terminal amino acid sequence of Gal4AD is fused at amino acid position 881 to the p66 subunit polypeptide of HIV-1 reverse transcriptase, and the fusion protein expressed by second plasmid further comprises full length LexA bacterial protein LexA fused at amino acid position 1 to the p51 subunit polypeptide of HIV-1 reverse transcriptase.

In another embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused at amino acid position 881 to the p66 subunit polypeptide of HIV-1 reverse transcriptase and the fusion protein expressed by the second plasmid further comprises the LexA DNA binding domain fused to amino acid position 1 of the p51 subunit polypeptide of HIV-1 reverse transcriptase.

In a further embodiment of the above-described method of testing a compound to determine whether it is an activator of formation of a complex between a p66 subunit polypeptide of HIV-1 reverse transcriptase and a p51 subunit polypeptide of HIV-1 reverse transcriptase, the fusion protein expressed by the first plasmid further comprises amino acids at positions 768–881 of the C-terminal amino acid sequence of Gal4AD fused at amino acid position 881 to the p66 subunit polypeptide of HIV-1 reverse transcriptase and the fusion protein expressed by the second plasmid further comprises the GAL4 DNA binding domain fused to amino acid position 1 of the p51 subunit polypeptide of HIV-1 reverse transcriptase.

The activators determined by the above-described methods are useful for the preparation of drugs, as pharmaceutical compositions, which will enhance complex formation prematurely or inappropriately between the p66 subunit polypeptide of HIV-1 reverse transcriptase and the p51 subunit polypeptide of HIV-1 reverse transcriptase so as to kill the HIV-1 virus or render the the HIV-1 virus inactive or incapable of infecting cells of a subject, i.e. lack the functions of an infected HIV-1 virus, including human subjects.

This invention also provides a method of making a pharmaceutical composition comprising an activator of the formation of the complex between the p66 subunit polypeptide of HIV-1 reverse transcriptase and the p51 subunit polypeptide of HIV-1 reverse transcriptase which comprises:

a) determining whether a compound is an activator of the formation of the complex between the p66 subunit polypeptide of HIV-1 reverse transcriptase and the p51 subunit polypeptide of HIV-1 reverse transcriptase according to a method which comprises: i) contacting a yeast cell cotransformed with a first plasmid which expresses in the cell a fusion protein comprising the p66 subunit polypeptide of HIV-1 reverse transcriptase and a second plasmid which expresses in the cell a fusion protein comprising the p51 subunit polypeptide of HIV-1 reverse transcriptase with the compound wherein the cell further comprises a reporter gene which is activated in the presence of a complex between the p66 subunit polypeptide and the p51 subunit polypeptide; ii) determining the level of activity of the reporter gene in the cell in the presence of the compound; and iii) comparing the level of activity of the reporter gene determined in step (ii) with the level of activity of the reporter gene in the absence of the compound, wherein an increased level of activity of the reporter gene indicates that the compound is an activator of the formation of the complex between the p51 subunit polypeptide of HIV-1 reverse transcriptase and the p66 subunit polypeptide of HIV-1 reverse transcriptase; and b) admixing the compound determined to be the activator in step (a)(iii) with a pharmaceutically acceptable carrier. Any of the above-described methods to determine whether a compound is an activator of the formation of the complex between the p66 subunit polypeptide of HIV-1 reverse transcriptase and the p51 subunit polypeptide of HIV-1 reverse transcriptase may be used in the method of making a pharmaceutical composition comprising the determined activator compound, but is not limited thereto, since one of skill will readily be able to substitute well known reporter genes for the reporter genes used in the examples herein. Moreover, one of skill is not limited to using the yeast cells exemplified in any of the above-described methods herein, but may modify the methods to use other eukaryotic cells, mammalian cells or cell lines such as 298 T cells.

This invention further provides a method of testing a compound to determine whether it is an inhibitor of formation of a complex between a first p66 subunit polypeptide of HIV-1 reverse transcriptase and a second p66 subunit polypeptide of HIV-1 reverse transcriptase which comprises: a) contacting a yeast cell cotransformed with a first plasmid which expresses in the cell a fusion protein comprising the first p66 subunit polypeptide of HIV-1 reverse transcriptase and a second plasmid which expresses in the cell a fusion protein comprising the second p66 subunit polypeptide of HIV-1 reverse transcriptase with the compound wherein the cell further comprises a reporter gene which is activated in the presence of a complex between the first p66 subunit polypeptide and the second p66 subunit polypeptide; b) determining the level of activity of the reporter gene in the cell in the presence of the compound; and c) comparing the level of activity of the reporter gene determined in step (b) with the level of activity of the reporter gene in the absence of the compound, wherein a decreased level of activity of the reporter gene indicates that the compound is an inhibitor of the formation of the complex between the first p66 subunit polypeptide of HIV-1 reverse transcriptase and the second p66 subunit polypeptide of HIV-1 reverse transcriptase.

In an embodiment of the above-described method of testing a compound to determine whether it is an inhibitor of formation of a complex between a first p66 subunit polypeptide of HIV-1 reverse transcriptase and a second p66 subunit polypeptide of HIV-1 reverse transcriptase, the fusion protein expressed by the first plasmid further comprises full length bacterial protein LexA fused to the first p66 subunit polypeptide of HIV-1 reverse transcriptase at amino acid position 1 of the N-terminal amino acid sequence of the full length bacterial protein LexA and the fusion protein expressed by second plasmid further comprises amino acids at positions 768–881 of the C-terminal amino acid sequence of Gal4AD fused to one end of an influenza hemagglutinin (HA) epitope and a six alanine linker fused at a first end to the second end of the influenza hemagglutinin (HA) epitope, wherein the second p66 subunit polypeptide of HIV-1 reverse transcriptase is fused at the second end of the six alanine linker.

This invention also provides a method of making a pharmaceutical composition comprising an inhibitor of formation of a complex between a first p66 subunit polypeptide of HIV-1 reverse transcriptase and a second p66 subunit polypeptide of HIV-1 reverse transcriptase which comprises: a) determining whether a compound is an inhibitor of formation of a complex between a first p66 subunit polypeptide of HIV-1 reverse transcriptase and a second p66 subunit polypeptide of HIV-1 reverse transcriptase according to a method which comprises: i) contacting a yeast cell cotransformed with a first plasmid which expresses in the cell a fusion protein comprising the first p66 subunit polypeptide of HIV-1 reverse transcriptase and a second plasmid which expresses in the cell a fusion protein comprising the second p66 subunit polypeptide of HIV-1 reverse transcriptase with the compound wherein the cell further comprises a reporter gene which is activated in the presence of a complex between the first p66 subunit polypeptide and the second p66 subunit polypeptide; ii) determining the level of activity of the reporter gene in the cell in the presence of the compound; and iii) comparing the level of activity of the reporter gene determined in step (ii) with the level of activity of the reporter gene in the absence of the compound, wherein a decreased level of activity of the reporter gene indicates that the compound is an inhibitor of the formation of the complex between the first p66 subunit polypeptide of HIV-1 reverse transcriptase and the second p66 subunit polypeptide of HIV-1 reverse transcriptase; and b) admixing the compound determined to be the inhibitor in step (a) (iii) with a pharmaceutically acceptable carrier. Any of the above-described methods to determine whether a compound is an inhibitor of formation of a complex between a first p66 subunit polypeptide of HIV-1 reverse transcriptase and a second p66 subunit polypeptide of HIV-1 reverse transcriptase may be used in the method of making a pharmaceutical composition comprising the determined inhibitor compound, but is not limited thereto, since one of skill will readily be able to substitute well known reporter genes for the reporter genes used in the examples herein. Moreover, one of skill is not limited to using the yeast cells exemplified in any of the above-described methods herein, but may modify the methods to use other eukaryotic cells, mammalian cells or cell lines such as 298 T cells.

The inhibitors determined by the above-described methods are useful for the preparation of drugs, as pharmaceutical compositions, which will block complex formation between the first p66 subunit polypeptide of HIV-1 reverse transcriptase (homodimer)and the second p66 subunit polypeptide of HIV-1 reverse transcriptase (homodimer so as to kill the HIV-1 virus (as well as formation of a complex between the p66 subunit polypeptide of HIV-1 RT and the p51 subunit polypeptide of HIV-1 RT) or render it inactive or inacabable of infecting cells of a subject, including a human subject.

This invention still further provides a method of testing a compound to determine whether it is an activator of formation of a complex between a first p66 subunit polypeptide of HIV-1 reverse transcriptase and a second p66 subunit polypeptide of HIV-1 reverse transcriptase which comprises: a) contacting a yeast cell cotransformed with a first plasmid which expresses in the cell a fusion protein comprising the first p66 subunit polypeptide of HIV-1 reverse transcriptase and a second plasmid which expresses in the cell a fusion protein comprising the second p66 subunit polypeptide of HIV-1 reverse transcriptase with the compound wherein the cell further comprises a reporter gene which is activated in the presence of a complex between the first p66 subunit polypeptide and the second p66 subunit polypeptide; b) determining the level of activity of the reporter gene in the cell in the presence of the compound; and c) comparing the level of activity of the reporter gene determined in step (b) with the level of activity of the reporter gene in the absence of the compound, wherein a increased level of activity of the reporter gene indicates that the compound is an activator of the formation of the complex between the first p66 subunit polypeptide of HIV-1 reverse transcriptase and the second p66 subunit polypeptide of HIV-1 reverse transcriptase.

In an embodiment of the above-described method of testing a compound to determine whether it is an activator of formation of a complex between a first p66 subunit polypeptide of HIV-1 reverse transcriptase and a second p66 subunit polypeptide of HIV-1 reverse transcriptase, the fusion protein expressed by the first plasmid further comprises full length bacterial protein LexA fused to the first p66 subunit polypeptide of HIV-1 reverse transcriptase at amino acid position 1 of the N-terminal amino acid sequence of the full length bacterial protein LexA and the fusion protein expressed by second plasmid further comprises amino acids at positions 768–881 of the C-terminal amino acid sequence of Gal4AD fused to one end of an influenza hemagglutinin (HA) epitope and a six alanine linker fused at a first end to the second end of the influenza hemagglutinin (HA) epitope, wherein the second p66 subunit polypeptide of HIV-1 reverse transcriptase is fused at the second end of the six alanine linker.

The activators determined by the above-described methods are useful for the preparation of drugs, as pharmaceutical compositions, which will enhance complex formation prematurely or inappropriately between the first p66 subunit polypeptide of HIV-1 reverse transcriptase and the second p66 subunit polypeptide of HIV-1 reverse transcriptase so as to kill the HIV-1 virus or render the the HIV-1 virus inactive or incapable of infecting cells of a subject, i.e. lack the functions of an infected HIV-1 virus, including human subjects.

This invention also provides a method of making a pharmaceutical composition comprising an activator of formation of a complex between a first p66 subunit polypeptide of HIV-1 reverse transcriptase and a second p66 subunit polypeptide of HIV-1 reverse transcriptase which comprises: a) determining whether a compound is an activator of formation of a complex between a first p66 subunit polypeptide of HIV-1 reverse transcriptase and a second p66 subunit polypeptide of HIV-1 reverse transcriptase according to a method which comprises: i) contacting a yeast cell cotransformed with a first plasmid which expresses in the cell a fusion protein comprising the first p66 subunit polypeptide of HIV-1 reverse transcriptase and a second plasmid which expresses in the cell a fusion protein comprising the second p66 subunit polypeptide of HIV-1 reverse transcriptase with the compound wherein the cell further comprises a reporter gene which is activated in the presence of a complex between the first p66 subunit polypeptide and the second p66 subunit polypeptide; ii) determining the level of activity of the reporter gene in the cell in the presence of the compound; and iii) comparing the level of activity of the reporter gene determined in step (ii) with the level of activity of the reporter gene in the absence of the compound, wherein a increased level of activity of the reporter gene indicates that the compound is an activator of the formation of the complex between the first p66 subunit polypeptide of HIV-1 reverse transcriptase and the second p66 subunit polypeptide of HIV-1 reverse transcriptase; and b) admixing the compound determined to be the activator in step (a) (iii) with a pharmaceutically acceptable carrier. Any of the above-described methods to determine whether a compound is an activator of formation of a complex between a first p66 subunit polypeptide of HIV-1 reverse transcriptase and a second p66 subunit polypeptide of HIV-1 reverse transcriptase may be used in the method of making a pharmaceutical composition comprising the determined activator compound, but is not limited thereto, since one of skill will readily be able to substitute well known reporter genes for the reporter genes used in the examples herein. Moreover, one of skill is not limited to using the yeast cells exemplified in any of the above-described methods herein, but may modify the methods to use other eukaryotic cells, mammalian cells or cell lines such as 298 T cells.

Methods of treating a subject infected with HIV-1 include administering any of the above-described pharmaceutical compositions comprising: an inhibitor of the formation of the complex between the p66 subunit polypeptide of HIV-1 reverse transcriptase; an activator of the formation of the complex between the p66 subunit polypeptide of HIV-1 reverse transcriptase and the p51 subunit polypeptide of HIV-1 reverse transcriptase; an inhibitor of formation of a complex between a first p66 subunit polypeptide of HIV-1 reverse transcriptase and a second p66 subunit polypeptide of HIV-1 reverse transcriptase; and/or an activator of formation of a complex between a first p66 subunit polypeptide of HIV-1 reverse transcriptase and a second p66 subunit polypeptide of HIV-1 reverse transcriptase. One of skill will recognize that other pharmaceutical compositions may be administered to a subject infected with HIV-1 in conjunction with the pharmaceutical compositions provided by the methods set forth herein.

The invention also provides a pharmaceutical composition comprising an effective amount of any of the above-described inhibitors and a pharmaceutically acceptable carrier. The invention also provides a pharmaceutical composition comprising an effective amount of any of the above-described activators and a pharmaceutically acceptable carrier. In the subject invention an "effective amount" is any amount of an inhibitor or activator which, when administered to a subject suffering from a disease or abnormality against which the inhibitors or activators are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound or composition may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The inhibitor(s) or activator(s) determined by the methods described above can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The inhibitor(s) or activator(s) can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular inhibitor(s) or activator(s) in use, the strength of the preparation, the mode of administration, and the advancement of the disease condition or abnormality. Additional factors depending on the particular subject being treated will result in a need to adjust dosages, including subject age, weight, gender, diet, and time of administration.

This invention will be better understood from the Experimental Details that follow. However, one skilled in the art will readily appreciate that the specific methods and results discussed are merely illustrative of the invention as described more fully in the claims that follow thereafter.

Experimental Details

First Series of Experiments

Materials and Methods

Bacterial and Yeast Strains

*Saccharomyces cerevisiae* strain CTY10-5d (MATa ade2 trpl-901 leu2-3, 112 his3-200 gal4-gal80-URA3::lexA-lacZ) contains an integrated GAL1-lacZ gene with the lexA operator (a gift from Stanley Fields, State University of New York, Stony Brook). The yeast strain HF7c contains CYC1-lacZ gene with three copies of the GAL4 responsive UASG 17-mer operator (CLONTECH). *Escherichia coli* mutator strain XL1-Red (Stratagene) was used for random mutagenesis whereas XL1-Blue (Stratagene) was used to amplify the mutated library. KC8 (CLONTECH), an auxotrophic leuB, trpC and hisB *E. coli* strain, was used to isolate plasmids from yeast. *E. coli* strains M15 and BL21 were used to express p66-His and glutathione S-transferase-tagged p51 (GST-p51) respectively (see below).

Yeast Methods

Transformation of yeast and the qualitative β-galactosidase (β-gal) colony lift assay were as published (19). Quantification of protein-protein interactions was determined using the β-gal liquid assay performed on permeabilized yeast grown from three independent transformants using orthonitrophenyl-β-D-galactopyranoside as substrate (19).

Protein Expression and RT Activity

Fusion protein expression in yeast was determined by Western blot of lysates with Gal4AD polyclonal antibodies (Upstate Biotechnology, Lake Placid, N.Y.), anti-lexA polyclonal antibodies (Invitrogen) and HIV-1 RT polyclonal (Intracel, Cambridge, Mass.) or 5B2 monoclonal antibody (20). Immunodetection was with ECL-Plus (Amersham) To measure RT activity, yeast lysates were prepared by glass bead disruption (19) and enzyme activity was determined in exogenous assays (21) and quantified by phosphoimager analysis.

Yeast Shuttle Vectors pSH2-1 (22) and pLex202-PL (23) express the lexA DNA binding domain (lexA$_{87}$) and the full-length lexA protein (lexA$_{202}$), respectively. pGBT9 and pAS2-1, both containing the GAL4 DNA binding domain (GAL4 BD), were purchased from CLONTECH. pNLexA allows expression of proteins fused to the N terminus of full-length lexA$_{202}$ (OriGene Technologies, Rockville, Md.). pGADNOT (18) and pACTII (24) allow expression of proteins fused to the Gal4 activation domain (GAL4 AD). pACTII also contains the influenza hemagglutinin (HA) epitope tag located between GAL4AD and the polylinker.

Construction of HIV-1 RT Fusions in Yeast Vectors

Constructs and expressed fusion proteins are as described in FIG. 1. The RT sequence for constructing the following expression vectors was amplified from HIV-1 molecular clone pNLenv-1 (containing the HIVNL43 sequence) (25).

The p66 amplimers were cloned into the BamHI-SalI sites of pGBT9, pSH2-1, pLex202-PL, pACTII and pGADNOT; the BamH1-XhoI sites of pACTII; and the EcoRI-BamHI sites of pNLexA. p51 amplimers were cloned into the BamHI-SalI sites of these vectors except for cloning into pACTII, where the BamH1-XhoI sites were used. The HXB2 RT sequence from pHXB2gpt (26) was used to construct p66HXAlaLex202 and p51HXGADNOT.

Construction of HIV-1 RT Deletion Mutants

All p66 deletion mutants were prepared by cloning PCR amplimers into the BamHI-SalI sites of pSH2-1. Fingers, palm, connection, thumb and RNase H domains of HIV-1 RT are denoted F, P, C, T and R respectively. pT+C+RSH2-1 (encoding lexA$_{87}$-T+C+R) contains RT (from HIVNL43) codons 236-560. pC+RSH2-1 (encoding lexA871-C+R) contains codons 322-560 while pRSH2-1 (encoding lexA$_{87}$-R) comprises codons 425–560. All p51 deletion mutants were prepared by cloning of PCR amplimers into the BamHI-XhoI sites of pACTII. pF+P+T–ACTII (encoding Gal4AD–HA–F+P+T) includes RT codons 1–325 and pF+P-ACTII (encoding Gal4AD–HA–F+P) has codons 1–244. p51Δ13ACTII (encoding Gal4AD-HA-51Δ13) contains RT codons 1–426. p51Δ26GADNOT (encoding Gal4AD-51Δ26) was obtained by random mutagenesis of p55GADNOT in XL1-Red.

Construction of RT Fusions with the L234A Mutation and Random Mutagenesis of p66Ala234Lex202 and Selection of Revertants p66Ala234Lex202 (encoding lexA$_{202}$-Ala-66L234A) was made by inserting p66 from p6HprotL234A (a gift from Vinayaka Prasad, Albert Einstein College of Medicine, Bronx N.Y.) into the BamHI/SalI sites of pLex202-PL. p51234GADNOT (encoding Gal4AD-51L234A) was made by insertion of p51 from p6HprotL234A into the BamHI-SalI sites of pGADNOT. Second-site mutations restoring dimerization to lexA$_{202}$-Ala-66L234A were generated by propagation of p66Ala234Lex202 in XL1-Red (Stratagene). Two independent pools were prepared. CTY10-5d was cotransformed with the mutagenized library and either p51234GADNOT or p51GADNOT. Blue colonies were picked from β-gal colony lift assays and clonally purified. p66 DNA from isolated plasmids were recloned into a nonmutated pLex202-PL backbone and reintroduced into CTY10-5d to confirm the phenotype. Mutations present in p66 were determined by automated nucleotide sequencing.

Site Directed Mutagenesis p66 with genotype D110G was prepared from a p66 clone containing both D110G and L234A obtained by random mutagenesis by backmutation of codon 234 to wild-type. p66 with either the W402R or W406R substitutions were prepared by subcloning a Bsp1286I-SalI fragment (600 bp) from the clones obtained by random mutagenesis of L234A with wild-type BamHI-Bsp1286I fragment (1,080 bp) from p66HXAlaLex202 into pLex202-PL.

In Vitro Heterodimerization

Plasmids expressing wild-type and p66 mutants with a histidine tag at the C-terminus (p66-His) were constructed by cloning the p66 coding region into the SphI-BglII site of pQE-70 (Qiagen, Chatsworth, Calif.). The C-terminal tag was appended as described previously [clone 3 (27)]. Glutathione S-transferase tagged p51 (GST-p51) was prepared by subcloning the BamHI-SalI fragment from p51HXGADNOT into pGEX5X-3 (Amersham Pharmacia). Cells were induced and then lysed by the addition of 1 mg/ml of lysozyme to 1 ml of lysis buffer [50 mM sodium phosphate buffer (pH 7.8), 500 mM NaCl, 0.5% Nonidet P-40, 5 mM DTT, and 1 µg/ml each of pepstatin A, aprotinin and leupeptin] and clarified. Lysates were combined and incubated for 16 hrs at 4° C. The heterodimer was captured on Glutathione Sepharose 4B beads and unbound subunits were removed by washing with lysis buffer. Heterodimer bound to beads were resolved by SDS/PAGE. For quantification of RT activity, dimers were eluted from beads with 10 mM reduced glutathione in 50 mM Tris (pH 8.0). Samples were assayed for DNA polymerase activity on homopolymeric template-primers for various times, and the activity was determined from the initial slope of the linear phase of the time course. Western blot confirmed equal recovery of GST-51 protein in each sample.

RESULTS

Expression of RT Fusion Proteins and RT Activity

The stable expression of p66 was tested in several contexts, as either Gal4BD or LexA fusions, and using a six alanine linker to separate p66 from its fusion partner. p66 fused to the C terminus of lexA$_{87}$, the C or N termini of lexA$_{202}$ (with or without a six alanine spacer), and in a variety of contexts to the Gal4AD were all stably expressed (FIG. 1). In contrast, p66 fused to the C terminus of the Gal4BD (Gal4BD-66) was not expressed in yeast at detectable levels (FIG. 1). The smaller RT subunit, p51, was well expressed as fusions with the Gal4BD, Gal4AD, and both lexA$_{87}$ and lexA$_{202}$. We examined whether the bait fusions encoded by p66SH2-1, p66AlaLex202 and p66NLexA exhibited RT activity in yeast. All three fusion proteins demonstrated high levels of RT activity compared with protein lysates from yeast transformed with an empty vector (data not shown). These data suggest that the p66 fusion proteins are functional and in a conformation consistent with measurable catalytic activity.

Heteromeric Interactions of p66 and p51 by Transactivation in the Two-Hybrid System To test whether the Y2H system could detect the interaction of the p66/p51 heterodimer, we cotransformed yeast reporter strains with plasmids expressing p66DNA BD and p51DNA AD fusion proteins (Table 1). β-gal activity expressed in yeast, which indicates the strength of the interaction between the fusion proteins, was assessed by both qualitative and quantitative assays. The p66 bait fusions expressed from p66SH2-1, p66AlaLex202 and p66NLexA interacted with Gal4AD-p51 domain fusions (Table 1) but not with Gal4AD alone (Table 1). The strongest interactions were observed with p66 baits lexA$_{202}$-Ala-66 and 66-lexA$_{202}$. Moreover, p51 expressed in pACTII gave a stronger signal than p51GADNOT when coexpressed with p66 fusion baits. Despite the stable expression of the p66 fusion protein, lexA$_{202}$-66, no significant interaction with p51 was detected (FIG. 1). Moreover, lexA$_{202}$-66 yielded the same weak signal with the empty Gal4AD vector, pGADNOT, indicating that this version of p66 is weakly self-activating even without a partner.

TABLE 1

Interaction of p66 binding domain fusions with p51 activation domain fusions in the Y2H system

| | | β-gal activity | |
|---|---|---|---|
| Constructs | Operator | Colony* | Liquid† |
| p66SH2-1 + pGADNOT | lexA | − | ND |
| p66SH2-1 + pACTII | lexA | − | 0.02 |
| p66SH2-1 + p51GADNOT | lexA | ++ | 0.5 |
| p66SH2-1 + p51ACTII | lexA | +++ | 3.5 |

TABLE 1-continued

Interaction of p66 binding domain fusions with p51 activation domain fusions in the Y2H system

| Constructs | Operator | β-gal activity Colony* | Liquid† |
|---|---|---|---|
| p66AlaLex202 + pGADNOT | lexA | − | ND |
| p66AlaLex202 + pACTII | lexA | − | 0.04 |
| p66AlaLex202 + p51GADNOT | lexA | +++ | 1.6 |
| p66AlaLex202 + p51ACTII | lexA | +++ | 7.7 |
| p66NLexA + pGADNOT | lexA | − | 0.06 |
| p66NLexA + pACTII | lexA | − | 0.04 |
| p66NLexA + p51GADNOT | lexA | +++ | 6.6 |
| p66NLexA + p51ACTII | lexA | +++ | 25.0 |
| p66Lex202 + pGADNOT | lexA | +/− | ND |
| p66Lex202 + p51GADNOT | lexA | +/− | ND |
| p66GBT9 + pGADNOT‡ | UAS$_G$ | − | ND |
| p66GBT9 + p51GADNOT‡ | UAS$_G$ | − | ND |

Yeast strain CTY10-5d or ‡HF7c were transformed with plasmids encoding p66 bait and p51 prey fusions. Fusion proteins encoded by plasmids are described in Materials and Methods and FIG. 1.
*Transformants were lifted onto nitrocellulose and subjected to the β-gal colony lift assay to determine intensities of blue color produced; +++, strong blue in 1 h; ++, blue in 1 h; +/−, weak blue in 3 h; −, white; ND, not done.

We also showed that heteromeric interactions between p66 and p51 could be detected in the reciprocal configuration with p51 as either a LexA or Gal4BD fusion and p66 as a Gal4AD fusion (Table 2). The demonstration of heteromeric dimerization of p66 and p51 in different contexts strongly suggests that the interaction is specific. Tests for interaction with five unrelated proteins showed no signal (data not shown), providing further evidence for the specificity of RT heterodimerization in yeast.

TABLE 2

Interaction of p51 binding domain fusions with p66 activation domain fusions in the Y2H system

| Constructs | Operator | β-gal activity Colony* | Liquid |
|---|---|---|---|
| p51SH2-1 + pGADNOT | lexA | − | 0.06 |
| p51SH2-1 + pACTII | lexA | − | 0.05 |
| p51SH2-1 + p66AlaACTII | lexA | ++ | 1.2 |
| p51Lex202 + pACTII | lexA | − | 0.05 |
| p51Lex202 + p66AlaACTII | lexA | +++ | 3.2 |
| p51AS2-1 + pACTII‡ | UAS$_G$ | − | ND |
| P51AS2-1 + P66AlaACTII‡ | UAS$_G$ | ++ | ND |

Yeast strain CTY10-5d or ‡HF7c were transformed with plasmids encoding p51 bait and p66 prey fusions. Fusion proteins encoded by plasmids are described in Materials and Methods and FIG. 1.
*As defined in Table 1.
‡As defined in Table 1.

Homomeric Interactions

The interaction of the RT heterodimer p66/p51 has a dissociation constant of $10^{-9}$ M, whereas the dissociation constants for the p66 and p51 homodimers are $10^{-6}$ M and $10^{-5}$ M, respectively (9). We were unable to detect p51 homodimerization when CTY10-5d was cotransformed with either p51SH2-1 or p51Lex202 baits and p51ACTII prey (data not shown). In contrast, p66 homodimerization could be detected when yeast was cotransformed with p66NlexA bait and p66AlaACTII prey (β-gal activity 0.3 Miller units). p66 homodimerization of these two constructs was 100-fold weaker compared to the interaction of p66NlexA with p51ACTII (Table 1). The strength of the interactions observed in vivo are consistent with biochemical data.

p66 Domains that Interact with p51

Figure 2:
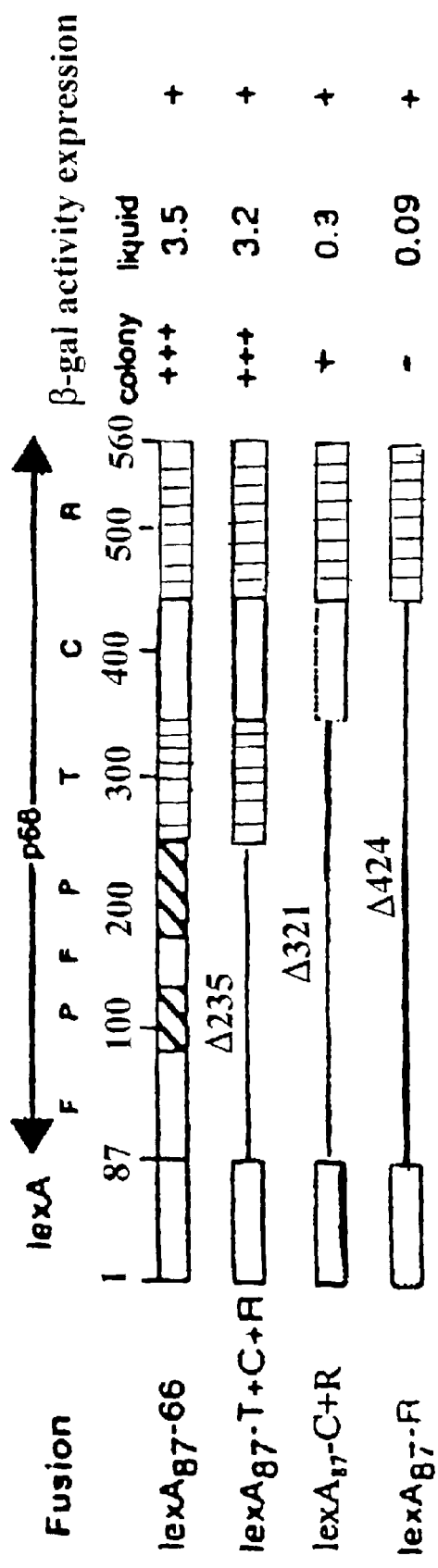

We used the Y2H RT dimerization assay to map the regions of p66 required for binding to p51 (FIG. 2). A series of mutants with sequential deletions in the polymerase subdomains were prepared as C-terminal fusions with lexA$_{87}$. Deletion of the fingers and palm subdomains (lexA$_{87}$–T+C+R) did not significantly affect binding to Gal4AD-HA-51. A further deletion of the thumb subdomain (lexA87–C+R) resulted in reduced β-gal activity (FIG. 2). Expression of the RNase H domain alone was not sufficient for interaction with p51. This lack of interaction was not attributable to an aberrant RNase H conformation, as lexA$_{87}$-R also interacted as strongly as lexA$_{87}$-66 with a cellular protein, diaphorase, that we find interacts with the RNase H domain of RT in the Y2H system (results not shown). None of the bait fusions demonstrated activation of the lacZ reporter gene when coexpressed with Gal4AD-HA alone, excluding the possibility of nonspecific self-activation by the bait fusions (results not shown). These data suggest that the connection and RNase H subdomains of p66 are sufficient for interaction with p51.

The C Terminus of p51 is Required for Interaction with p66

Figure 3:
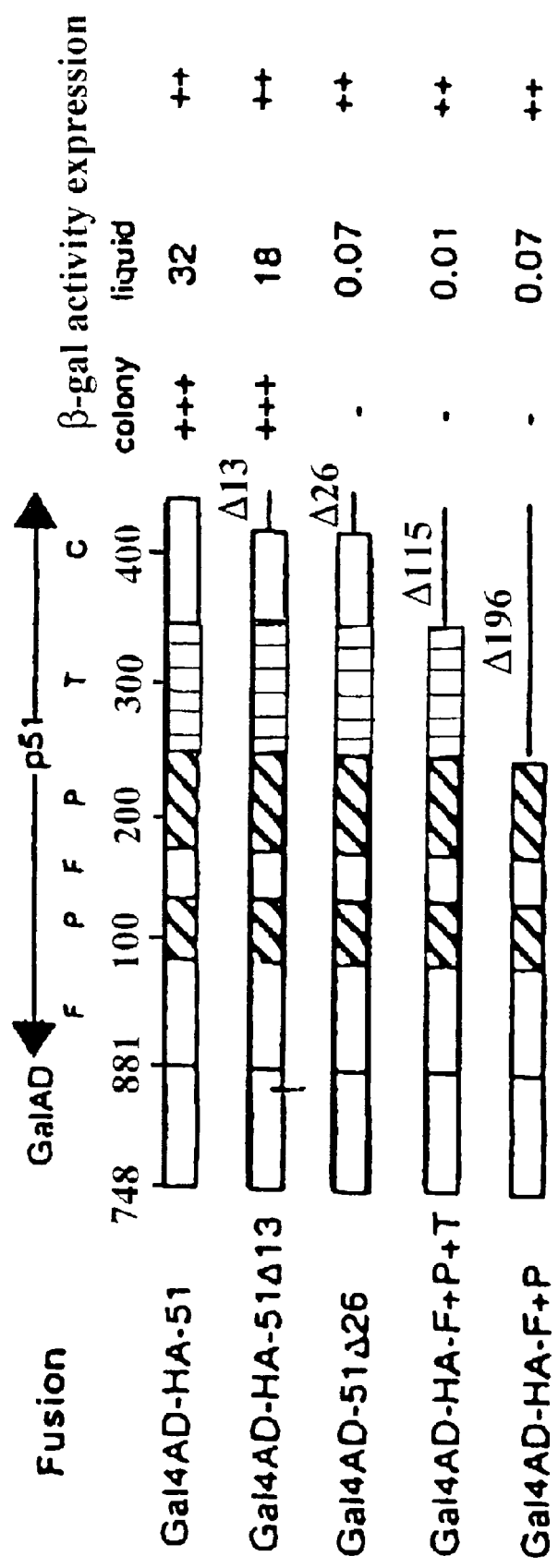

It has previously been shown biochemically that deletion of as little as 25 amino acids from the C terminus of p51 can prevent dimerization to p66 (15). To ascertain whether this effect could be observed under physiological conditions in the Y2H system, we constructed a series of C-terminal deletion mutants of p51 prey fusions and assayed interaction with p66 bait. Deletion of 13 amino acids from the C terminus of p51 had little effect (1.8-fold decrease) on dimerization with p66 (FIG. 3). However, deletions of 26 amino acids and greater abrogated RT dimerization, indicating the importance of the C-terminal 26 amino acids of p51 in these interactions. These results also suggest that the system faithfully recapitulates the behavior of the enzyme as studied in vitro.

L234A in p66 Subunit Inhibits RT Dimerization

The Y2H RT dimerization assay would be most useful if it could be applied to the analysis of single amino acid substitutions that affect heteromeric interactions. To test the system, we introduced the L234A primer grip mutation, previously shown biochemically to inhibit p66/p51 association (10), into both RT subunits. The presence of L234A in both p66 and p51 totally inhibited RT dimerization as observed by a 53-fold decrease in the β-gal signal compared to wild-type proteins (FIG. 4). To assess the effect of L234A in individual subunits CTY10d-5 was cotransformed with constructs expressing either p66 mutant bait and wild-type p51 prey, or p66 wild-type bait with psi mutant prey. Less than a two-fold decrease in the signal compared with wild-type fusions was observed when the L234A mutant p51 (Gal4AD–51L234A) was coexpressed with the wild-type fusion leXA$_{202}$-Ala-66 (FIG. 4). However, a 32-fold inhibition was observed for the interaction of the mutant lex$_{202}$-Ala-66L234A with wild-type Gal4AD-51. These data suggest that L234A affects dimerization predominantly through p66, as has been previously reported (10). Analysis of fusion protein expression in yeast by Western blot analysis revealed that all fusion proteins, including the L234A mutants, were stably expressed (results not shown).

Second-Site Mutations that Restore Heterodimerization and RT Activity to the p66L234A Mutant To gain insight into the mechanism of inhibition of RT dimerization by L234A, we attempted to select for second-site suppressor mutations in p66 that restore dimerization with p51. To select for p66 mutants with restored dimerization, CTY10-5d was cotransformed with a library generated by mutagenesis of p66AlaL234ALex202 and a plasmid expressing either Gal4AD-51 or the Gal4AD-51-L234A mutant. A total of 25,000 colonies from each of two independently mutated libraries were screened. Six and five blue colonies were obtained when lex$_{202}$-Ala-66L234A was cotransformed with Gal4AD-51 and Gal4AD-51-L234A, respectively. CTY10-5d was retransformed with each isolated library plasmid and with either p51HXGADNOT or p51L234AGADNOT; the recovered clones showed restored binding activity with both p51 fusion proteins. Five types of mutations were observed (Table 3). Single amino acid changes in the clones that retained the L234A change included D110G, D186V, W402R and W406R. The remaining three clones had reverted to wild-type at codon 234 (Table 3).

TABLE 3

Second site mutations in lexA$_{202}$66HXL234A that restore dimerization to p51

| | | β-gal activity | |
|---|---|---|---|
| Constructs | Number of Clones | Colony* | Liquid† |
| Wild Type | NA | +++ | 3.2 |
| L234A | NA | − | 0.1 |
| D110G | NA | +++ | 6.9 |
| W402R | NA | +++ | 7.1 |
| W406R | NA | +++ | 5.8 |
| L234A; D110G | 3 | +++ | 1.5 |
| L234A; D186V | 1 | +/− | 0.2 |
| L234A; W402R | 3 | +++ | 7.1 |
| L234A; W406R | 1 | +++ | 6.1 |
| L234 | 3 | +++ | 4.7 |

Yeast strain CTY10-5d was cotransformed with p51HXGADNOT and various clones expressing lexA$_{202}$-Ala-66HX fusions with mutations in p66 as indicated. NA, not applicable.
*As defined in Table 1.
‡As defined in Table 1.

Figure 5:
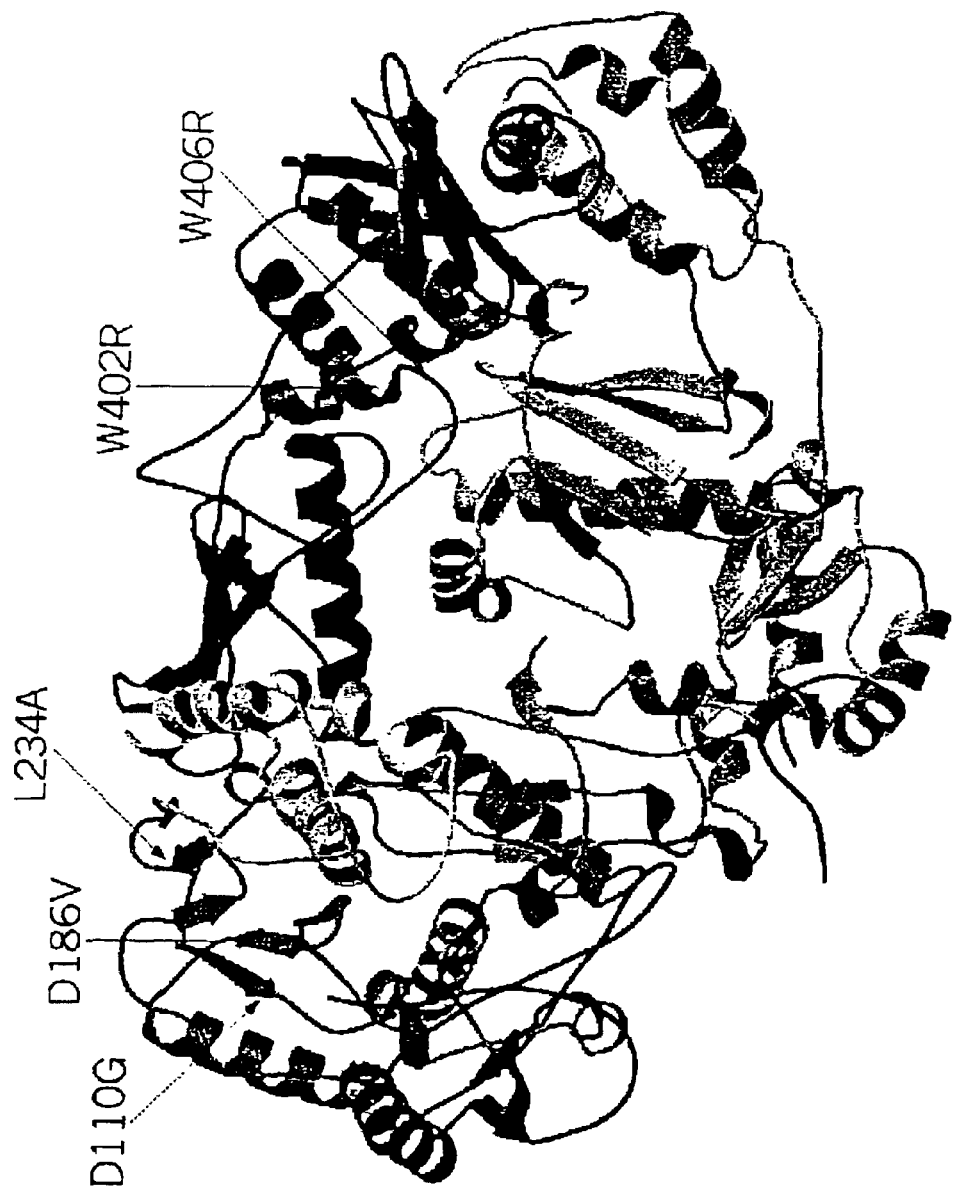

Two of the changes are at the catalytically essential aspartyl residues D110 and D186. These residues are not located at the dimer interface, and mutations at these residues result in an inactive RT (28) (FIG. 5). A variant p66 containing D110G alone, without L234A, gave a 2-fold stronger β-gal signal than wild-type p66 for heterodimerization and was 4.6-fold stronger compared with clones containing both L234A and D110G. Partial restoration of dimerization by D110G suggests that conformational changes at the active site compensate for structural changes mediated by L234A.

The second set of mutations, W402R and W406R, are located at the dimer interface (FIG. 5) in a tryptophan repeat region which is highly conserved among HIV-1, HIV-2 and closely related simian immunodeficiency virus RTs (29). In the L234A genetic background, these mutations resulted in a dramatic increase in the β-gal signal over the parent and yielded a 2-fold higher signal for heterodimerization compared with wild-type RT fusions (Table 3). W402R and W406R in a wild-type genetic background had the same enhanced β-gal activity as the restored mutants (Table 3). Therefore, the mutations in the tryptophan repeat motif may enhance the interaction with GAL4AD-51 independently of the L234A mediated defect.

Figure 6:
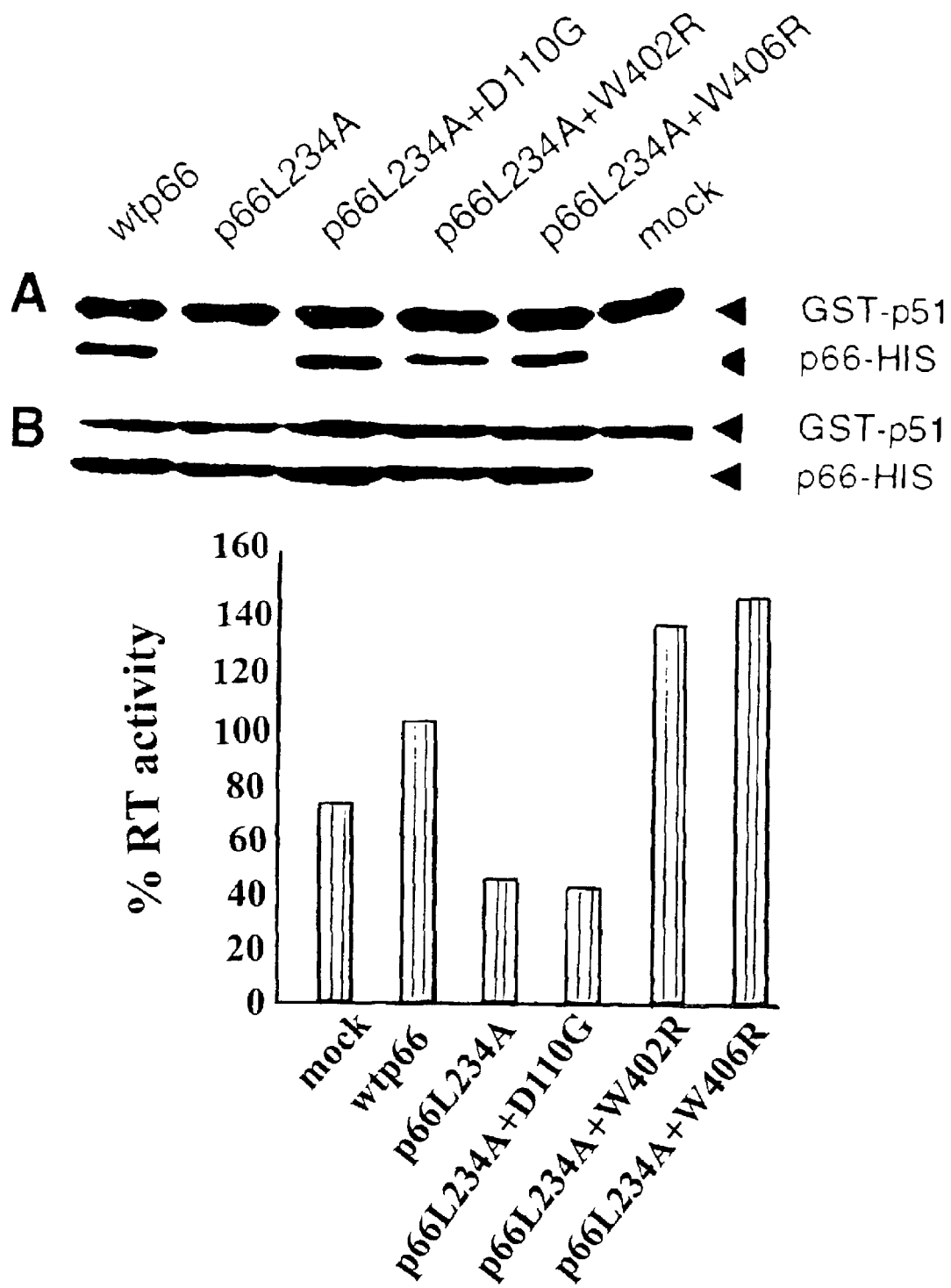

To confirm that the second-site mutations could restore heterodimerization to the L234A parent in an alternative assay, we examined the binding of these p66 mutants to p51 in vitro. Bacterial lysates containing GST-p51 or wild-type and mutant p66-His were incubated together, and heterodimers were captured on Glutathione Sepharose 4B beads. As expected, wild-type p66 dimerized with GST-p51 whereas the p66L234A mutant did not (FIG. 6A). Restoration of dimerization by D110G, W402R or W406R in the L234A parent was observed (FIG. 6A), thus confirming our observations in the Y2H assay.

To determine whether restoration of heterodimerization was associated with enhanced DNA polymerase activity, heterodimers eluted from beads were assayed for RT activity (FIG. 6C). GST-p51 had significant background activity compared with wild-type enzyme. The enzyme resulting from incubation with p66L234A had the same background activity. As expected, heterodimers comprising p66L234A containing the active site mutation D110G also had only background activity. Interestingly, both W402R and W406R mutations not only restored heterodimerization to the L234A parent but also increased RT activity, even above levels of the wild-type control (FIG. 6C).

Discussion

In this study we have shown that fusions of p66 and p51 can be stably expressed in yeast and can heterodimerize in reciprocal configurations. The presence of spacers in the form of alanine or an HA tag may have been an important aspect for stronger interactions in the Y2H assay. Moreover, we have validated the Y2H assay by comparing previously described effects of p51 deletions and the L234A substitution on heterodimerization. We have also shown how this assay can further the study of the HIV-1 RT structure-function by the identification of second-site mutations that restore RT dimerization.

The palm, connection, and RNase H domains of p66 make major contacts with p51. An indication that the palm region is important is the destabilization of the p66/p51 heterodimer by the nonnucleoside RT inhibitor 2', 5'-bis-O-(tert-butylidimethylsilyl)-3'-spiro-5"-4"-amino-1', 2"-oxothiole-2",2"-dioxide)]-b-D-pentofuranosyl (TSAO) by its interaction between the palm subdomain of p66 and the β7-β8 loop in the fingers subdomain of p51 (30, 31). Preliminary tests of the addition of TSAO to our in vitro binding assays confirm the ability of the drug to reduce heterodimerization (data not shown). Tests of the related drug TSAOe$^3$T showed a more modest destabilization only detectable in the presence of denaturants (31). Deletion mapping of the p66 domains required for interaction with p51 suggests that the presence of the connection and RNase H domains are sufficient for interaction with p51 in the Y2H system. It is surprising that the deletion of the palm domain had little effect on binding to p51 as this p66 subdomain provides a major contact with p51 (9); however, the connection and RNase H domains may provide a sufficient surface for saturating the signal in yeast.

Truncation of the C terminus of p51 revealed that a 13-amino acid deletion had little effect on dimerization with p66, but a deletion of 26 amino acids abrogated heterodimerization as seen in the Y2H assay. These data are consistent with previous in vitro studies (15). All C-terminal truncation mutants were stably expressed in yeast, excluding the possibility of decreased expression affecting the signal. It is possible that these C-terminal residues may have a direct role in dimerization; or the deletion of these residues may effect the structural integrity or correct positioning of the structural elements α-L and β-20 (5,15). These elements contain the tryptophan repeat motif, which has been proposed to play an important role in HIV-1 dimerization (29, 32).

We have shown that the L234A substitution inhibits RT dimerization in yeast most dramatically when present on the p66 subunit of HIV-1 RT, as previously seen in vitro (10). L234A is located in the primer grip region of p66 (5) and is highly conserved among avian, primate and murine RTs (33). To help determine the mechanism by which L234A affects heterodimerization, we selected for second-site mutations restoring p66/p51 association. Aside from clones which had reverted to the wild-type L234, we observed two classes of mutants: those with alterations either in the tryptophan repeat or in the polymerase active site (FIG. 5). Both classes of suppressors were also shown to restore binding of the mutant p66 subunit to p51 as measured in an in vitro binding assay (FIG. 6A). L234A is not at the dimer interface, and it has been proposed that it affects dimerization by indirectly affecting contacts between P95 in the palm of p66 with residues in the β7-β8 loop of p51 (11). The mutations W402R and W406R are distant from this region, being located in the connection subdomain which contacts the p51 connection domain in the heterodimer. The appearance of a basic residue in both codon 402 and 406 suggests a charge interaction with an acidic residue in p51 or alternatively an increase in electrostatic potential between the surfaces at the connection domain interface.

The recovery of second-site suppressor mutations at the catalytically essential aspartyl residues suggests that there is a relationship between dimerization and active site residues. Neither D186V nor D110G make obvious contacts with L234A, although both are in the same palm subdomain (FIG. 5)(2). Interaction between the NNRTI binding site, which includes L234, and the RT catalytic site has been suggested by both structural and enzymatic data explaining the mechanism of resistance to NNRTIs (34, 35). The D110G or D186V changes would probably result in loss of one of the two magnesium ions bound to the active site (36). A loss of chelated magnesium in addition to a glycine change at 110 may lead to increased flexibility in that region, thus affecting dimerization. Determination of the crystal structure of the D110G RT mutant will help resolve these issues.

Heterodimerization of HIV-1 has been suggested as a target for chemotherapeutic intervention (7). To date, there are no HIV-1 RT dimerization inhibitors being used in the clinic. Nevertheless, there are several reports of HIV-1 and HIV-2 RT dimerization inhibitors based on peptides representing the conserved tryptophan repeat region of RT (32, 37). These peptides have been shown to prevent the association of p66/p51 (32) and have demonstrable in vitro anti-HIV-1 activity (37). TSAO has been shown to destabilize the p66/p51 heterodimer and may represent a nonpeptide RT dimerization inhibitor (30). In preliminary tests of this drug for its effects on heterodimerization in the Y2H system, we saw no inhibition of β-gal activity (data not shown). However, the possibility that the drug is not taken up by yeast cannot be ruled out. The availability of a Y2H assay for RT dimerization will facilitate the screening for other such inhibitors of this process according to the methods set forth herein.

REFERENCES FOR FIRST SERIES OF EXPERIMENTS 1. di Marzo Veronese, F., Copeland, T. D., DeVico, A. L., Rahman, R., Oroszlan, S., Gallo, R. C. & Sarngadharan, M. G. (1986) Science 231, 1289–1291.
2. Rodgers, D. W., Gamblin, S. J., Harris, B. A., Ray, S., Culp, J. S., Hellmig, B., Woolf, D. J., Debouck, C. & Harrison, S.C. (1995) Proc. Natl. Acad. Sci. USA 92, 1222–1226.
3. Ren, J., Esnouf, R., Garman, E., Somers, D., Ross, C., Kirby, I., Keeling, J., Darby, G., Jones, Y., Stuart, D., et al. (1995) Nat. Struct. Biol. 2, 293–302.
4. Huang, H., Chopra, R., Verdine, G. L. & Harrison, S. C. (1998) Science 282, 1669–1675.
5. Jacobo-Molina, A., Ding, J., Nanni, R. G., Clark, A. D., Jr., Lu, X., Tantillo, C., Williams, R. L., Kamer, G., Ferris, A. L., Clark, P., et al. (1993) Proc. Natl. Acad. Sci. USA 90, 6320–6324.
6. Kohlstaedt, L. A., Wang, J., Friedman, J. M., Rice, P. A. & Steitz, T. A. (1992) Science 256, 1783–1790.
7. Restle, T., Muller, B. & Goody, R. S. (1990) J. Biol. Chem. 265, 8986–8988.
8. Becerra, S. P., Kumar, A., Lewis, M. S., Widen, S. G., Abbotts, J., Karawya, E. M., Hughes, S. H., Shiloach, J. & Wilson, S. H. (1991) Biochemistry 30, 11707–11719.
9. Wang, J., Smerdon, S. J., Jager, J., Kohlstaedt, L. A., Rice, P. A., Friedman, J. M. & Steitz, T. A. (1994) Proc. Natl. Acad. Sci. USA 91, 7242–7246.
10. Ghosh, M., Jacques, P. S., Rodgers, D. W., Ottman, M., Darlix, J. L. & Le Grice, S. F. (1996) Biochemistry 35, 8553–8562.
11. Wohrl, B. M., Krebs, R., Thrall, S. H., Le Grice, S. F. J., Scheidig, A. J. & Goody, R. S. (1997) J. Biol. Chem. 272, 17581–17587.
12. Goel, R., Beard, W. A., Kumar, A., Casas-Finet, J. R., Strub, M. P., Stahl, S. J., Lewis, M. S., Bebenek, K., Becerra, S. P., Kunkel, T. A., et al. (1993) Biochemistry 32, 13012–13018.
13. Divita, G., Restle, T. & Goody, R. S. (1993) FEBS Lett. 324, 153–158.
14. Debyser, Z. & De Clercq, E. (1996) Protein Sci. 5, 278–286.
15. Jacques, P. S., Wohrl, B. M., Howard, K. J. & Le Grice, S. F. (1994) J. Biol. Chem. 269, 1388–1393.
16. Fields, S. & Song, 0. (1989) Nature (London)340, 245–246.
17. Kalpana, G. V. & Goff, S. P. (1993) Proc. Natl. Acad. Sci. USA 90, 10593–10597.
18. Luban, J., Bossolt, K. L., Franke, E. K., Kalpana, G. V. & Goff, S. P. (1993) Cell 73, 1067–1078.
19. Rose, M. D., Winston, F. & Hieter, P. (1990) Methods in Yeast Genetics: A Laboratory Course Manual (Cold Spring Harbor Laboratory Press, New York),
20. Szilvay, A. M., Nornes, S., Haugan, I. R., Olsen, L., Prasad, V. R., Endresen, C., Goff, S. P. & Helland, D. E. (1992) J. Acquired Immune Defic. Syndr. 5, 647–657.
21. Telesnitsky, A., Blain, S. & Goff, S. P. (1995) Methods Enzymol. 262, 347–362. 22. Hanes, S. D. & Brent, R. (1989) Cell 57, 1275–1283.
23. Ruden, D. M., Ma, J., Li, Y., Wood, K. & Ptashne, M. (1991) Nature (London) 350, 250–252.
24. Legrain, P., Dokhelar, M. C. & Transy, C. (1994) Nucleic Acids Res. 22, 3241–3242. 25. Maldarelli, F., Martin, M. A. & Strebel, K. (1991) J. Virol. 65, 5732–5743.
26. Ratner, L., Haseltine, W., Patarca, R., Livak, K. J., Starcich, B., Josephs, S. F., Doran, E. R., Rafalski, J. A., Whitehorn, E. A., Baumeister, K., et al. (1985) Nature (London) 313, 277–284.
27. Maier, G., Dietrich, U., Panhans, B., Schroder, B., Rubsamen-Waigmann, H., Cellai, L., Hermann, T. & Heumann, H. (1999) Eur. J. Biochem. 261, 10–18.
28. Larder, B. A., Purifoy, D. J., Powell, K. L. & Darby, G. (1987) Nature (London) 327, 716–717.
29. Baillon, J. G., Nashed, N. T., Kumar, A., Wilson, S. H. & Jerina, D. M. (1991) New Biol. 3, 1015–1019.
30. Harris, D., Lee, R., Misra, H. S., Pandey, P. K. & Pandey, V. N. (1998) Biochemistry 37, 5903–5908.
31. Sluis-Cremer, N., Dmitrienko, G. I., Balzarini, J., Camarasa, M. J. & Parniak, M. A. (2000) Biochemistry 39, 1427–1433.

32. Divita, G., Restle, T., Goody, R. S., Chermann, J. C. & Baillon, J. G. (1994) J. Biol. Chem. 269, 13080–13083.
33. Georgiadis, M. M., Jessen, S. M., Ogata, C. M., Telesnitsky, A., Goff, S. P. & Hendrickson, W. A. (1995) Structure (London) 3, 879–892.
34. Esnouf, R., Ren, J., Ross, C., Jones, Y., Stammers, D. & Stuart, D. (1995) Nat. Struct. Biol. 2, 303–308.
35. Spence, R. A., Kati, W. M., Anderson, K. S. & Johnson, K. A. (1995) Science 267, 988–993.
36. Patel, P. H., Jacobo-Molina, A., Ding, J., Tantillo, C., Clark, A. D., Jr., Raag, R., Nanni, R. G., Hughes, S. H. & Arnold, E. (1995) Biochemistry 34, 5351–5363.
37. Morris, M. C., Robert-Hebmann, V., Chaloin, L., Mery, J., Heitz, F., Devaux, C., Goody, R. S. & Divita, G. (1999) J. Biol. Chem. 274, 24941–24946.
38. Kraulis, P. J. (1991) J. Appl. Crystallogr. 24, 946–950.
39. Merrit, E. A. & Bacon, D. J. (1997) Methods Enzymol. 277, 505–524.
40. Kabsch, W. & Sander, C. (1983) Biopolymers 22, 2577–2637.

SECOND SERIES OF EXPERIMENTS

Nonnucleoside reverse transcriptase inhibitors (NNRTIs) are allosteric inhibitors of the human immunodeficiency virus type 1 (HIV-1) reverse transcriptase (RT). Yeast grown in the presence of many of these drugs exhibited dramatically increased association of the p66 and p51 subunits of the HIV-1 RT as reported by a yeast two-hybrid assay. The enhancement required drug binding by RT; introduction of a drug-resistance mutation into the p66 construct negated the enhancement effect. The drugs could also induce heterodimerization of dimerization defective mutants. Coimmunoprecipitation of RT subunits from yeast lysates confirmed the induction of heterodimer formation by the drugs. In vitro binding studies indicate that NNRTIs can bind tightly to p66 but not p51, and then mediate subsequent heterodimerization. This study demonstrates a novel effect of NNRTIs on the assembly of RT subunits.

The human immunodeficiency virus type 1 (HIV-1) reverse transcriptase (RT) catalyzes the conversion of genomic RNA into double-stranded proviral DNA after cell entry (1), utilizing the RNA- and DNA-dependent polymerase and ribonuclease H (RNase H) activities of the enzyme. The HIV-1 RT is an asymmetric dimer consisting of p66 and p51 polypeptides (2, 3). The p51 subunit contains the identical N-terminal sequences as p66, but lacks the C-terminal RNase H domain. The structure of the HIV-1 RT has been elucidated by X-ray crystallography in several forms including the unliganded enzyme (4), in complex with nonnucleoside reverse transcriptase inhibitors (NNRTIs) (5, 6) and bound to template-primer with (7) or without dNTP substrate (8). The polymerase domain of the p66 subunit resembles a right hand and contains the fingers, palm, thumb and connection subdomains, with the latter acting as a tether between the polymerase and RNase H regions (5, 8). Although p51 has the same polymerase domains as p66, the relative orientations of these individual domains differ markedly (5, 8). Structural analysis reveals three major contacts between p66 and p51, with most of the interaction surfaces being hydrophobic (9, 10).

NNRTIs are chemically diverse, largely hydrophobic compounds which comprise over 30 different classes (11, 12). NNRTIs do not require intracellular metabolism for activity, are noncompetitive inhibitors of RT activity with respect to dNTP substrate and template/primer, and are relatively noncytotoxic (11). NNRTIs bind to a hydrophobic pocket close to but distinct from the polymerase active site in the p66 subunit (13, 14) and inhibit enzyme activity by mediating allosteric changes in the RT (15, 16). Initial clinical use of NNRTIs as monotherapy and selection of drug-resistant variants in cell culture results in the rapid emergence of highly drug-resistant variants due to single amino acid changes (17, 18) in the NNRTI binding pocket that directly affect drug binding (13, 14). The NNRTIs currently approved for use in highly active antiretroviral therapy include nevirapine (19), delavirdine (20) and efavirenz (21). We have previously shown that HIV-1 RT heterodimerization can be effectively monitored in the yeast two-hybrid (Y2H) system using appropriately engineered constructs (22). We used this system to assess the effect of NNRTIs on the b-galactosidase (b-gal) readout in yeast. Several NNRTIs induced dramatic increases in b-gal activity and this increase was due to enhanced association between the RT subunits as a result of a specific interaction of drug with the p66 subunit. These data document a novel effect of NNRTIs on HIV-1 RT dimerization and demonstrate that these drugs behave in a manner similar to chemical inducers of dimerization (CID), compounds that bind to a target protein and promote an interaction with another protein (23).

Materials and Methods

Antiviral drugs

The drugs used in this study were: carboxanilides UC781, UC10, UC38, UC84 (24, 25), Uniroyal Chemical Ltd (Middlebury, Conn.); efavirenz (EFV) (21), DuPont Merck (Wilmington Del.); delavirdine (BHAP) (26), Pharmacia and Upjohn (Kalamazoo, Mich.); nevirapine (19), Roxanne Laboratories (Redding Conn.); HBY 097 (27), Hoechst-Bayer (Frankfurt, Germany); 8-chloro-TIBO (8-Cl-TIBO) (28) and a-APA (29), Janssen Research Foundation (Beerse, Belgium). All drugs were dissolved in dimethyl sulfoxide at a concentration of 10 mg/ml for use in Y2H and in vitro assays.

Yeast and Bacterial Strains and Yeast Methods

Yeast and bacterial strains were as described previously (22). Transformation of yeast, the qualitative b-gal colony lift assay and the quantitative b-gal liquid assay were as previously described (22).

Construction of HIV-1 RT Fusions in Yeast Expression Vectors

The construction of p66SH2-1, p51SH2-1, p66GADNOT, p51GADNOT and p51ACTII which express the wild type p66 and p51 fusion proteins lexA$_{87}$-66, lexA87-51, Gal4AD-66, Gal4AD-51 and Gal4AD-HA-51, respectively were as described previously (22). p66L234ASH2-1 (encoding lexA$_{87}$-66L234A) was made by cloning the PCR amplification product from the RT region of p66AlaL234ALex202 (22) into the BamHI-SalI sites of pSH2-1. p51234ACTII (encoding Gal4AD-HA-51L234A) was constructed by subcloning the p51 BamHI-SalI fragment from p51234GADNOT (22) into pACTII. p66W401ASH2-1 (encoding lexA$_{87}$-66W401A), p51W401AACTII (encoding Gal4AD-HA-51W401A) and p51W401AGADNOT (encoding Gal4AD-51W401A) were made by PCR amplification of the RT region from plasmid pALRT-78S(A402) (a gift from John McCoy) and cloned into the BamHI-SalI sites of pSH2-1, pGADNOT or the BamHI-XhoI sites of PACTII. p66Y181CSH2-1 containing the Y181C mutation in p66 of the lexA$_{87}$-66 fusion protein was prepared by site-directed mutagenesis using the Gene Editor Kit (Promega, Madison, Wis.) according to the manufacturer's protocol.

Construction of HIV-1 RT Fusions in Bacterial Expression Vectors

Wild-type and p66 mutants (either L234A or W401A) were cloned into the SphI-BglII site of pQE-70 (Qiagen, Chatsworth, Calif.) (22). Glutathione S-transferase-tagged p51 (GST-p51) and mutants containing either the W401A or L234A substitutions were constructed by cloning the p51 encoding fragments into the BamHI-SalI site of pGEX5X-3 (Amersham Pharmacia Biotech) (22).

Y2H RT Heterodimerization Assays for Measuring Effect of NNRTIs on B-Gal Activity.

CTY10-5d transformed constructs expressing p66 bait and p51 prey fusions were grown overnight to stationary phase in synthetic complete medium without histidine and leucine and containing 2% glucose (SC-His-Leu). 2.5 ml of media with or without drug were inoculated with 0.0125–0.25 $OD_{600}$ units of CTY10-5d. Yeast were grown with aeration at 30° C. to $OD_{600}$=0.5. The equivalent of 1 $OD_{600}$ unit was pelleted for each treatment and subjected to a quantitative b-gal liquid assay.

Coimmunoprecipitation of p66 and p51 in Yeast Lysates.

Cultures (30 ml) containing no drug, efavirenz or UC781 and 0.1 $OD_{600}$ units/ml of CTY10-5d expressing p66 bait and p51 prey fusions were grown in SC-His-Leu to $OD_{600}$= 0.5 at 30° C. Cells were normalized to 12 $OD_{600}$ units and washed with 10 ml of TE (10 mM Tris pH 7.5; 1 mM EDTA) buffer. Preparation of protein extracts and immunoprecipitation were as previously described (30) except for the use of anti-HA.11 monoclonal antibodies (clone 16B12; Covance, Princeton, N.J.) and Protein G-PLUS agarose beads (Santa Cruz Biotechnology; Santa Cruz, Calif.). Samples were resolved by SDS-PAGE. The $leXA_{87}$-66 fusion protein was probed using monoclonal antibodies 7E5 which specifically detects p66 (31).

In vitro heterodimerization in the presence of NNRTIs

The heterodimerization of bacterially expressed wild-type p66-His and GST-p51 (or mutants) was assessed in bacterial lysates as described previously (22). To determine the capacity of efavirenz to bind to a particular RT subunit, 500 μl reactions in lysis buffer (without NP-40) (22), 5 μg of p66-His, 5 μg GST-p51 or no recombinant protein (total protein concentration was 0.8 μg/ml in each reaction) were incubated overnight at 40° C. with increasing concentrations of efavirenz. Lysates were washed 4 times with lysis buffer using a centricon-YM-50 filter device (Millipore Corporation, Bedford, Mass.) to remove unbound drug. 5 μg of the corresponding RT subunit was applied to the washed lysates (in 500 μl) and incubated for 1.5 hr at 40° C. Heterodimers were captured onto beads (22), resolved by SDS/PAGE and detected using RT antibodies (monoclonal antibody 5B2) (31).

Results

Enhancement of B-Gal Activity by NNRTIs

To test the effects of NNRTIs on the association of the RT polypeptides we used a yeast genetic assay that measures RT heterodimerization (22). In this assay yeast expressing the p66 subunit of the HIV-1 RT fused to the C-terminus of $lexA_{87}$ ($lexA_{87}$-66) and the p51 subunit fused to the Gal4AD (Gal4AD-51) constitutively interact, resulting in the activation of the expression from an integrated Lac Z reporter gene. To test for the effects of the NNRTIs on this interaction, 10 drugs representing 7 different NNRTI classes were added to the culture medium during growth of the yeast and b-gal levels were determined. Of the 10 NNRTIs tested, 9 demonstrated a dramatic concentration-dependent enhancement of b-gal activity compared to cells not treated with drug (FIGS. 7A and 7B). No significant toxicity, as determined by the growth rate, was observed for the drug concentrations tested compared to untreated controls (results not shown). Efavirenz was the most potent of the compounds, mediating a 40-fold increase in b-gal activity at the highest drug concentration tested (FIG. 7A). The carboxanilide UC781 was the second most potent drug, followed by UC10 and a quinoxaline, HBY 097 (FIGS. 7A and 7B). The remainder of the NNRTIs were less potent but still displayed 8–10 fold increases in b-gal activity at the highest concentrations tested (FIGS. 7A and 7B). In contrast delaviridine was devoid of b-gal enhancing activity (FIG. 7A).

Enhancement of B-Gal Activity by NNRTIs is Specific for RT Heterodimerization

The specificity of the b-gal enhancement by NNRTIs was investigated. Yeast transformed with the empty vectors pSH2-1 and pGADNOT, which express $lexA_87$ and Gal4AD, respectively were treated with serial dilutions of the most potent b-gal enhancing drug, efavirenz. We observed no increase in b-gal activity even in the presence of 15 μM of drug (data not shown). The capacity of efavirenz to enhance b-gal activity of several unrelated protein-protein interaction pairs, including moloney murine leukemia virus reverse transcriptase with elongation factor release factor 1 (M.O., unpublished), was also examined and no enhancement or inhibition of b-gal activity was observed.

Figure 8:
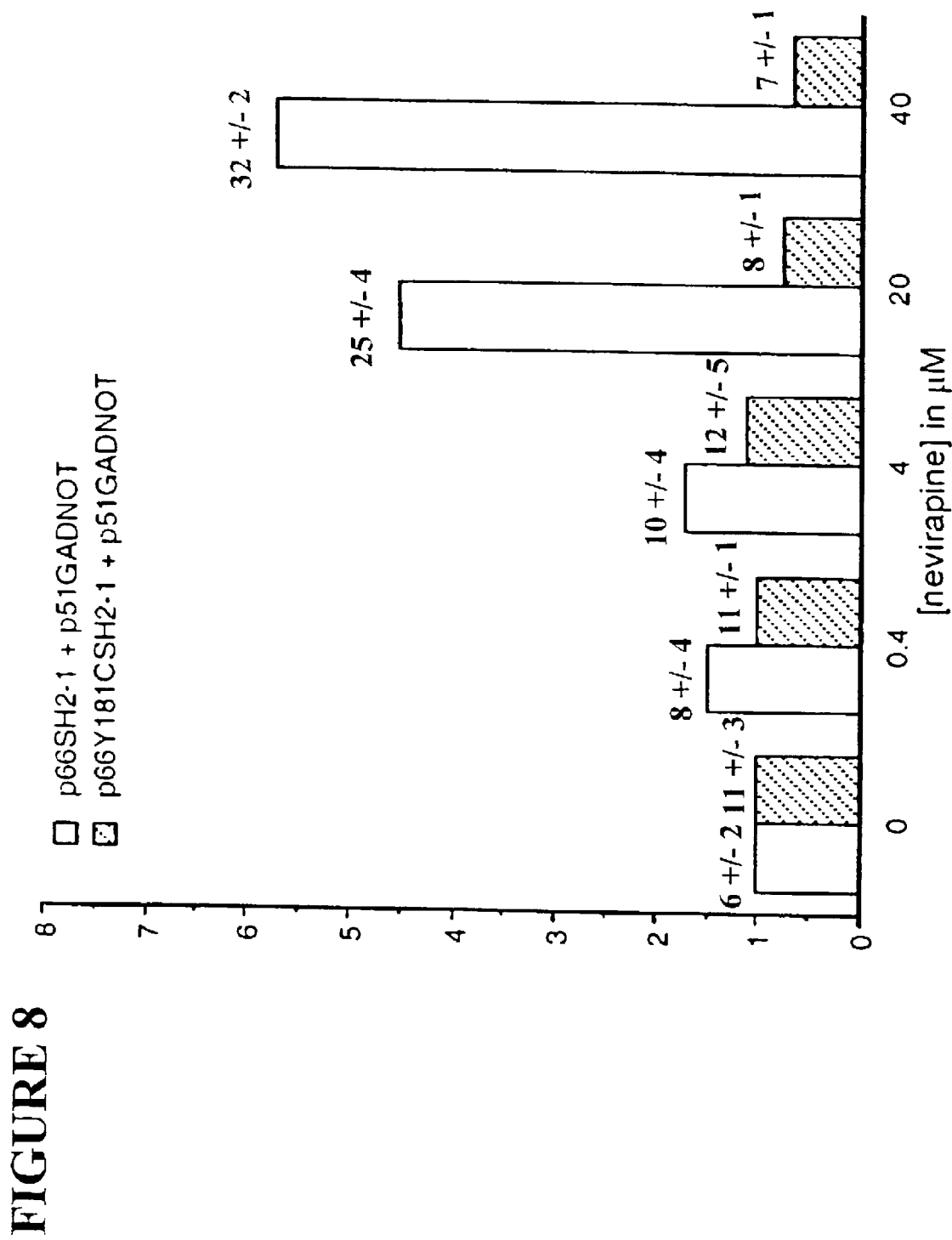

The Y181C mutation in the p66 subunit of the HIV-1 RT confers more than a 100-fold increase in resistance to nevirapine (17). This mutation directly affects drug binding (13, 14). To further establish the specificity of the b-gal enhancement by NNRTIs, Y181C was introduced into the plasmid encoding the $lexA_{87}$-66 fusion protein. Yeast were cotransformed with various pairs of plasmids and grown in the presence of nevirapine. The presence of the Y181C change in the p66 bait totally negated the enhancement effect by nevirapine (FIG. 8). In contrast, a significant level of b-gal enhancement was still retained in the presence of efavirenz (results not shown), consistent with the very low level of resistance conferred by Y181C to this drug. These data provide compelling evidence that the b-gal enhancement effect is due to a specific interaction of nevirapine with the p66 subunit of the HIV-1 RT.

NNRTIs can Enhance B-Gal Activity of Dimerization Defective Mutants

Figure 9:
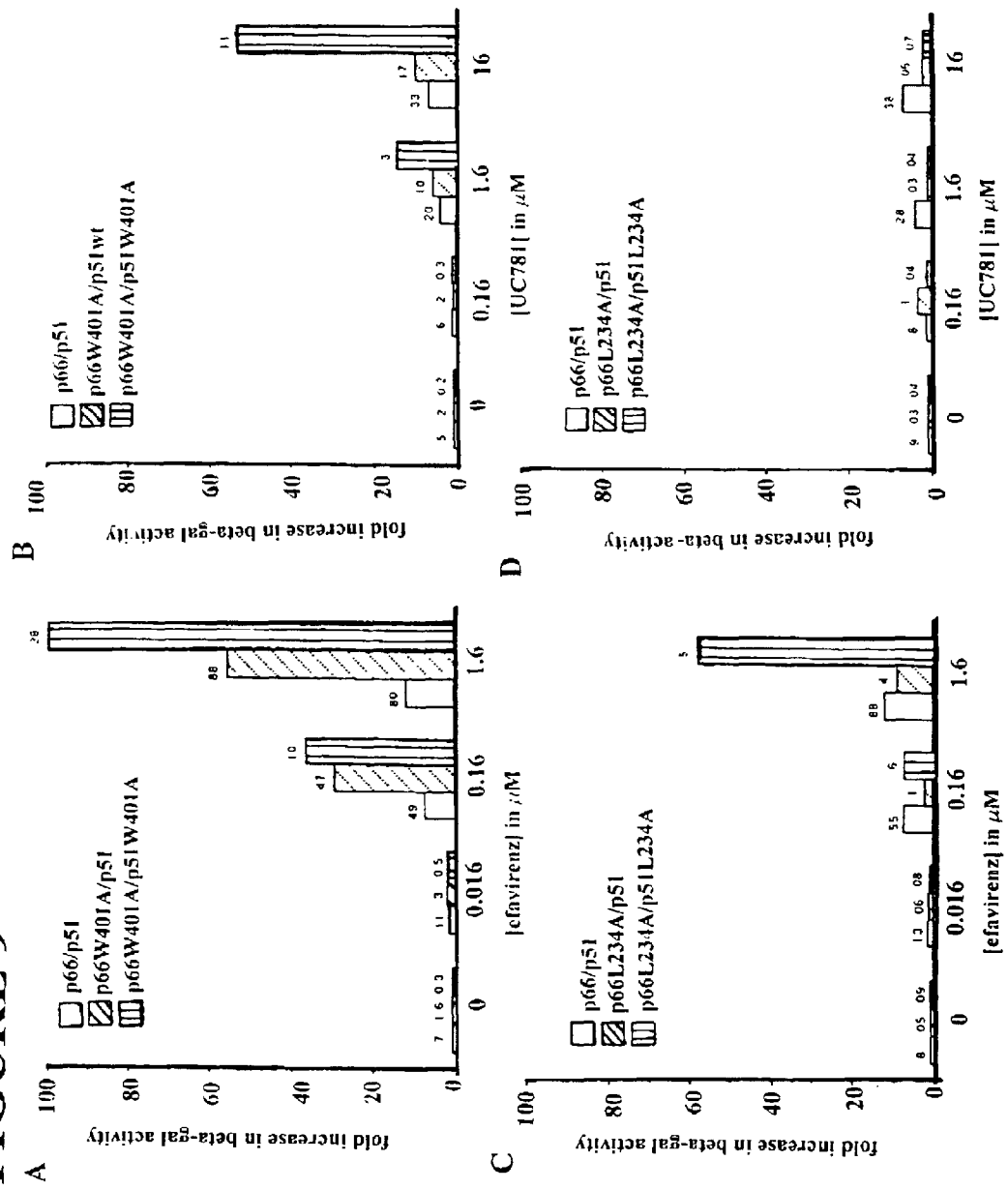

Previous studies have shown that the L234A mutation in HIV-1 RT abrogates RT dimerization (22, 32). Other studies on the role of the tryptophan repeat motif (codons 398–414), present in the connection subdomains of both subunits, showed that the W401A mutation also diminishes RT dimerization in the Y2H assay (G.T. unpublished data). We investigated the effect of the NNRTIs, efavirenz and UC781 on the b-gal enhancement effect on these dimerization defective RT mutants. Interestingly, yeast treated with efavirenz and expressing the W401A change in one or both subunits showed a dramatic increase in b-gal activity compared to no drug (FIG. 9A). b-gal activity in yeast expressing the W401A mutation in both expressing dimerization defective mutants to coimmunoprecipitation. Yeast expressing both p66 bait and p51 prey fusions containing the W401A mutation ($lexA_{87}$-66W401A and Gal4AD-HA-51W401A) or the L234A change ($lexA_{87}$-66L234A and Gal4AD-HA-51L234A) were grown in the presence of efavirenz (1.6 μM), UC781 (16 μM) or no drug. Hemagglutinin (HA) antibodies were used to immunoprecipitate the p51 prey and the presence of any bound p66 bait was then detected using anti-p66 specific antibodies. For coimmunoprecipitation of the p66 bait fusions, samples were divided into two with one part processed without added NNRTI while the other was maintained in drug at the same concentration used during growth of yeast. Yeast grown in the absence of drug was also processed without drug or in the presence of 1.6 μM of efavirenz. A clear increase in the amount of lexA$_{87}$-66W401A and lexA$_{87}$-66L234A associated with the p51 prey was observed for yeast grown in the presence of efavirenz compared to no drug (FIGS. 4A and 4B). Similar experiments with yeast grown in UC781 revealed heterodimer formation for yeast expressing the W401A mutant but not for the L234A mutant; these data corresponding to the levels of b-gal activity in the cells (FIGS. 4A and 4B).

Figure 10:
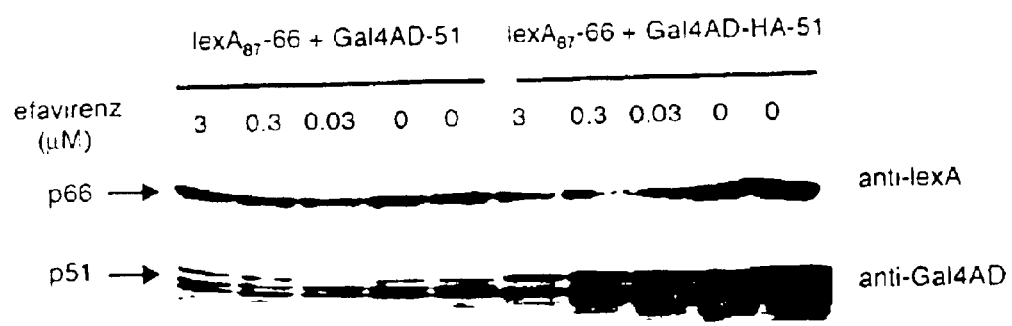

No significant difference in the amount of coimmunoprecipitated p66 bait in the absence or presence of drug was observed indicating that the heterodimer was stable under the conditions of the assay. Interestingly, there was significantly more heterodimer present in yeast lysates obtained from cells grown in the absence of drug to which efavirenz was added during the coimmunoprecipitation procedure for the W401A mutant (FIG. 10A). These data suggest that some heterodimer formation could occur in vitro. Levels of mutant p66 bait and p51 prey fusions present in the original lysate from yeast grown in the absence and presence of drug were similar indicating that the increase in coimmunoprecipitated p66 bait in the presence of drug was not due to increased levels of fusion proteins. It is clear from these experiments that NNRTIs tested do act by inducing heterodimerization of p66 and p51 in the Y2H assay and that the increased dimer formation correlates with the increase in b-gal activity.

Efavirenz Enhances the Association of Wild-Type and Mutant p66 and p51 in Lysates in Vitro To explore whether NNRTIs could enhance dimerization in vitro, bacterial lysates containing either p66-His or GST-p51 were prepared and combined in the presence of increasing concentrations of efavirenz. In the absence of inhibitor a small amount of dimer was present as indicated by detectable amounts of p66-His. A concentration dependent increase in dimer formation was observed in the presence of increasing concentrations of efavirenz (FIG. 11). The enhancement effect of efavirenz on the L234A and W401A mutants was also assessed. Bacterial lysates separately expressing p66L234A-His and GST-p51L234A or p66W401A-His and GST-p51W401A were combined as above and incubated in the presence of increasing concentrations of efavirenz. A significant increase in dimer formation was observed in the presence of a 10-fold molar excess of efavirenz for the W401A mutant (FIG. 11). A 100-fold molar excess of efavirenz over RT was required to induce detectable enhancement of dimerization of the L234A mutant (FIG. 11). These data are consistent with the coimmunoprecipitation experiments and indicate that the enhancement of dimerization by efavirenz is due to its specific interaction with the HIV-1 RT and not dependent on the fusion proteins used in the Y2H assay nor on components present in the yeast cells in vivo.

Other NNRTIs Enhance Heterodimerization of RT Subunits in Vitro

Figure 7:
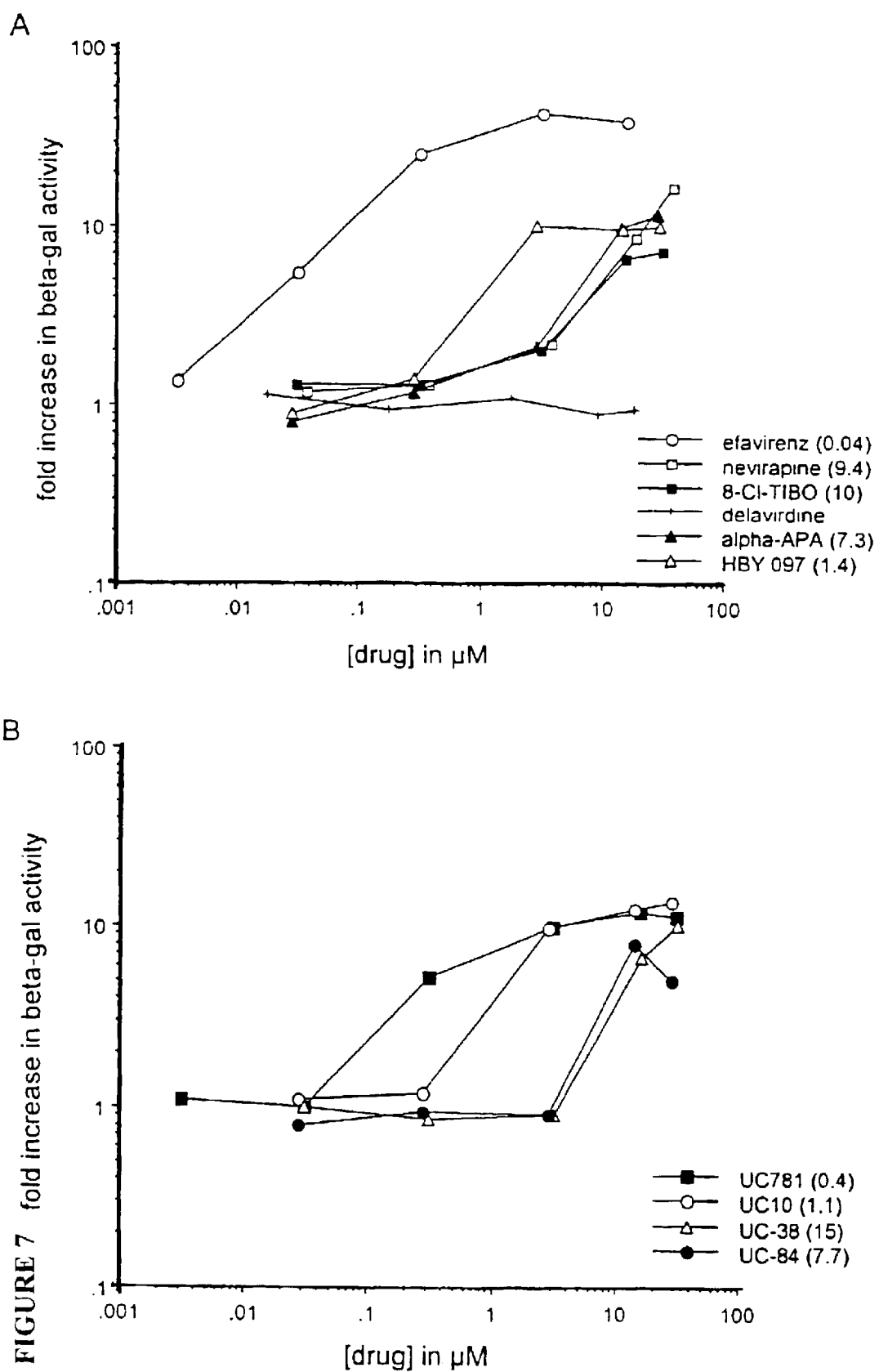
Figure 12:
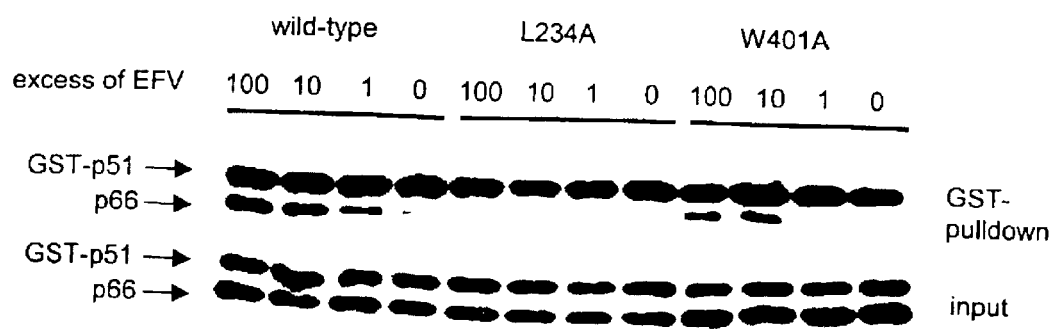

We extended our in vitro study by testing the remaining NNRTIs for their capacity to enhance the dimerization of GST-p51 and p66-His in vitro. Consistent with our Y2H data we observed that efavirenz was the most potent enhancer of dimerization. The relative in vitro potencies of the other NNRTIs correlated well with their b-gal enhancing effect in yeast (FIGS. 7 and 12). In contrast, UC781 and UC10 were poor dimerization inducers in bacterial lysates compared with their b-gal enhancing activities. The low dimerization enhancement activity of these drugs may be a function of both their poor solubility and the conditions of the in vitro assay (which was performed at 4° C.). In contrast, the conditions of the yeast assay, which was carried out at 30° C. with agitation, may have facilitated solubilization of UC781 and UC10. Interestingly, delavirdine was also inactive in vitro indicating that the lack of effect in yeast was not a result of the inability of this drug to penetrate the cells.

Efavirenz Enhances Heterodimerization by Binding to p66-His but not GST-p51

Figure 13:
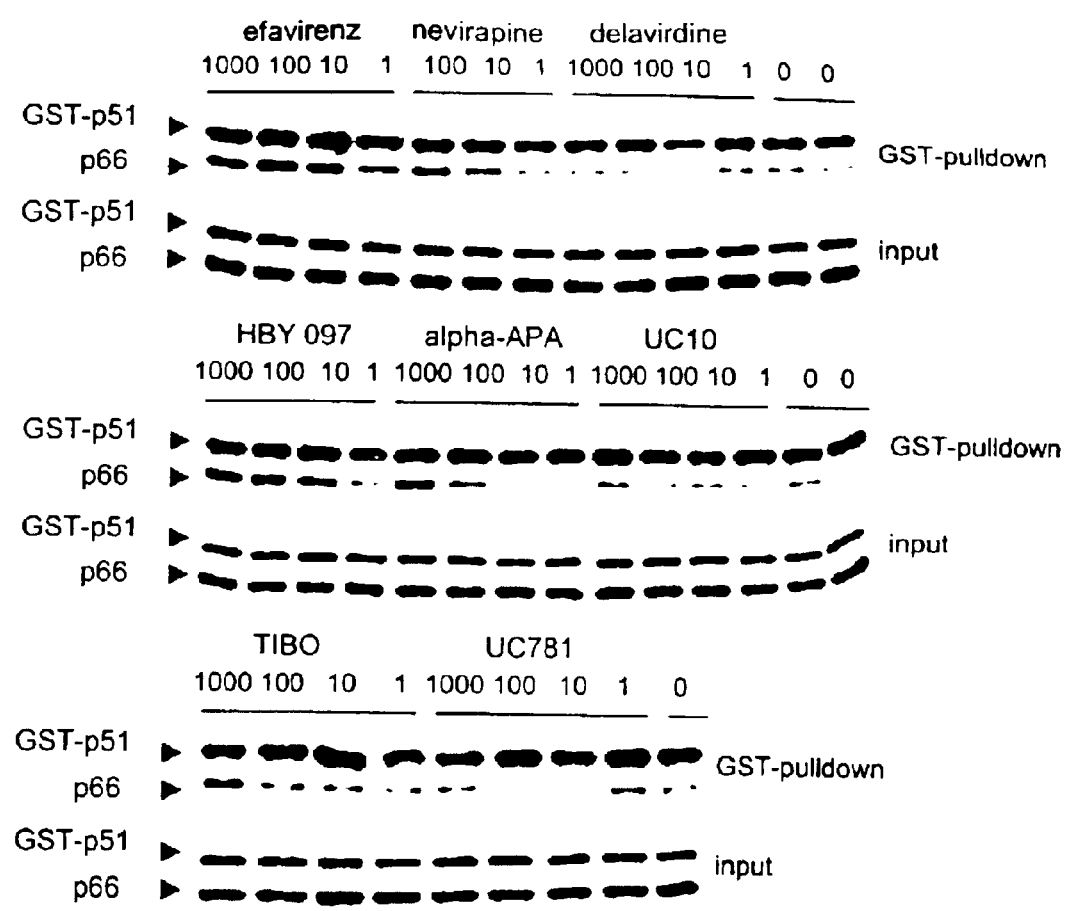

To help elucidate the mechanism by which efavirenz enhances heterodimerization we assessed whether this drug could bind to either p66-His or GST-p51. Bacterial lysates expressing p66-His, GST-p51 or no recombinant protein were preincubated in the absence or presence of increasing concentrations of efavirenz. Unbound drug was removed from the lysates by a series of washes and the presence of any remaining drug was assayed by the addition of the cognate RT subunit. p66-His and GST-p51 was added to a washed mock bacterial lysate to assess the efficiency of efavirenz removal. When p66-His was preincubated with efavirenz we observed enhancement of dimerization with subsequently added GST-p51 at all drug concentrations (FIG. 13). This enhancement was similar to controls where p66-His and GST-p51 were simultaneously combined with various drug concentrations (FIG. 12). A 100-fold reduction in the potency of heterodimerization compared to p66-His preincubated with efavirenz was observed in the washed mock bacterial lysate (FIG. 13). GST-p51 preincubated with drug, washed and then subjected to the functional heterodimerization assay displayed the same pattern of heterodimerization observed for the drug-treated mock bacterial lysate. These data indicate that efavirenz binds tightly to p66-His but not GST-p51 and that this binding then promotes heterodimerization with subsequent added GST-p51.

Discussion

This study reports a previously undescribed property of certain NNRTIs—their capacity to enhance heterodimerization of the p66 and p51 subunits of the HIV-1 RT. This effect was observed both in the Y2H system, detecting dimerization of p66 and p51 using b-gal activity as a readout, and confirmed in coimmunoprecipitation experiments. The phenomenon was also observed in vitro using bacterially expressed GST-p51 and p66-His showing that it is not specific to yeast. NNRTIs were also able to induce the dimerization of the interaction defective mutants L234A and W401A. Furthermore, efavirenz can bind tightly to p66-His and then subsequently promote heterodimerization. The data indicate that NNRTIs have properties similar to conventional CIDs in their capacity to enhance the interaction between two proteins. As the interaction between p66 and p51 occurs naturally and the effect of the NNRTIs is to enhance this interaction then these small molecules are best described as chemical enhancers of dimerization.

Correlation Between in Vitro and in Vivo Enhancement of Heterodimerization by NNRTIs The most potent b-gal enhancing NNRTIs in the Y2H RT dimerization assay were efavirenz, UC781 and HBY 097. These drugs are second generation NNRTIs that are also extremely potent inhibitors of HIV-1 replication in vitro (21, 25, 27). Efavirenz and UC781 differ from the other NNRTIs in that they bind very tightly to the RT heterodimer and exhibit very slow dissociation rates ($k_{off}$) (34, 35). The tight binding properties of efavirenz and UC781 may in part have contributed to their potency as enhancers of heterodimerization in yeast. There was generally a very good correlation between the relative potency in inducing dimerization of the NNRTIs in vitro and in yeast, with the exception of UC781 and UC10.

Relationship Between Drug Induced Enhancement of Dimerization, Structural Changes in the HIV-1 RT and RT Inhibitory Activity.

Figure 14:
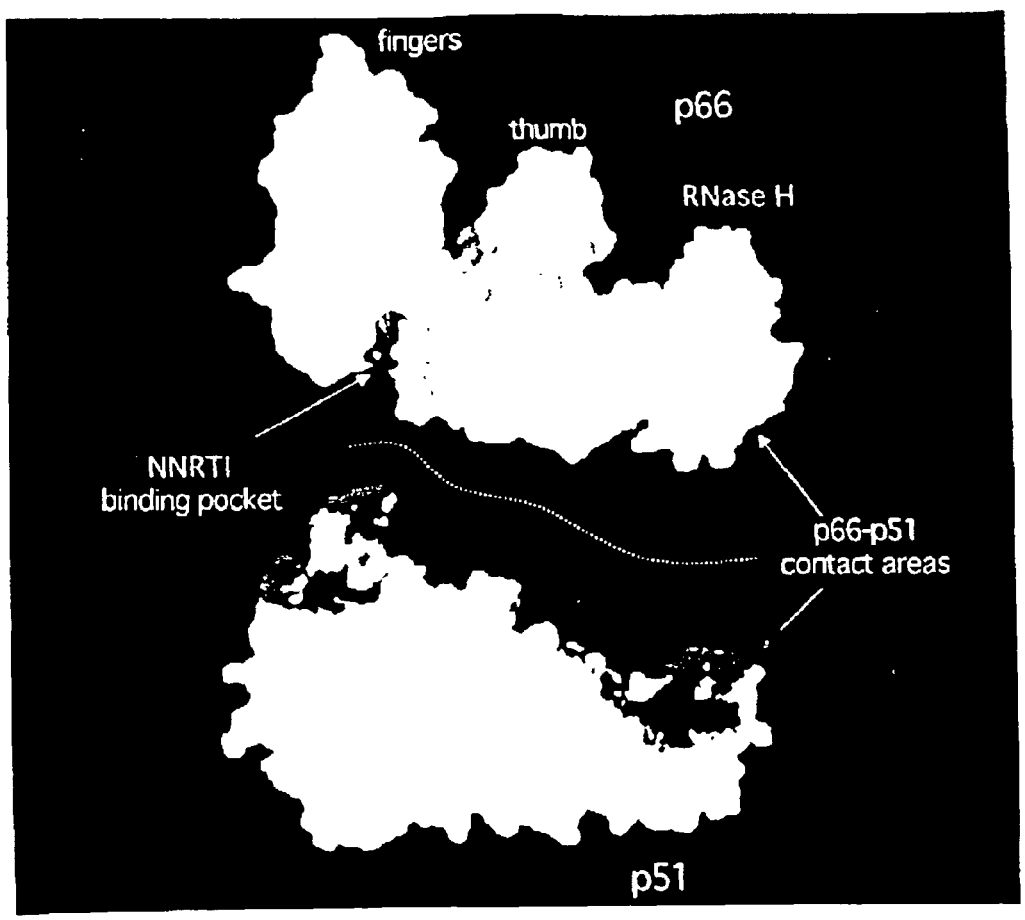

NNRTIs bind in a hydrophobic pocket at the base of the p66 thumb subdomain which is proximal to (~10 Å), but distinct from the polymerase active. It is clear that the size of the NNRTI binding pocket is small compared to the extensive dimer interface (FIG. 14). No strong correlation was found between the extent of the p66/p51 interface (36, 37) in the structures of the HIV-1 RT in complex with several NNRTIs and the drug concentration mediating a 5-fold enhancement of b-gal activity. Thus, the NNRTI effect on heterodimerization is not a simple function of the surface area buried at the interface, and NNRTIs may affect dimerization by other mechanisms in addition to modulating the extent of the contacts. The position of the drug in the pocket and the degree of NNRTI interaction with the p51 subunit were found to vary significantly among the different RT/NNRTI complexes (FIG. 9), and the changes in the vicinity of the bound NNRTIs may also play a role in heterodimer formation.

Figure 15:
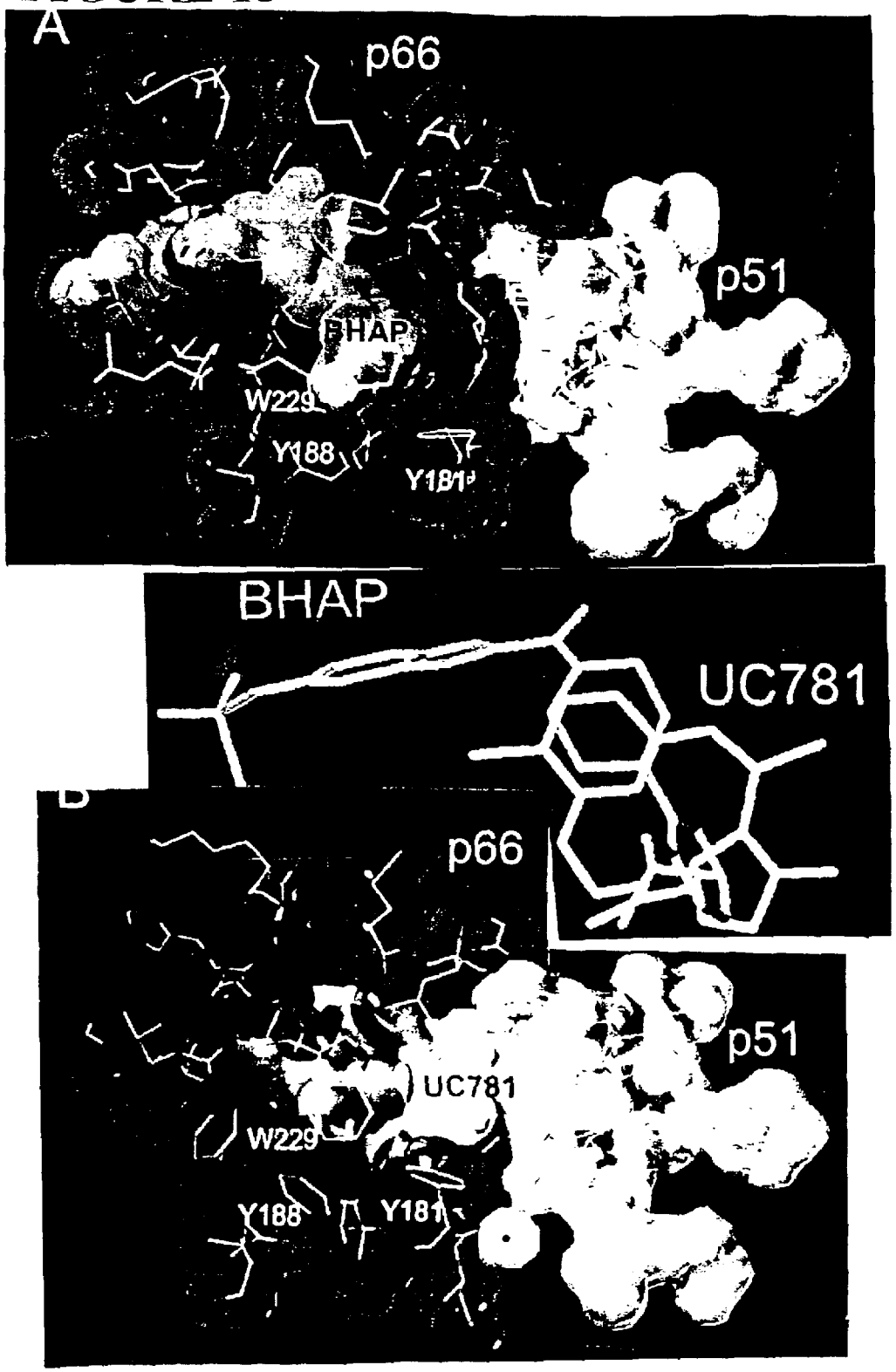

Binding of efavirenz to RT is accompanied by conformational changes in the binding pocket region, and these changes (including at Leu234) (38), may also influence dimer formation. Delavirdine is the longest NNRTI inhibitor and a portion of it protrudes outside the NNRTI binding site causing the largest distortion of the p66 subunit of any of the NNRTIs studied to date (39). Delavirdine binds the furthest away from the p66/p51 interface (closest distance between delavirdine and p51 is 5.1 Å compared to 3.8 Å for UC781) (FIG. 15) The unique characteristics of the interaction of delavirdine with HIV-1 RT suggest that this NNRTI may bind to p66 in a distinctive way that does not favor the enhancement of dimerization.

The relationship between the RT inhibitory activity of the NNRTIs in an exogenous RT assay (50% inhibitory concentration) and the concentration of drug that mediates a 5-fold increase in b-gal activity in the Y2H assay was compared. Efavirenz was the most potent in both assays while UC38 was the least active (results not shown). Examination of the data revealed a fair correlation (r=0.6) between these two parameters suggesting a relationship between the b-gal enhancement effect and RT inhibitory activity in vitro.
Potential Mechanisms for NNRTI Enhancement of Dimerization How might the NNRTIs enhance heterodimerization? One possible model involves NNRTI binding directly to the p66 monomer. Drug binding to monomeric p66 may stabilize a conformation that is more conducive to heterodimer formation, and a more potent NNRTI may effectively increase the concentration of p66 in a conformation that promotes dimerization. Alternatively, efavirenz may cause the p66 monomer to have a conformational flexibility that allows this subunit to more readily undergo structural changes necessary for dimerization. A second model would entail NNRTIs binding only to the heterodimer and as a consequence stabilizing the dimer. The binding could shift the equilibrium toward the dimer. The data suggest that efavirenz binds tightly to p66. However, as bacterially expressed p66 comprises a population of monomers and homodimers it is unclear whether GST-p51 is binding directly to monomeric p66 complexed with drug or is exchanging with one p66 subunit in the drug bound homodimer. Elucidation of the exact mechanism of NNRTI induced enhancement of dimerization will require further studies.

The findings may have biological significance in terms of effects on virus replication. Drug binding to p66 could potentially modulate the interaction between Pr160$^{GagPol}$ precursors which may affect regulation of HIV-1 protease-specific cleavage of this polyprotein. Further, the Y2H RT dimerization assay can potentially be used to screen for NNRTIs with the capacity to bind and mediate the appropriate conformational changes in the p66 subunit that results in enhanced binding to p51. It is possible that novel allosteric inhibitors of RT may be selected using this assay.

REFERENCES FOR SECOND SERIES OF EXPERIMENTS

31. Goff, S. P. (1990) *J. Acquir. Immune Defic. Syndr.* 3, 817–831.
32. di Marzo Veronese, F., Copeland, T. D., DeVico, A. L., Rahman, R., Oroszlan, S., Gallo, R. C. & Sarngadharan, M. G. (1986) *Science* 231, 1289–1291.
33. Le Grice, S. F. J. (1993) in *Reverse Transcriptase*, eds. Skalka, A. M. & Goff, S. P. (Cold Spring Harbor Laboratory Press, Plainview), pp. 163–191.
34. Hsiou, Y., Ding, J., Das, K., Clark, A. D., Jr., Hughes, S. H. & Arnold, E. (1996) *Structure* 4, 853–860.
35. Kohlstaedt, L. A., Wang, J., Friedman, J. M., Rice, P. A. & Steitz, T. A. (1992) *Science* 256, 1783–1790.
36. Das, K., Ding, J., Hsiou, Y., Clark, A. D., Jr., Moereels, H., Koymans, L., Andries, K., Pauwels, R., Janssen, P. A., Boyer, P. L. & et al. (1996) *J. Mol. Biol.* 264, 1085–1100.
37. Huang, H., Chopra, R., Verdine, G. L. & Harrison, S. C. (1998) *Science* 282, 1669–1675.
38. Jacobo-Molina, A., Ding, J., Nanni, R. G., Clark, A. D., Jr., Lu, X., Tantillo, C., Williams, R. L., Kamer, G., Ferris, A. L., Clark, P. & et al. (1993) *Proc. Natl. Acad. Sci. USA* 90, 6320–6324.
39. Becerra, S. P., Kumar, A., Lewis, M. S., Widen, S. G., Abbotts, J., Karawya, E. M., Hughes, S. H., Shiloach, J. & Wilson, S. H. (1991) *Biochemistry* 30, 11707–11719.
40. Wang, J., Smerdon, S. J., Jager, J., Kohlstaedt, L. A., Rice, P. A., Friedman, J. M. & Steitz, T. A. (1994) *Proc. Natl. Acad. Sci. USA* 91, 7242–7246.
41. De Clercq, E. (1998) *Antiviral Res.* 38, 153–179.
42. Pedersen, O. S. & Pedersen, E. B. (1999) *Antivir. Chem. Chemother.* 10, 285–314.
43. Smerdon, S. J., Jager, J., Wang, J., Kohlstaedt, L. A., Chirino, A. J., Friedman, J. M., Rice, P. A. & Steitz, T. A. (1994) *Proc. Natl. Acad. Sci. USA* 91, 3911–3915.
44. Tantillo, C., Ding, J., Jacobo-Molina, A., Nanni, R. G., Boyer, P. L., Hughes, S. H., Pauwels, R., Andries, K., Janssen, P. A. & Arnold, E. (1994) *J. Mol. Biol.* 243, 369–387.
45. Ding, J., Das, K., Tantillo, C., Zhang, W., Clark, A. D., Jr., Jessen, S., Lu, X., Hsiou, Y., Jacobo-Molina, A., Andries, K. & et al. (1995) *Structure* 3, 365–379.
46. Esnouf, R., Ren, J., Ross, C., Jones, Y., Stammers, D. & Stuart, D. (1995) *Nat. Struct. Biol.* 2, 303–308.
47. Richman, D., Shih, C. K., Lowy, I., Rose, J., Prodanovich, P., Goff, S. & Griffin, J. (1991) *Proc. Natl. Acad. Sci. USA* 88, 11241–11245.
48. Richman, D. D., Havlir, D., Corbeil, J., Looney, D., Ignacio, C., Spector, S. A., Sullivan, J., Cheeseman, S., Barringer, K., Pauletti, D. & et al. (1994) *J. Virol.* 68, 1660–1666.
49. Merluzzi, V. J., Hargrave, K. D., Labadia, M., Grozinger, K., Skoog, M., Wu, J. C., Shih, C. K., Eckner, K., Hattox, S., Adams, J. & et al. (1990) *Science* 250, 1411–1413.
50. Romero, D. L., Busso, M., Tan, C. K., Reusser, F., Palmer, J. R., Poppe, S. M., Aristoff, P. A., Downey, K. M., So, A. G., Resnick, L. & et al. (1991) *Proc. Natl. Acad. Sci. USA* 88, 8806–8810.

51. Young, S. D., Britcher, S. F., Tran, L. O., Payne, L. S., Lumma, W. C., Lyle, T. A., Huff, J. R., Anderson, P. S., Olsen, D. B., Carroll, S. S. & et al. (1995) *Antimicrob. Agents Chemother.* 39, 2602–2605.

52. Tachedjian, G., Aronson, H. E. & Goff, S. P. (2000) *Proc. Natl. Acad. Sci. USA* 97, 6334–6339.

53. Crabtree, G. R. & Schreiber, S. L. (1996) *Trends Biochem. Sci.* 21, 418–422.

54. Balzarini, J., Brouwer, W. G., Felauer, E. E., De Clercq, E. & Karlsson, A. (1995) *Antiviral Res.* 27, 219–236.

55. Balzarini, J., Brouwer, W. G., Dao, D.C., Osika, E. M. & De Clercq, E. (1996) *Antimicrob. Agents Chemother.* 40, 1454–1466.

56. Dueweke, T. J., Poppe, S. M., Romero, D. L., Swaney, S. M., So, A. G., Downey, K. M., Althaus, I. W., Reusser, F., Busso, M., Resnick, L. & et al. (1993) *Antimicrob. Agents Chemother.* 37, 1127–1131.

57. Kleim, J. P., Bender, R., Kirsch, R., Meichsner, C., Paessens, A., Rosner, M., Rubsamen-Waigmann, H., Kaiser, R., Wichers, M., Schneweis, K. E. & et al. (1995) *Antimicrob. Agents Chemother.* 39, 2253–2257.

58. Ho, W., Kukla, M. J., Breslin, H. J., Ludovici, D. W., Grous, P. P., Diamond, C. J., Miranda, M., Rodgers, J. D., Ho, C. Y., De Clercq, E. & et al. (1995) *J. Med. Chem.* 38, 794–802.

59. Pauwels, R., Andries, K., Debyser, Z., Van Daele, P., Schols, D., Stoffels, P., De Vreese, K., Woestenborghs, R., Vandamme, A. M., Janssen, C. G. & et al. (1993) *Proc. Natl. Acad. Sci. USA* 90, 1711–1715.

60. Kuchin, S., Treich, I. & Carlson, M. (2000) *Proc. Natl. Acad. Sci. USA* 97, 7916–7920.

61. Szilvay, A. M., Nornes, S., Haugan, I. R., Olsen, L., Prasad, V. R., Endresen, C., Goff, S. P. & Helland, D. E. (1992) *J. Acquir. Immune Defic. Syndr.* 5, 647–657.

62. Ghosh, M., Jacques, P. S., Rodgers, D. W., Ottman, M., Darlix, J. L. & Le Grice, S. F. (1996) *Biochemistry* 35, 8553–8562.

63. Esnouf, R. M., Stuart, D. I., De Clercq, E., Schwartz, E. & Balzarini, J. (1997) *Biochem. Biophys. Res. Commun.* 234, 458–464.

64. Barnard, J., Borkow, G. & Parniak, M. A. (1997) *Biochemistry* 36, 7786–7792.

65. Maga, G., Ubiali, D., Salvetti, R., Pregnolato, M. & Spadari, S. (2000) *Antimicrob. Agents Chemother.* 44, 1186–1194.

66. Arnold, E. & Rossmann, M. G. (1990) *J. Mol. Biol.* 211, 763–801.

67. Lee, B. & Richards, F. M. (1971) *J. Mol. Biol.* 55, 379–400.

68. Ren, J., Milton, J., Weaver, K. L., Short, S. A., Stuart, D. I. & Stammers, D. K. (2000) *Structure Fold Des.* 8, 1089–1094.

69. Esnouf, R. M., Ren, J., Hopkins, A. L., Ross, C. K., Jones, E. Y., Stammers, D. K. & Stuart, D. I. (1997) *Proc. Natl. Acad. Sci. USA* 94, 3984–3989.

What is claimed:

1. A method of determining whether a compound enhances formation of a complex between a p66 subunit polypeptide of HIV-1 reverse transcriptase and a p51 subunit polypeptide of HIV-1 reverse transcriptase which comprises:

a) contacting a yeast cell with the compound, which cell comprises (i) a first plasmid which expresses a fusion protein comprising the p66 subunit polypeptide of HIV-1 reverse transcriptase, (ii) a second plasmid which expresses a fusion protein comprising the psi subunit polypeptide of HIV-1 reverse transcriptase, and (iii) a reporter gene which is activated in the presence of a complex between the p66 subunit polypeptide and the p51 subunit polypeptide;

b) determining a level of activity of the reporter gene in the cell in the presence of the compound; and c) comparing the level of activity of the reporter gene determined in step (b) with a level of activity of the reporter gene determined in the absence of the compound, wherein an increased level of activity of the reporter gene determined in step (b) compared to the level of activity determined in the absence of the compound indicates that the compound enhances formation of a complex between the p51 subunit polypeptide of HIV-1 reverse transcriptase and the p66 subunit polypeptide of HIV-1 reverse transcriptase.

2. A method of making a pharmaceutical composition which compriseS:

a) determining whether a compound not previously known enhances formation of a complex between a p66 subunit polypeptide of HIV-1 reverse transcriptase and a p51 subunit polypeptide of HIV-1 reverse transcriptase by the method of claim 1, b) recovering the compound if it is determined to enhance formation; and c) admixing the compound with a pharmaceutically acceptable carrier.

3. The method of claim 1, wherein (a) the fusion protein expressed by the first plasmid comprises a peptide having a DNA binding domain, and (b) the fusion protein expressed by the second plasmid comprises a peptide having a transcription activation domain.

4. The method of claim 3, wherein the DNA binding domain is a LexA DNA binding domain.

5. The method of claim 4, wherein the peptide having a DNA binding domain comprises LexA amino acid residues 1–87.

6. The method of claim 4, wherein the peptide having a DNA binding domain comprises LexA amino acid residues 1–202.

7. The method of claim 3, wherein the DNA binding domain is a GAL4 DNA binding domain.

8. The method of claim 3, wherein the transcription activation domain is a GAL4 transcription activation domain.

9. The method of claim 8, wherein the peptide having the transcription activation domain comprises GAL4 amino acid residues 768–881.

10. The method of claim 3, wherein the transcription activation domain is a VP16 transcription activation domain.

11. The method of claim 1, wherein (a) the fusion protein expressed by the first plasmid comprises a peptide having a transcription activation domain, and (b) the fusion protein expressed by the second plasmid comprises a peptide having a DNA binding domain.

12. The method of claim 11, wherein the DNA binding domain is a LexA DNA binding domain.

13. The method of claim 12, wherein the peptide having a DNA binding domain comprises LeXA amino acid residues 1–87.

14. The method of claim 12, wherein the peptide having a DNA binding domain comprises LexA amino acid residues 1–202.

15. The method of claim 11, wherein the DNA binding domain is a GAL4 DNA binding domain.

16. The method of claim 11, wherein the transcription activation domain is a GAL4 transcription activation domain.

17. The method of claim 16, wherein the transcription activation domain comprises GAL4 amino acid residues 768–881.

18. The method of claim 11, wherein the transcription activation domain is a VP16 transcription activation domain.

19. The method of claim 1, wherein the fusion protein expressed by the first plasmid, the second plasmid or both plasmids comprises a peptide comprising consecutive alanine residues.

20. The method of claim 19, wherein the peptide comprising consecutive alanine residues comprises at least 6 alanine residues.

21. The method of claim 1, wherein the fusion protein comprises an influenza hemagglutinin (HA) epitope tag.

22. The method of claim 1, wherein the reporter gene is a LacZ reporter gene.

23. The method of claim 1, wherein (a) the fusion protein expressed by the first plasmid comprises a peptide comprising a LexA protein DNA binding domain, wherein the p66 subunit polypeptide is bound at its C-terminal amino acid to a N-terminal amino acid of the peptide comprising a LexA protein DNA binding domain; and (b) the fusion protein expressed by the second plasmid comprises a Gal4 peptide corresponding to amino acids 768–881 of Gal4, and an influenza hemagglutiflin (HA) epitope tag, which Gal4 peptide is bound at its C-terminal amino acid to a N-terminal amino, acid of the influenza hemagglutinin (Ha) epitope tag, which influenza hemagglutinin (HA) epitope tag is bound at its C-terminal amino acid to a N-terminal amino acid of the p51 subunit polypeptide.

24. The method of claim 1, wherein (a) the fusion protein expressed by the first plasmid comprises a peptide comprising a LexA protein DNA binding domain, wherein the p66 subunit polypeptide is bound at it's C-terminal amino acid to a N-terminal amino acid of the peptide comprising a LexA protein DNA binding domain; and (b) the fusion protein expressed by the second plasrnid comprises a Gal4 peptide corresponding to amino acids 768–881 of Gal4, which Gal4 peptide is bound at its C-terminal amino acid to a N-terminal amino acid of the p51 subunit polypeptide.

25. The method of claim 1, wherein (a) the fusion protein expressed by the first plasmid comprises a LexA peptide corresponding to amino acid residues 1–87, wherein the LexA peptide is bound at its C-terminal amino acid to a N-terminal amino acid of the of the p66 subunit polypeptide; and (b) the fusion protein expressed by the second plasmid comprises a Gal4 peptide corresponding to amino acids 768–881 of Gal4, and an influenza hemagglutiflin (HA) epitope tag, which Gal4 peptide is bound at its C-terminal amino acid to a N-terminal amino acid of the influenza hemagglutinin (HA) epitope tag, which influenza hemagglutinin (HA) epitope tag is bound at its C-terminal amino acid to a N-terminal amino acid of the p51 subunit polypeptide.

26. The method of claim 1, wherein (a) the fusion protein expressed by the first plasmid comprises a LexA peptide corresponding to amino acid residues 1–87, wherein the LexA peptide is bound at its C-terminal amino acid to a N-terminal amino acid of the of the p66 subunit polypeptide; and (b) the fusion protein expressed by the second plasmid comprises a Gal4 peptide corresponding to amino acids 768–881 of Gal4, which Gal4 peptide is bound at its C-terminal amino acid to a N-terminal amino acid of the p51 subunit polypeptide.

27. The method of claim 1, wherein (a) the fusion protein expressed by the first plasmid comprises a LexA peptide corresponding to amino acid residues 1–202, and a peptide comprising six consecutive alanine residues, wherein the LexA peptide is bound at its C-terminal amino acid to a N-terminal amino acid of the peptide comprising six consecutive alanine residues, wherein the peptide comprising six consecutive alanine residues is bound at its C-terminal amino acid to a N-terminal amino acid of the p66 subunit polypeptide; and (b) the fusion protein expressed by the second plasmid comprises a Gal4 peptide corresponding to amino acids 768–881 of Gal4, which Gal4 peptide is bound at its C-terminal amino acid to a N-terminal amino acid of the p51 subunit polypeptide.

28. The method of claim 1, wherein (a) the fusion protein expressed by the first plasmid comprises a LexA peptide corresponding to amino acid residues 1–202, and a peptide comprising six consecutive alanine residues, wherein the LexA peptide is bound at its C-terminal amino acid to a N-terminal amino acid of the peptide comprising six consecutive alanine residues, wherein the peptide comprising six consecutive alanine residues is bound at its C-terminal amino acid to a N-terminal amino acid of the p66 subunit polypeptide; and (b) the fusion protein expressed by the second plasmid comprises a Gal4 peptide corresponding to amino acids 768–881 of Gal4, and an influenza hemagglutiflin (HA) epitope tag, which Gal4 peptide is bound at its C-terminal amino acid to a N-terminal amino acid of the influenza hemagglutinin (HA) epitope tag, which influenza hemagglutinin (HA) epitope tag is bound at its C-terminal amino acid to a N-terminal amino acid of the p51 subunit polypeptide.

29. The method of claim 1, wherein (a) the fusion protein expressed by the first plasmid comprises a Gal4 peptide corresponding to amino acids 768–881 of Gal4, an influenza hemagglutiflin (HA) epitope tag, and a peptide comprising six consecutive alanine residues, wherein the Gal4 peptide is bound at its C-terminal amino acid to a N-terminal amino acid of the influenza hemagglutinin (HA) epitope tag, wherein the influenza hemagglutinin (HA) epitope tag is bound at its C-terminal amino acid to a N-terminal amino acid of the peptide comprising six consecutive alanine residues, wherein the peptide comprising six consecutive alanine residues is bound at its C-terminal amino acid to a N-terminal amino acid of the p66 subunit polypeptide; and (b) the fusion protein expressed by second plasmid comprises a peptide comprising a LexA protein DNA binding domain, wherein the p51 subunit polypeptide is bound at its C-terminal amino acid to a N-terminal amino acid of the peptide comprising a LexA protein DNA binding domain.

30. The method of claim 1, wherein (a) the fusion protein expressed by the first plasmid comprises a Gal4 peptide corresponding to amino acids 768–881 of Gal4, an influenza hemagglutinin (HA) epitope tag, and a peptide comprising six consecutive alanine residues, wherein the Gal4 peptide is bound at its C-terminal amino acid to a N-terminal amino acid of the influenza hemagglutinin (HA) epitope tag, wherein the influenza hemagglutinin (HA) epitope tag is bound at its C-terminal amino acid to a N-terminal amino acid of the peptide comprising six consecutive alanine residues, wherein the peptide comprising six consecutive alanine residues is bound at its C-terminal amino acid to a N-terminal amino acid of the p66 subunit polypeptide; and (b) the fusion protein expressed by second plasmid comprises a peptide comprising a LexA protein DNA binding domain, wherein peptide comprising a LexA protein DNA binding domain is bound at its C-terminal amino acid to a N-terminal amino acid of the p51 subunit polypeptide.

31. The method of claim 1, wherein (a) the fusion protein expressed by the first plasmid comprises a Gal4 peptide corresponding to amino acids 768–881 of Gal4, an influenza hemagglutinin (HA) epitope tag, and a peptide comprising six consecutive alanine residues, wherein the Gal4 peptide is bound at its C-terminal amino acid to a N-terminal amino acid of the influenza hemagglutinin (HA) epitope tag, wherein the influenza hemagglutinin (HA) epitope tag is bound at its C-terminal amino acid to a N-terminal amino acid of the peptide comprising six consecutive alanine residues, wherein the peptide comprising six consecutive alanine residues is bound at its C-terminal amino acid to the a N-terminal amino acid of the p66 subunit polypeptide; and (b) the fusion protein expressed by second plasmid comprises a peptide comprising a Gal4 protein DNA binding domain, which peptide comprising a Gal4 protein DNA binding domain is bound at its C-terminal amino acid to a N-terminal amino acid of the psi subunit polypeptide.

32. The method of claim A wherein (a) the fusion protein expressed by the first plasmid comprises a Gal4 peptide corresponding to amino acids 768–881 of Gal4, wherein the Gal4 peptide is bound at its C-terminal amino acid to the a N-terminal amino acid of the p66 subunit polypeptide; and (b) the fusion protein expressed by second plasmid comprises a peptide comprising a LexA protein DNA binding domain, wherein the p51 subunit polypeptide is bound at its C-terminal amino acid to a N-terminal amino acid of the peptide comprising a LexA protein DNA binding domain.

33. The method of claim 1, wherein (a) the fusion protein expressed by the first plasmid comprises a Gal4 peptide corresponding to amino acids 768–881 of Gal4, wherein the Gal4 peptide is bound at its C-terminal amino acid to a N-terminal amino acid of the p66 subunit polypeptide; and (b) the fusion protein expressed by second plasmid comprises a peptide comprising a LexA protein DNA binding domain, which peptide comprising a LexA protein-DNA binding domain is bound at its C-terminal amino acid to a N-terminal amino acid of the p51 subunit polypeptide.

34. The method of claim 1, wherein (a) the fusion protein expressed by the first plasmid comprises a Gal4 peptide corresponding to amino acids 768–881 of Gal4, wherein the Gal4 peptide is bound at its C-terminal amino acid to a N-terminal amino acid of the p66 subunit polypeptide; and (b) the fusion protein expressed by second plasmid comprises a peptide comprising a Gal4 protein DNA binding domain, which peptide comprising a Gal4 protein DNA binding domain is bound at its C-terminal amino acid to a N-terminal amino acid of the p51 subunit polypeptide.

35. A method of enhancing formation of a complex between a p51 subunit polypeptide of HIV-1 reverse transcriptase and a p66 subunit polypeptide of HIV-1 reverse transcriptase, with a compound not previously known which comprises:

a) contacting a yeast cell with the compound, which cell comprises (i) a first plasmid which expresses a fusion protein comprising the p66 subunit polypeptide of HIV-1 reverse transcriptase, (ii) a second plasmid which expresses a fusion protein comprising the p51 subunit polypeptide of HIV-1 reverse transcriptase, and (iii) a reporter gene which is activated in the presence of a complex between the p66 subunit polypeptide and the p51 subunit polypeptide, and determining a level of activity of the reporter gene in the cell in the presence of the compound;

b) comparing the level of activity of the reporter gene determined in step (a) with a level of activity of the reporter gene determined in the absence of the compound, wherein an increased leveP of activity of the reporter gene determined in step (a) indicates that the compound enhances formation of a complex between the p51 subunit polypeptide of HIV-1 reverse transcriptase and the p66 subunit polypeptide of HIV-1 reverse transcriptase;

c) contacting either (1) the p51 subunit polypeptide, (2) the p66 subunit polypeptide, or (3) both the p51 subunit polypeptide and the p66 subunit polypeptide, with an effective amount of the compound determined to enhance formation of the complex in step (c), so to thereby enhance formation of a complex between the p51 subunit polypeptide of HIV-1 reverse transcriptase and a p66 subunit polypeptide of HIV-1 reverse transcriptase.

36. The method of claim 35, wherein the p51 subunit polypeptide of HIV-1 reverse transcriptase and the p66 subunit polypeptide of HIV-1 reverse transcriptase are present in a subject and the contacting is effected by administering the compound to the subject.

37. The method of claim 36, wherein the compound is administered orally, intravenously, subcutaneously, intramuscularly, topically or by liposome-mediated delivery.

38. The method of claim 36, wherein the subject is a human being, a primate, an equine, an avian, a bovine, a porcine, a canine, a feline or a mouse.

39. The method of claim 36, wherein the effective amount of the compound is between about 1 mg and about 50 mg per kg body weight of the subject.

40. The method of claim 39, wherein the effective amount of the compound is between about 2 mg and about 40 mg per kg body weight of the subject.

41. The method of claim 40, wherein the effective amount of the compound is between about 3 mg and about 30 mg per kg body weight of the subject.

42. The method of claim 41, wherein the effective amount of the compound is between about 4 mg and about 20 mg per kg body weight of the subject.

43. The method of claim 42, wherein the effective amount of the compound is between about 5 mg and about 10 mg per kg body weight of the subject.

44. The method of claim 43, wherein the compound is administered at least once per day.

45. The method of claim 36, wherein the compound is administered daily.

46. The method of claim 36, wherein the compound is administered every other day.

47. The method of claim 36, wherein the compound is administered every 6 to 8 days.

48. The method of claim 36, wherein the compound is administered weekly.

* * * * *